US008916570B2

(12) United States Patent
Jacobson et al.

(10) Patent No.: US 8,916,570 B2
(45) Date of Patent: Dec. 23, 2014

(54) A₃ ADENOSINE RECEPTOR AGONISTS AND ANTAGONISTS

(75) Inventors: Kenneth A. Jacobson, Silver Spring, MD (US); Dilip K. Tosh, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 13/371,081

(22) Filed: Feb. 10, 2012

(65) Prior Publication Data

US 2012/0184569 A1 Jul. 19, 2012

Related U.S. Application Data

(63) Continuation-in-part of application No. 12/935,461, filed as application No. PCT/US2009/038026 on Mar. 24, 2009, application No. 13/371,081, which is a continuation-in-part of application No. 13/056,997, filed as application No. PCT/US2009/052439 on Jul. 31, 2009.

(60) Provisional application No. 61/040,985, filed on Mar. 31, 2008, provisional application No. 61/085,588, filed on Aug. 1, 2008.

(51) Int. Cl.
*A61K 31/52* (2006.01)
*C07D 473/34* (2006.01)

(52) U.S. Cl.
CPC .................................... *C07D 473/34* (2013.01)
USPC ..................... 514/263.4; 544/263.4

(58) Field of Classification Search
USPC .............. 544/277; 514/263.4, 263.2, 363.22
See application file for complete search history.

(56) References Cited

U.S. PATENT DOCUMENTS

| | | | |
|---|---|---|---|
| 5,646,156 A | 7/1997 | Jacobson et al. | |
| 5,688,774 A | 11/1997 | Jacobson et al. | |
| 5,773,423 A | 6/1998 | Jacobson et al. | |
| 5,840,728 A | 11/1998 | Marquez et al. | |
| 6,066,642 A | 5/2000 | Jacobson et al. | |
| 6,187,284 B1 | 2/2001 | Griffiths | |
| 6,197,278 B1 | 3/2001 | Blankenberg et al. | |
| 6,211,165 B1 | 4/2001 | Liang et al. | |
| 6,528,516 B1 | 3/2003 | Civan et al. | |
| 6,586,413 B2 | 7/2003 | Liang et al. | |
| 7,087,589 B2 | 8/2006 | Jacobson et al. | |
| 2003/0143282 A1 | 7/2003 | Fishman | |
| 2003/0216412 A1 | 11/2003 | Jacobson et al. | |
| 2004/0132686 A1 | 7/2004 | Van Tilburg et al. | |
| 2006/0040959 A1 | 2/2006 | Baraldi et al. | |
| 2006/0100168 A1 | 5/2006 | Ravid et al. | |
| 2007/0232626 A1 | 10/2007 | Jacobson et al. | |
| 2011/0046166 A1* | 2/2011 | Jacobson et al. .......... 514/263.24 |
| 2011/0171130 A1* | 7/2011 | Jacobson et al. ............. 424/1.85 |
| 2012/0184569 A1 | 7/2012 | Jacobson et al. | |
| 2012/0252823 A1* | 10/2012 | Jacobson et al. ............ 514/263.4 |
| 2012/0264769 A1* | 10/2012 | Jacobson et al. ............ 514/263.2 |
| 2012/0270829 A1* | 10/2012 | Salvemini ........................ 514/46 |

FOREIGN PATENT DOCUMENTS

| | | |
|---|---|---|
| EP | 1 798 233 A1 | 6/2007 |
| WO | WO 01/51490 A | 7/2001 |
| WO | WO 2006/031505 A1 | 3/2006 |
| WO | WO 2006091905 A1 | 8/2006 |
| WO | WO 2006/113204 A2 | 10/2006 |
| WO | WO 2006/125190 A1 | 11/2006 |
| WO | WO 2006/128159 A2 | 11/2006 |
| WO | WO 2007/002139 A2 | 1/2007 |
| WO | WO 2007/009757 A1 | 1/2007 |
| WO | WO 2007/043054 A1 | 4/2007 |
| WO | WO 2007/063538 A1 | 6/2007 |
| WO | WO 2007/086044 A1 | 8/2007 |

(Continued)

OTHER PUBLICATIONS

Tosh, Bioorganic & Medicinal Chemistry (2010), 18(2), 508-517.*
Baraldi, Pier. Chem. Rev. 2008, 108, 238-263.*
Silverman, Michael. J. Rheumatology 2008, 35: 41-8.*
Avni, Isaac. Ophthalmology Jul. 2010, 117(7), 1287-1293.*
Glaucoma Causes—Diseases and Conditions. Mayo Clinic. 2012. <http://www.mayoclinic.org/diseases-conditions/glaucoma/basics/causes/con-20024042>.*

(Continued)

*Primary Examiner* — Golam M M Shameem
*Assistant Examiner* — Laura Daniel
(74) *Attorney, Agent, or Firm* — Leydig, Voit & Mayer, Ltd.

(57) ABSTRACT

Disclosed are (N)-methanocarba adenine nucleosides of formulas (I)-(V), for example, of formula (V):

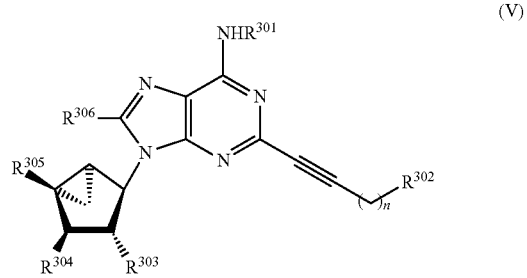

(V)

as highly potent $A_3$ adenosine receptor agonists, pharmaceutical compositions comprising such nucleosides, and a method of use of these nucleosides, wherein $R_1$-$R_6$ are as defined in the specification. These nucleosides exhibit similar selectivities as agonists of the $A_3$ versus the $A_1$ receptor for both human and mouse adenosine receptors, and are contemplated for use in the treatment a number of diseases, for example, inflammation, cardiac ischemia, stroke, asthma, diabetes, and cardiac arrhythmias.

18 Claims, 14 Drawing Sheets

(56) References Cited

FOREIGN PATENT DOCUMENTS

| WO | WO 2007/103970 A2 | 9/2007 |
|---|---|---|
| WO | WO 2007/139775 A2 | 12/2007 |
| WO | WO 2007/147659 A1 | 12/2007 |
| WO | WO 20071139946 A2 | 12/2007 |
| WO | WO 2008/006369 A1 | 1/2008 |
| WO | WO 2008/023362 A2 | 2/2008 |
| WO | WO 2008/055711 A2 | 5/2008 |
| WO | WO 2008/056361 A1 | 5/2008 |
| WO | WO 2008/058238 A2 | 5/2008 |
| WO | WO 2008/075201 A2 | 6/2008 |

OTHER PUBLICATIONS

Auchampach, John. Am. J. Physiol heart Circ. Physiol. Aug. 2003, 285(2).*

Auchampach et al., "Synthesis and pharmacological characterization of [$^{125}$I]MRS5127, a high affinity, selective agonist radioligand for the $A_3$ adenosine receptor," *Biochem. Pharmacol.*, 79 (7), 967-973 (2010).

Bar-Yehuda et al., "The $A_3$ adenosine receptor agonist CF102 induces apoptosis of hepatocellular carcinoma via de-regulation of the Wnt and NF-κB signal transduction pathways," *Int. J. Oncol.*, 33 (2), 287-295 (2008).

Bradford, "A Rapid and Sensitive Method for the Quantitation of Microgram Quantities of Protein Utilizing the Principle of Protein-Dye Binding," *Anal. Biochem.*, 72, 248-254 (1976).

Cheng et al., "Relationship between the inhibition constant ($K_1$) and the concentration of inhibitor which causes 50 per cent inhibition ($I_{50}$) of an enzymatic reaction," *Biochem. Pharmacol.*, 22, 3099-3108 (1973).

Cordeaux et al., "Agonist-occupied $A_3$ adenosine receptors exist within heterogeneous complexes in membrane microdomains of individual living cells," *FASEB J.*, 22 (3), 850-860 (2008).

Fishman et al., "An agonist to the $A_3$ adenosine receptor inhibits colon carcinoma growth in mice via modulation of GSK-3β and NF-κB," *Oncogene*, 23, 2465-2471 (2004).

Fredholm et al., "International Union of Pharmacology. XXV. Nomenclature and Classification of Adenosine Receptors," *Pharmacol. Rev.*, 53 (4), 527-552 (2001).

Gao et al., "Partial Agonists for $A_3$ Adenosine Receptors," *Curr. Top. Med. Chem.*, 4, 855-862 (2004).

Gao et al., "Structural Determinanats of $A_3$ Adenosine Receptor Activation: Nucleoside Ligands at the Agonist/Antagonist Boundary," *J. Med. Chem.*, 45 (20), 4471-4484 (2002).

Gao et al., "Synthesis and pharmacological characterization of [$^{125}$I]MRS1898, a high-affinity, selective radioligand for the rat $A_3$ adenosine receptor," *Purinergic Signal.*, 5 (1), 31-37 (2009).

Ge et al., "CI-IB-MECA [2-chloro-$N^6$-(3-iodobenzyl)adenosine-5'-N-methylcarboxamide] reduces ischemia/reperfusion injury in mice by activating the $A_3$ adenosine receptor," *J. Pharmacol. Exp. Ther.*, 319 (3), 1200-1210 (2006).

Hofer et al., "Homeostatic Action of Adenosine $A_3$ and $A_1$ Receptor Agonists on proliferation of Hematopoietic Precursor Cells," *Exp. Biol. Med.*, 233 (7), 897-900 (2008).

Jacobson et al., "Semi-rational design of (north)-methanocarba nucleosides as dual acting $A_1$ and $A_3$ adenosine receptor agonists: novel prototypes for cardioprotection," *J. Med. Chem. Letters*, 48 (26), 8103-8107 (2005) (with supporting material).

Joshi et al., "Purine derivatives as ligands for $A_3$ adenosine receptors," *Curr. Top. Med. Chem.*, 5 (13), 1275-1295 (2005).

Joshi et al., "A new synthetic route to (North)-methanocarba nucleosides designed as $A_3$ adenosine receptor agonists," *J. Org. Chem.*, 70 (2), 439-447 (2005).

Kiesewetter et al., "Synthesis and characterization of [$^{76}$Br]-labeled high-affinity $A_3$ adenosine receptor ligands for positron emission tomography," *Nucl. Med. Biol.*, 36 (1), 3-10 (2009).

Kim et al., "2-Substitution of $N^6$-Benzyladenosine-5'-uronamides Enhances Selectivity for $A_3$ Adenosine Receptors," *J. Med. Chem.*, 37, 3614-3621 (1994).

Kreckler et al., "Adenosine inhibits tumor necrosis factor-α release from mouse peritoneal macrophages via $A_{2A}$ and $A_{2B}$ but not the $A_3$ adenosine receptor," *J. Pharmacol. Exp. Ther.*, 317 (1), 172-180 (2006).

Lasley et al., "The $A_{2a}/A_{2b}$ receptor antagonist ZM-241385 blocks the cardioprotective effect of adenosine agonist pretreatment in in vivo rat myocardium," *Am. J. Physiol, Heart Circ. Physiol.*, 292, H426-H431 (2007).

Lee et al., "Ring-Constrained (N)-Methanocarba Nucleosides as Adenosine Receptor Agonists: Independent 5'-Uronamide and 2'-Deoxy Modifications," *Bioorg. Med. Chem. Lett.*, 11, 1333-1337 (2001).

Liu et al., "Evidence that the adenosine $A_3$ receptor may mediate the protection afforded by preconditioning in the isolated rabbit heart," *Cardiovasc Res.*, 28, 1057-1061 (1994).

Melman et al., "Design of (N)-methanocarba adenosine 5'-uronamides as species-independent $A_3$ receptor-selective agonists," *Bioorg. Med. Chem. Lett.*, 18 (9), 2813-2819 (2008).

Melman et al., "Selective $A_3$ Adenosine Receptor Antagonists Derived from Nucleosides Containing a Bicyclo[3.1.0]hexane Ring System," *Bioorg. Med. Chem.*, 16 (18), 8546-8556 (2008).

Morello et al., "CI-IB-MECA inhibits human thyroid cancer cell proliferation independently of A3 adenosine receptor activation," *Cancer Biol. Ther.*, 7 (2), 278-284 (2008).

Ohta at al., "Role of G-protein-coupled adenosine receptors in downregulation of inflammation and protection from tissue damage," *Nature*, 414, 916-920 (2001).

PCT/US09/38026 International Search Report dated Jul. 8, 2009.

PCT/US09/52439 International Search Report dated Aug. 3, 2010.

Pedata et al., "The role of ATP and adenosine in the brain under normoxic and ischemic conditions," *Purinergic Signal.*, 3 (4), 299-310 (2007).

Ramkumar et al., "The $A_3$ Adenosine Receptor Is the Unique Adenosine Receptor Which Facilitates Release of Allergic Mediators in Mast Cells," *J. Biol. Chem.*, 268, 16887-16890 (1993).

Strickler et al., "Direct Preconditioning of Cultured Chick Ventricular Myocytes," *J. Clin. Invest.*, 98, 1773-1779 (1996).

Takahashi et al., "Effects of adenosine on adhesion molecule expression and cytokine production in human PBMC depend on the receptor subtype activated," *Br. J. Pharmacol.*, 150 (6), 816-822 (2007).

Tchilibon et al., "(N)-methanocarba 2,$N^6$-Disubstituted Adenine Nucleosides as Highly Potent and Selective $A_3$ Adenosine Receptor Agonists," *J. Med. Chem.*, 48, 1745-1758 (2005).

Von Lubitz et al., "Adenosine $A_3$ receptor stimulation and cerebral ischemia," *Eur. J. Pharmacol.*, 263, 59-67 (1994).

Wan et al., "The $A_3$ adenosine receptor agonist CP-532,903 [$N^6$-(2,5-dichlorobenzyl)-3'-aminoadenosine-5'-N-methyicarboxamide] protects against myocardial ischemia/reperfusion injury via the sarcolemmal ATP-sensitive potassium channel," *J. Pharmacol. Exp. Ther.*, 324 (1), 234-243 (2008).

Wunderlich et al., "Dual purinergic synaptic transmission in the human enteric nervous system," *Am. J. Physiol. Gastrointest. Liver Physiol.*, 294 (2), G554-G566 (2008).

Zheng et al., "Protective roles of adenosine $A_1$, $A_{2A}$, and $A_3$ receptors in skeletal muscle ischemia and reperfusion injury," *Am. J. Physiol. Heart Circ. Physiol.*, 293 (6), H3685-H3691 (2007).

Elzein et al., "$N^6$-Cycloalkyl-2-substituted adenosine derivaties as selective, high affinity adenosine $A_1$ receptor agonists," *Bioorg. Med. Chem. Lett.* 17, 161-166 (2007).

Tosh et al., "Truncated (N)-Methanocarba Nucleosides as A1 Adenosine Receptor Agonists and Partial Agonists: Overcoming Lack of a Recognition Element,", *ACS Med. Chem. Lett.*, 2, 626-631 (2011) and Supporting Information.

Tosh, "2-Dialkynyl derivatives of (N)-methanocarba nucleosides: Clickable $A_3$ adenosine receptor-selective agonists," *Bioorganic & Medicinal Chemistry*, 18(2), 508-517 (2010).

Wermuth, "Molecular Variations Based on Isosteric Replacements," *The Practice of Medicinal Chemistry, Academic Press*, 203-237 (1996).

* cited by examiner

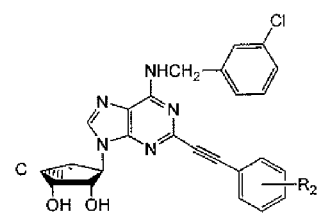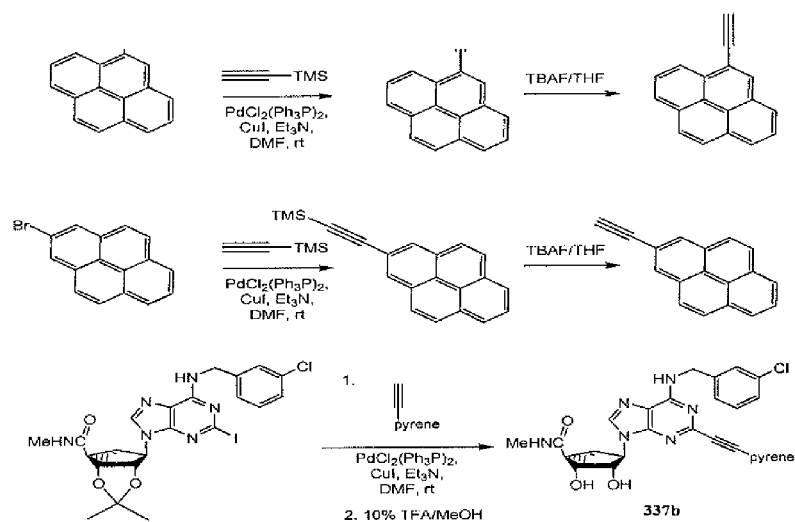
Fig. 15 ature 2001; 414:916-920; and causes
A₃ ADENOSINE RECEPTOR AGONISTS AND ANTAGONISTS

CROSS-REFERENCE TO RELATED APPLICATIONS

This patent application is a continuation-in-part of copending U.S. patent application Ser. No. 12/935,461, which is the U.S. national phase of PCT/US2009/038026, filed Mar. 24, 2009, which claims the benefit of U.S. Provisional Patent Application No. 61/040,985, filed Mar. 31, 2008. This patent application is also a continuation-in-part of copending U.S. patent application Ser. No. 13/056,997, which is the U.S. national phase of PCT/US2009/052439, filed Jul. 31, 2009, which claims the benefit of U.S. Provisional Patent Application No. 61/085,588, filed Aug. 1, 2008. The disclosures of the '461, '026, '985, '997, '439, and '588 applications are incorporated herein by reference.

BACKGROUND OF THE INVENTION

Extracellular adenosine acts as a local modulator at four subtypes of adenosine receptors, namely, $A_1$, $A_{2A}$, $A_{2B}$, and $A_3$, which are involved in numerous physiological and pathophysiological processes. Fredholm et al., *Pharmacol. Rev.* 2001; 53:527-52. For example, adenosine attenuates the effects of ischemia in the heart and brain. Acting through the $A_{2A}$ adenosine receptor, it suppresses prolonged inflammation; Ohta et al., *Nature* 2001; 414:916-920; and causes vasodilation and inhibits platelet aggregation, thus increasing the amount of oxygen available to an organ under stress. Adenosine agonists selective for the $A_3$ adenosine receptor are of interest as cerebroprotective, cardioprotective, and anticancer agents. von Lubitz et al., *Eur. J. Pharmacol.,* 1994, 263:59-67; Liu et al., *Cardiovasc Res.,* 1994, 28:1057-61; Strickler et al., *J. Clin. Invest.,* 1996, 98:1773-9; Fishman et al., *Oncogene,* 2004, 23:2465-71.

The potential utility of $A_1$ and $A_2$-selective agents in therapeutic applications has been limited by accompanying side effects, given the ubiquitous nature of the $A_1$ and $A_2$ receptors. The distribution of the $A_3$ adenosine receptor, by contrast, is fairly limited, being found primarily in the CNS, brain, testes, and immune system, where it appears to be involved in the modulation of release from mast cells of mediators of the immediate hypersensitivity reaction (Ramkumar et al., *J. Biol. Chem.,* 268, 16887-16890 (1993)). The limited distribution of the $A_3$ adenosine receptor provides a basis for predicting that $A_3$-selective compounds may be more useful than $A_1$- and $A_2$-selective compounds as potential therapeutic agents.

It is believed that $A_3$ adenosine receptor selective antagonists should serve as cerebroprotective, antiasthmatic, or anti-inflammatory agents. It is also believed that $A_3$ adenosine receptor selective antagonists should serve in the treatment of glaucoma, for example, in reducing intraocular pressure. Research activity is evident in the area of $A_3$ adenosine receptor antagonists; see, for example, U.S. Pat. Nos. 6,066,642 and 6,528,516 and WO 2008/055711. Accordingly, there is a desire to find new $A_3$ adenosine receptor antagonists.

Further, $A_3$ adenosine receptor partial agonists, are advantageous in cardioprotection and produce anti-ischemic effects. Partial agonists also tend to have less side effects than full agonists. In addition, partial agonists are less likely to produce desensitization of the receptor as compared to full agonists. Accordingly, partial agonists can activate the receptor for a longer duration and achieve longer lasting response. Accordingly, there is a desire to find new $A_3$ adenosine receptor partial agonists.

Accordingly, there is a great interest for finding $A_3$ adenosine receptor agonists, as shown by the patenting activity in this area; see, for example, U.S. Pat. Nos. 5,773,423 and 5,688,774; and U.S. Published Patent Application No. 2003/0216412 A1. Therefore, there is a desire for $A_3$ adenosine receptor agonists, especially those that are selective to $A_3$ adenosine receptor over the $A_1$ and $A_2$ adenosine receptors.

BRIEF SUMMARY OF THE INVENTION

The invention provides $A_3$ selective agonists, particularly N-methanocarba adenine nucleosides, for example, with selected substituents at the 2, $N^6$, 2', 3', 4', and/or 5'-positions, pharmaceutical compositions comprising such nucleosides, and methods of use thereof, for example, in a method for selectively activating an $A_3$ adenosine receptor of a mammal comprising administering to the mammal an effective amount of a nucleoside of the invention. Compounds in accordance with the embodiments of the invention exhibit similar selectivities as agonists of the $A_3$ versus the $A_1$ receptor which are species-independent.

BRIEF DESCRIPTION OF THE SEVERAL VIEWS OF THE DRAWINGS

FIG. 14 depicts a reaction scheme for the synthesis of compound of formula V wherein $R^5$ is hydrogen, in accordance with an embodiment of the invention.

FIG. 15 depicts a reaction scheme for the synthesis of compound 337b in accordance with an embodiment of the invention.

DETAILED DESCRIPTION OF THE INVENTION

Figure 1:
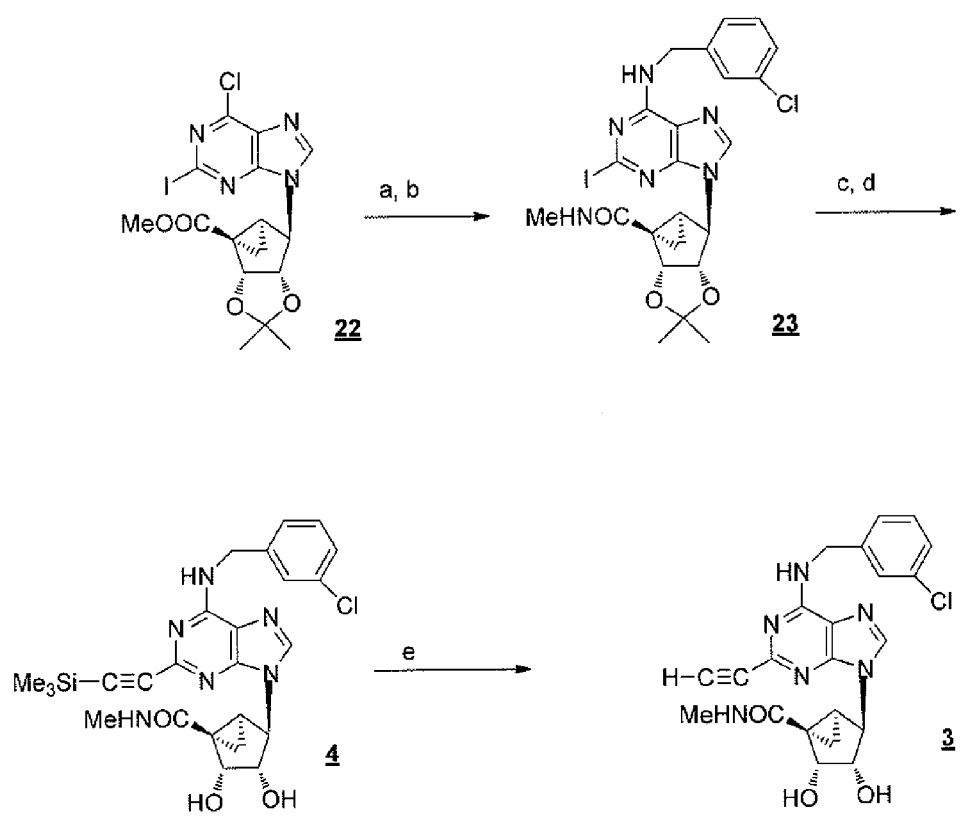
FIG. 1 depicts a reaction scheme for the synthesis of compounds 3 and 4 in accordance with an embodiment of the invention. Reagents and conditions: (a) 3-chlorobenzylamine; (b) MeNH$_2$, EtOH; (c) Me$_3$SiC≡CH, PdCl$_2$(PPh$_3$)$_2$, CuI, DMF, Et$_3$N; (d) TFA, MeOH, H$_2$O; (e) n-Bu$_4$NF, THF.
Figure 2:
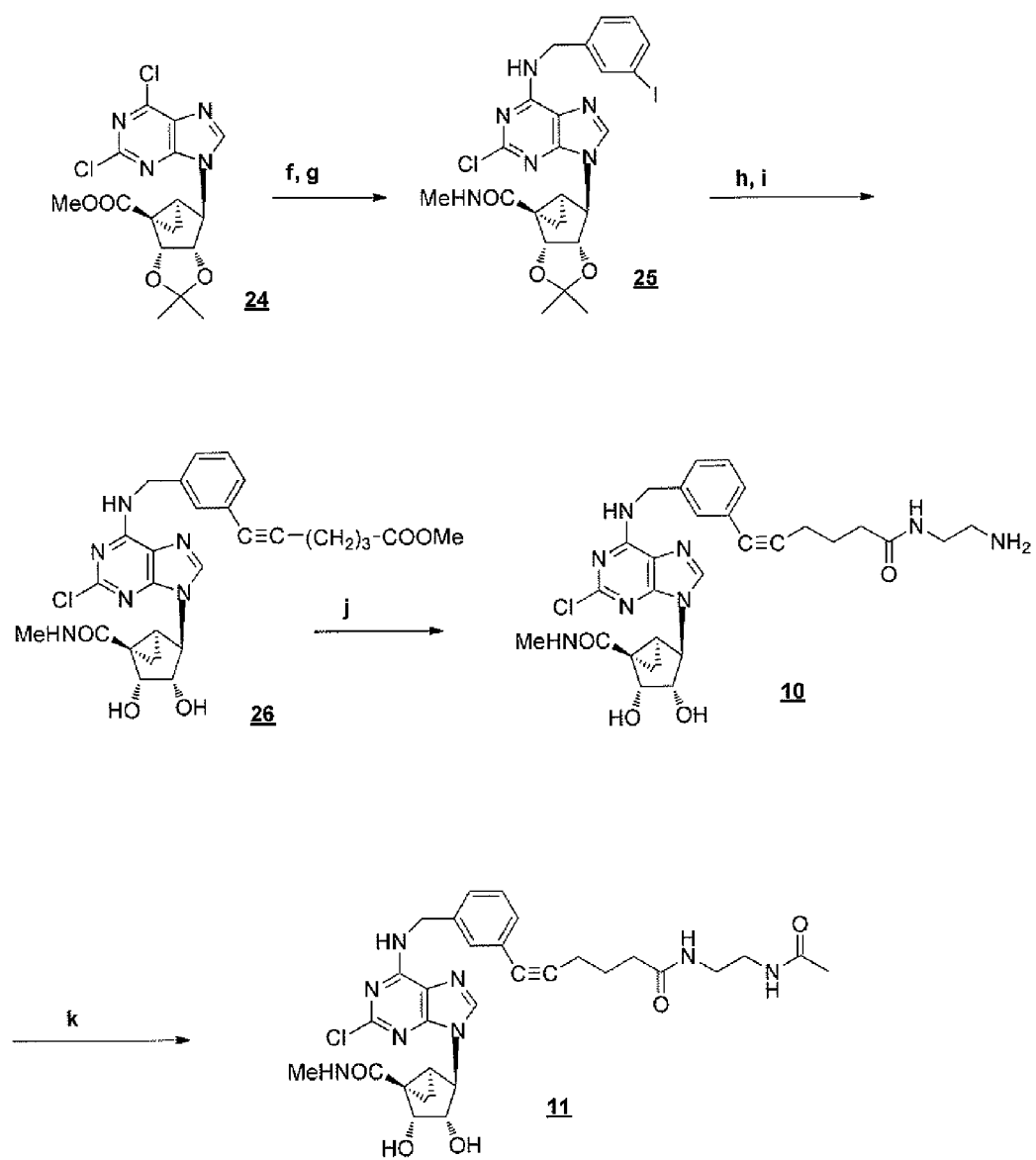
FIG. 2 depicts a reaction scheme for the synthesis of compounds 26, 10, and 11 in accordance with an embodiment of the invention. Reagents and conditions: (f) 3-iodobenzylamine; (g) MeNH$_2$, EtOH; (h) HC≡C(CH$_2$)$_3$COOCH$_3$, CuI, DMF, Et$_3$N; (i) TFA, MeOH, H$_2$O; (j) H$_2$NCH$_2$CH$_2$NH$_2$; (k) Ac$_2$O.

The present invention is predicated on the concept that adenosine analogues having a ring constraint and optionally having large lipophilic substituents at the C-2 and/or $N^6$-positions would display high selectivity as agonists of the $A_3$ adenosine receptor versus the $A_1$ and $A_{2A}$ adenosine receptors for both human and mouse and/or rat adenosine receptors.

Accordingly, in accordance with an embodiment, the present invention provides compounds of Formula (I):

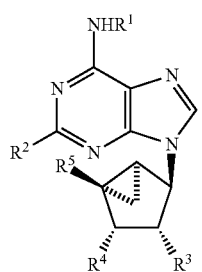

(I)

wherein:

$R^1$ is selected from the group consisting of $C_1$-$C_6$ alkyl, $C_1$-$C_6$ alkoxy, hydroxyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl)amino]-carbonyl]-$C_1$-$C_6$ alkyl]aniline]carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R^1$ is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof; and the alkyl or cycloalkyl portion of $R^1$ is optionally substituted with one or more substituents selected from the group consisting of halo, amino, alkyl, alkoxy, aryloxy, hydroxyalkyl, hydroxyalkenyl, hydroxyalkynyl, aminocarbonylalkoxy, and arylalkoxy, and any combination thereof;

$R^2$ is selected from the group consisting of iodo, $C_1$-$C_{20}$ alkyl, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, $C_1$-$C_{20}$ alkyl $C_2$-$C_{20}$ alkynyl, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, or aryl portion of $R^2$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkylaminocarbonyl, aminoalkylaminocarbonyl, trialkylsilyl, and any combination thereof; or $R^2$ is selected from the group consisting of amino (alkylamino)$_n$ alkylaminocarbonyl wherein n is 1 to 6, aminoalkylcarbonylaminoalkylaminocarbonyl, aminoalkylaminocarbonyl whose amino end is linked to a label, amino (alkylamino)$_n$ alkylaminocarbonyl wherein n is 1 to 6 whose amino end is linked to a label, and aminoalkylcarbonylaminoalkylaminocarbonyl whose amino end is linked to a label;

$R^3$ and $R^4$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^5$ is selected from the group consisting of $C_1$-$C_3$ alkyl aminocarbonyl, di($C_1$-$C_3$ alkyl)aminocarbonyl, $C_1$-$C_3$ alkylthio $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl;

or a pharmaceutically acceptable salt thereof, with the proviso that when $R^2$ is iodo, $R^3$ and $R^4$ are hydroxyl, and $R^5$ is methylaminocarbonyl, $R^1$ is not 3-chlorobenzyl.

In an embodiment, $R^1$ is selected from the group consisting of $C_1$-$C_6$ alkyl, $C_3$-$C_8$ cycloalkyl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_3$-$C_8$ cycloalkyl, and heterocyclyl $C_1$-$C_6$ alkyl, wherein the aryl or heterocyclyl portion of $R^1$ is optionally substituted with one or more substituents selected from the group consisting of halo, amino, $C_1$-$C_6$ alkyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy, and any combination thereof. Preferably, $R^1$ is selected from the group consisting of methyl, cyclopentyl, benzyl, diphenylethyl, phenyl cyclopropyl, diphenyl cyclopropyl, and 2,2-diphenylethyl, wherein the phenyl portion of $R^1$ is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_1$-$C_6$ alkoxy, phenoxy, hydroxy $C_1$-$C_6$ alkyl, hydroxy $C_2$-$C_6$ alkenyl, hydroxy $C_2$-$C_6$ alkynyl, and any combination thereof. In a specific embodiment, $R^1$ is benzyl.

In another embodiment, $R^1$ is methyl. In a further embodiment, $R^1$ is cyclopentyl or 7-norbornyl. Other embodiments include those wherein $R^1$ is trans-2-phenyl-1-cyclopropyl or 2,2-diphenylethyl.

A specific example of $R^1$ is benzyl substituted with one or more substituents selected from the group consisting of halo, amino, methyl, methoxy, phenoxy, hydroxymethyl, hydroxypropynyl, carboxypropynyl, alkoxycarbonylpropynyl, aminocarbonyl methoxy, and benzyloxy, and any combination thereof. When the benzyl group is monosubstituted, the substitution can be at the 2-, 3-, or 4-position of the benzyl group, and is preferably at the 3-position of the benzyl group. Specific examples of substituted benzyl groups are 3-chlorobenzyl, 3-bromobenzyl, 3-iodobenzyl, 3-(3-hydroxypropynyl) benzyl, and 2,5-dimethoxybenzyl.

In any of the embodiments discussed above, $R^2$ is preferably selected from the group consisting of iodo, $C_2$-$C_{20}$ alkynyl, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, and $C_6$-$C_{14}$ aryl $C_2$-$C_{20}$ alkynyl. More preferably, $R^2$ is $C_2$-$C_{20}$ alkynyl. Optionally, $R^2$ is substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkylaminocarbonyl, aminoalkylaminocarbonyl, trialkylsilyl, and any combination thereof. More preferably, $R^2$ is substituted with one or more substituents selected from the group consisting of amino, alkylamino, dialkylamino, carboxy, alkoxycarbonyl, aminocarbonyl, aminoalkylaminocarbonyl, trialkylsilyl, and any combination thereof.

In any of the embodiments discussed above, $R^3$ and $R^4$ are preferably independently selected from the group consisting of hydroxyl, amino, mercapto (i.e., SH), and ureido, and more preferably $R^3$ and $R^4$ are hydroxyl.

In any of the embodiments discussed above, $R^5$ is preferably selected from the group consisting of $C_1$-$C_3$ alkyl aminocarbonyl, di($C_1$-$C_3$ alkyl)aminocarbonyl, $C_1$-$C_3$ alkylthio $C_1$-$C_3$ alkyl, halo $C_1$-$C_3$ alkyl, amino $C_1$-$C_3$ alkyl, hydroxy $C_1$-$C_3$ alkyl, and $C_3$-$C_6$ cycloalkylamino, more preferably $R^5$ is $C_1$-$C_3$ alkyl aminocarbonyl or di($C_1$-$C_3$ alkyl)aminocarbonyl, and even more preferably $R^5$ is methylaminocarbonyl.

Specific examples of the compounds of the invention are compounds wherein $R^1$ is 3-chlorobenzyl, $R^3$ and $R^4$ are hydroxyl, and $R^5$ is methylamino carbonyl, and $R^2$ is ethynyl, 2-trimethylsilylethynyl, 1-pentynyl, 5-carbomethoxy-1-pentynyl, 5-carboxy-1-pentynyl, 5-(2-aminoethyl)aminocarbonyl-1-pentynyl, or iodo; and $R^1$ is 2,5-dimethoxybenzyl, $R^2$ is iodo, $R^3$ and $R^4$ are hydroxyl, and $R^5$ is methylaminocarbonyl.

In accordance with an embodiment, the invention provides a compound of formula I, wherein $R^2$ is selected from the group consisting of carboxyalkylalkynyl, alkoxycarbonylalkylalkynyl, aminoalkylaminocarbonylalkyl alkynyl, amino (alkylamino)$_n$ alkylaminocarbonyl wherein n is 1 to 6, aminoalkylcarbonylaminoalkylaminocarbonyl, aminoalkylaminocarbonyl whose amino end is linked to a label, dye, or reporter group, amino (alkylamino)$_n$ alkylaminocarbonyl wherein n is 1 to 6 whose amino end is linked to a label, dye, or reporter group, aminoalkylcarbonylaminoalkylaminocarbonyl whose amino end is linked to a label, dye, or reporter group, for example, a dye, particularly a fluorescent dye. The label can be a radioactive group such as $^{125}$I.

In a particular embodiment, the invention provides a compound of formula I, wherein $R^1$ is 3-chlorobenzyl, $R^2$ is selected from the group consisting of C≡C(CH$_2$)$_2$COOH, C≡C(CH$_2$)$_4$COOH, C≡C(CH$_2$)$_2$COOCH$_3$, C≡C(CH$_2$)$_4$COOCH$_3$, C≡C(CH$_2$)$_2$CONH(CH$_2$)$_2$NH$_2$, C≡C(CH$_2$)$_4$CONH(CH$_2$)$_2$NH$_2$, C≡C(CH$_2$)$_2$CONH(CH$_2$)$_3$NH$_2$, C≡C(CH$_2$)$_2$CONH(CH$_2$)$_4$NH$_2$, C≡C(CH$_2$)$_2$CO[NH(CH$_2$)$_2$]$_2$NH$_2$, C≡C(CH$_2$)$_2$CONH(CH$_2$)$_2$NH-biotin, and C≡C(CH$_2$)$_2$CONH(CH$_2$)$_2$NH—CO(CH$_2$)$_5$NH-biotin, and C≡C(CH$_2$)$_2$CONH(CH$_2$)$_2$NH—CO—(CH$_2$)$_5$Cy5 wherein Cy5 is a cyanine dye, $R^3$ and $R^4$ are hydroxyl, and $R^5$ is methylamino carbonyl, or a pharmaceutically acceptable salt thereof.

A specific example of a compound of formula I, wherein $R^1$ is 3-chlorobenzyl and $R^2$ is C≡C(CH$_2$)$_2$CONH(CH$_2$)$_2$NH—CO—(CH$_2$)$_5$Cy5 is compound 44.

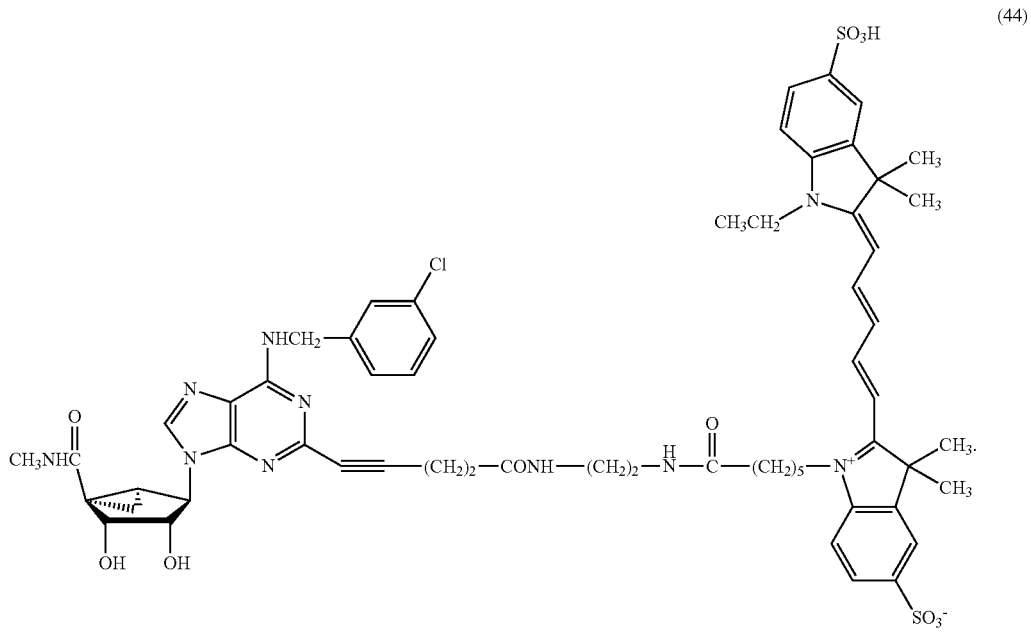

(44)

Among the N$^6$-3-chlorobenzyl, 5'-N-methylamide substituted compounds of the invention, the 2-ethynyl, N$^6$-3-chlorobenzyl analog 3 displayed K$_i$ values at the human and mouse A$_3$ adenosine receptors of 1.30 nM and 0.85 nM, respectively, while exhibiting selectivities for the A$_3$ versus the A$_1$ adenosine receptors of 134 for human and 53.6 for mouse. Other N$^6$-3-chlorobenzyl analog analogues such as the 2-(2-trimethylsilylethynyl) derivative 4, the 2-(1-pentynyl) derivative 5, the 2-(5-methoxycarbonyl-1-pentynyl) derivative 6, the 2-(5-carboxy-1-pentynyl) derivative 7, and the 2-(542-aminoethyl)aminocarbonyl-1-pentynyl) derivative 8 all exhibited $K_i$ values at the human $A_3$ adenosine receptor of about 2 nM or less, with a selectivity for the human $A_3$ adenosine receptor versus the $A_1$ adenosine receptor of 160 to 6260, while exhibiting $K_i$ values at the mouse $A_3$ adenosine receptor of about 8.7 nM or less, with a selectivity for the mouse $A_3$ adenosine receptor versus the mouse $A_1$ adenosine receptor of 35.6 to 229. Thus, the ratio of $A_3$ to $A_1$ adenosine receptor selectivities for human as compared to mouse adenosine receptors observed for 2-alkynyl, $N^6$-3-chlorobenzyl analogs of the invention ranged from about 1.4 to 5.7. The 2-iodo, $N^6$-3-chlorobenzyl derivative 1 and the 2-iodo, 2,5-dimethoxybenzyl derivative 2 exhibited $K_i$ values at the human $A_3$ adenosine receptor of 3.6 nM and 1.3, respectively, with $A_3/A_1$ adenosine receptor selectivities of 610 and 2360, respectively, while the ratio of $A_3/A_1$ adenosine receptor selectivities observed in human versus mouse adenosine receptors was 12.1 and 3.4, respectively. Compounds 12, 13, 14, 17-20, 31, 37, and 40 exhibited $K_i$ values at the human $A_3$ AR of about 2 nM or less with selectivities up to about 1900 for the human $A_3$ AR vs the human $A_1$ AR.

By way of contrast, the 2-chloro, $N^6$-3-chlorobenzyl analog 13 exhibited $A_3/A_1$ adenosine receptor selectivity for human adenosine receptors that was 87 times greater than observed with mouse adenosine receptors, and exhibited only a 10.3-fold selectivity for $A_3$ versus $A_1$ adenosine receptors for mouse adenosine receptors.

The compounds of formula I provide an advantage that functionalized congeners can be prepared from these compounds. For example, starting from the amine or carboxyl end of $R^2$, various moieties can be attached covalently. Thus, for example, carriers can be covalently attached for enhancing drug delivery. Dendrimers, e.g., PAMAM polyamine dendrimers, such as G3 dendrimers, can be covalently attached to provide multivalent binding. Reporter groups or moieties can be attached for probing distal interactions with adenosine receptors. Spectroscopic probes such as fluorescent probes, ESR probes, or NMR probes can be covalently linked to the amine or carboxyl ends. Other pharmacophores may be covalently linked to the amine or carboxyl ends so that dual acting drugs can be produced, example, an $A_1$ AR agonist can be linked to an $A_3$ AR agonist or a $P2Y_1$, $P2Y_2$, $P2Y_4$, $P^2Y_6$, or $P2Y_{11}$ agonist, an M1 receptor antagonist, or an $A_1$ AR antagonist can be linked to an $A_3$ AR agonist. The amine or carboxyl ends could also be covalently linked to amino acids, peptides, nucleic acids, glycosides, and one or more small molecules. Examples of other probes include opioid receptor probes. Examples of fluorescent probes are BODIPY and FITC. Cy3B is another example of a cyanine dye.

In accordance with an embodiment, the present invention also provides compounds of formula (II):

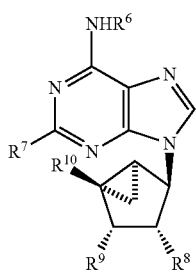

Formula II wherein:
$R^6$ is $C_6$-$C_{14}$ aryl $C_1$-$C_6$ alkyl wherein the $C_6$-$C_{14}$ aryl is substituted with a group represented by C≡C—$(CH_2)_n$—$COR^{11}$ wherein $R^{11}$ is selected from the group consisting of OH, $OR^{12}$, $NR^{13}R^{14}$, wherein $R^{12}$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl;
$R^{13}$ and $R^{14}$ are independently selected from the group consisting of hydrogen, $C_1$-$C_6$ alkyl, and $(CH_2)_nR^{15}$ wherein $R^{15}$ is $NR^{16}R^{17}$, wherein $R^{16}$ and $R^{17}$ are independently selected from the group consisting of hydrogen, $C_1$-$C_6$ alkyl, and $COR^{18}$ wherein $R^{18}$ is hydrogen or $C_1$-$C_6$ alkyl; wherein n is an integer from 1 to 10;
$R^7$ is selected from the group consisting of bromo, chloro, iodo, $C_1$-$C_{20}$ alkyl, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, or aryl portion of $R^7$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkylaminocarbonyl, aminoalkylaminocarbonyl, trialkylsilyl, and any combination thereof;
$R^8$ and $R^9$ are independently selected from the group consisting of hydroxyl, amino, thiol, ureido, $C_1$-$C_6$ alkyl carbonylamino, hydroxy $C_1$-$C_6$ alkyl, and hydrazinyl; and
$R^{10}$ is selected from the group consisting of $C_1$-$C_3$ alkyl aminocarbonyl, di($C_1$-$C_3$ alkyl)aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl;
or a pharmaceutically acceptable salt thereof, with the proviso that when $R^7$ is chloro, $R^8$ and $R^9$ are hydroxyl, and $R^{10}$ is methylaminocarbonyl, $R^6$ is not 3-(3-hydroxypropynyl) benzyl.

In a further embodiment, $R^6$ is benzyl substituted with C≡C—$(CH_2)_n$—$COR^{11}$, wherein n is as defined herein. Preferably, $R^{11}$ is selected from the group consisting of OH, $OR^{12}$, and $NR^{13}R^{14}$. When $R^{11}$ is $OR^{12}$, preferably $R^{12}$ is $C_1$-$C_6$ alkyl.

In another embodiment, $R^{11}$ is $NR^{13}R^{14}$. In a further embodiment, $R^{13}$ and $R^{14}$ are both hydrogen. In another embodiment $R^{13}$ is hydrogen and $R^{14}$ is $(CH_2)_nR^{15}$ wherein $R^{15}$ is $NR^{16}R^{17}$, wherein $R^{16}$ and $R^{17}$ are independently selected from the group consisting of hydrogen, $C_1$-$C_6$ alkyl, and $COR^{18}$ wherein $R^{18}$ is hydrogen or $C_1$-$C_6$ alkyl, and wherein n is defined herein.

In any of the embodiments of Formula II, $R^7$ is preferably selected from the group consisting of chloro, bromo, iodo, $C_1$-$C_{20}$ alkynyl, $C_7$-$C_{12}$ cycloalkyl $C_1$-$C_{20}$ alkynyl, $C_7$-$C_{12}$ bicycloalkyl $C_1$-$C_{20}$ alkynyl, $C_7$-$C_{12}$ bicycloalkenyl $C_1$-$C_{20}$ alkynyl, and $C_6$-$C_{14}$ aryl $C_1$-$C_{20}$ alkynyl. More preferably, $R^7$ is selected from the group consisting of chloro, bromo, and iodo.

In any of the embodiments of Formula II, $R^8$ and $R^9$ are preferably independently selected from the group consisting of hydroxyl, amino, thiol, and ureido, and more preferably $R^8$ and $R^9$ are hydroxyl.

In any of the embodiments of Formula II, $R^{10}$ is preferably selected from the group consisting of $C_1$-$C_3$ alkyl aminocarbonyl, di($C_1$-$C_3$ alkyl)aminocarbonyl, $C_1$-$C_3$ alkylthio $C_1$-$C_3$ alkyl, halo $C_1$-$C_3$ alkyl, amino $C_1$-$C_3$ alkyl, hydroxy $C_1$-$C_3$ alkyl, and $C_3$-$C_6$ cycloalkylamino, more preferably $R^{10}$ is $C_1$-$C_3$ alkyl aminocarbonyl or di($C_1$-$C_3$ alkyl)aminocarbonyl, and even more preferably $R^{10}$ is methylaminocarbonyl.

Specific examples of the compounds of the invention as represented by Formula II are compounds wherein $R^6$ is 3-(5-carboxy-1-pentynyl), $R^7$ is chloro, $R^8$ and $R^9$ are hydroxyl, and $R^{10}$ is methylamino carbonyl; $R^6$ is 3-(5-(2-aminoethyl)aminocarbonyl-1-pentynyl), $R^7$ is chloro, $R^8$ and $R^9$ are hydroxyl, and $R^{10}$ is methylamino carbonyl; and $R^6$ is 3-(5-2-acetamidoethyl)aminocarbonyl-1-pentynyl), $R^7$ is chloro, $R^8$ and $R^9$ are hydroxyl, and $R^{10}$ is methylamino carbonyl.

Among the 2-chloro, 5'-N-methylamide substituted compounds of the invention, the $N^6$-3-(3-hydroxy-1-propynyl) benzyl derivative 16, the $N^6$-3-(5-carboxy-1-pentynyl)benzyl derivative 9, $N^6$-3-(5-(2-aminoethyl)aminocarbonyl-1-pentynyl)benzyl derivative 10, and the $N^6$-3-(5-(2-acetamidoethyl)aminocarbonyl-1-pentynyl)benzyl derivative 11 exhibited $K_i$ values at the human $A_3$ adenosine receptor of 2.9 nM, 17.1 nM, 5.21 nM, and 2.88 nM, respectively, with a selectivity for the human $A_3$ adenosine receptor versus the $A_1$ adenosine receptor of 900, 19, 52, and 63, respectively, while exhibiting K, values at the mouse $A_3$ adenosine receptor of 1.94 nM to 14.4 nM. The ratio of $A_3$ to $A_1$ adenosine receptor selectivities for human as compared mouse adenosine receptors observed for 2-chloro, $N^6$-substituted benzyl compounds of the invention were 0.4 to 15.7. All of the inventive compounds were only weakly active at either human or mouse $A_2$ adenosine receptors. This is compared with the 2-chloro, $N^6$-3-chlorobenzyl analog 13 already discussed herein, which exhibited considerably lower $A_3$ to $A_1$ adenosine receptor selectivity with mouse adenosine receptors and a substantially lower $A_3$ to $A_1$ adenosine receptor selectivity for mouse adenosine receptors as compared to human adenosine receptors.

The compounds of the present invention can be prepared by any suitable method. For example, intermediates 22-25 can be prepared by the method of Tchilibon et al., *J. Med. Chem.*, 2005, 48, 1745-1758. (1'S,2'R,3'S,4'S,5'S)-4'-[6-Chloro-2-iodo-purin-9-yl]-2',3'-isopropylidene-bicyclo [3.1.0]hexane-1'-carboxylic acid ethyl ester (22) is reacted with primary amines to introduce $R^1$ at the $N^6$ position of the purine residue via displacement of chloride. Subsequent amination of the 5' ester group generates an N-alkylamide (e.g., N-methylamide) at the 5' position. Sonogashira alkynylation at the C-2 position introduces $R^2$ wherein $R^2$ is alkynyl. Hydrolysis of the isopropylidene group provides target compounds having $R^2$=alkynyl.

(1'S,2'R,3'S,4'S,5'S)-4'-[2,6-Dichloro-purin-9-yl]-2',3'-isopropylidene-bicyclo[3.1.0]hexane-1'-carboxylic acid methyl ester (24) reacts with 3-iodobenzylamine to introduce a 3-iodobenzylamino group at the $N^6$ position of the purine residue via displacement of chloride. Subsequent amination of the 5' ester group generates an N-alkylamide (e.g., N-methylamide) at the 5' position. Sonogashira alkynylation at the 3-position of the phenyl ring followed by hydrolysis of the isopropylidene group provides target compounds having 3-alkynylated benzylamino groups at $N^6$.

Preparation of aminocarbonylalkynyl derivatives proceeds via (a) Sonogashira coupling using alkoxycarbonylalkynes, followed by aminolysis with diaminoethane, to give amides. 2-(Aminoethyl)aminocarbonylalkyne 10 is acylated with, e.g., acetic anhydride, to provide (2-acetamidoethyl)aminocarbonylalkynyl derivative 11. Compounds 31-44 can be prepared following the reaction scheme described in FIG. 3.

In another aspect, the present invention is predicated on the concept that compounds having a ring constrained substituent or a rigid bicyclo[3.1.0]hexane ring at the 9-position which provides high potency as an antagonist and selectivity to the $A_3$ adenosine receptor, or as a partial agonist of the $A_3$ adenosine receptor, and at the same time lack a substituent on the 4'-position of the bicycle hexane ring.

Accordingly, in accordance with an embodiment, the present invention provides a compound of Formula (III):

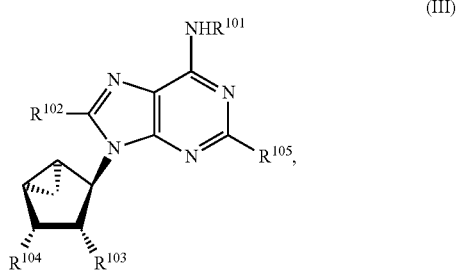

(III)

wherein $R^{101}$ is selected from the group consisting of hydrogen, $C_1$-$C_6$ alkyl, $C_1$-$C_6$ alkoxy, hydroxyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, $C_1$-$C_6$ alkyl carbonyl, sulfonyl, $C_1$-$C_6$ alkyl sulfonyl, $C_6$-$C_{14}$ aryl sulfonyl, heterocyclyl $C_1$-$C_6$ alkyl, heterocyclyl, heteroaryl $C_1$-$C_6$ alkyl, 4-[[[4-[[[(2-amino $C_1$-$C_6$ alkyl)amino]-carbonyl]-$C_1$-$C_6$ alkyl]aniline]carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R^{101}$ is optionally substituted with one or more substituents selected from the group consisting of halo, amino, hydroxyl, carboxy, $C_1$-$C_6$ alkoxycarbonyl, aminocarbonyl, $C_1$-$C_6$ alkylaminocarbonyl, $C_1$-$C_6$ dialkyl aminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and C≡C—$(CH_2)_n$—$COR^{107}$ wherein $R^{107}$ is selected from the group consisting of OH, $OR^{108}$, and $NR^{109}R^{110}$, wherein $R^8$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ and diaryl $C_1$-$C_6$ alkyl; and $R^{109}$ and $R^{110}$ are independently selected from the group consisting of hydrogen, $C_1$-$C_6$ alkyl, and $(CH_2)_nR^{11}$ wherein $R^{111}$ is $NR^{112}R^{113}$, wherein $R^{112}$ and $R^{113}$ are independently selected from the group consisting of hydrogen, $C_1$-$C_6$ alkyl, and $COR^{114}$ wherein $R^{114}$ is hydrogen or $C_1$-$C_6$ alkyl; wherein n is an integer from 1 to 10; and the alkyl or cycloalkyl portion of $R^{101}$ is optionally substituted with one or more substituents selected from the group consisting of halo, amino, $C_1$-$C_6$ alkyl, $C_1$-$C_6$ alkoxy, $C_6$-$C_{14}$ aryloxy, $C_1$-$C_6$ hydroxyalkyl, $C_2$-$C_6$ hydroxyalkenyl, $C_2$-$C_6$ hydroxy alkynyl, aminocarbonyl $C_1$-$C_6$ alkoxy, and $C_6$-$C_{14}$ aryl $C_1$-$C_6$ alkoxy;

$R^{102}$ is selected from the group consisting of hydrogen, halo, amino, hydrazido, mercapto, $C_1$-$C_{20}$ alkylamino, $C_6$-$C_{14}$ aryl amino, $C_6$-$C_{14}$ aryloxy, $C_1$-$C_{20}$ alkyl, $C_1$-$C_{20}$ alkoxy, $C_1$-$C_{20}$ thioalkoxy, pyridylthio, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, —C≡C—(CH$_2$)$_m$—C(=O)—O—$C_1$-$C_6$ alkyl, —C≡C—(CH$_2$)$_m$—C(=O)—NH—(CH$_2$)$_m$—NH$_2$, —C≡C—(CH$_2$)$_m$—$C_1$-$C_6$ alkyl, —C≡C—(CH$_2$)$_m$-aryl, wherein m and n are independently 1 to 10, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, or aryl portion of $R^{102}$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkyl aminocarbonyl, aminoalkyl aminocarbonyl, and trialkylsilyl;

$R^{103}$ and $R^{104}$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^{105}$ is selected from the group consisting of hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

In accordance with an embodiment of the invention, $R^{101}$ is selected from the group consisting of $C_6$-$C_{14}$ aryl $C_1$-$C_6$ alkyl and $C_6$-$C_{14}$ aryl $C_3$-$C_8$ cycloalkyl, wherein the aryl portion of $R^{101}$ is optionally substituted with one or more substituents selected from the group consisting of halo, amino, $C_1$-$C_6$ alkyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkoxy, and $C_6$-$C_{14}$ aryl $C_1$-$C_6$ alkoxy; and in a particular embodiment, $R^{101}$ is selected from the group consisting of benzyl, phenyl cyclopropyl, or 1-naphthyl methyl, wherein the phenyl or naphthyl portion of $R^{101}$ is optionally substituted with one or more substituents selected from the group consisting of halo, amino, hydroxyl, carboxy, alkoxycarbonyl, aminocarbonyl, alkylaminocarbonyl, dialkyl aminocarbonyl, $C_1$-$C_6$ alkyl, $C_1$-$C_6$ alkoxy, phenoxy, hydroxy $C_1$-$C_6$ alkyl, hydroxy $C_2$-$C_6$ alkenyl, and hydroxy $C_2$-$C_6$ alkynyl.

In a specific embodiment of the invention, $R^{101}$ is benzyl, phenyl cyclopropyl, or 1-naphthyl methyl, wherein the phenyl or naphthyl portion of $R^{101}$ is optionally substituted with one or more substituents selected from the group consisting of halo, hydroxyl, and alkoxy. Examples of $R^{101}$ are benzyl and benzyl substituted with one or more substituents selected from the group consisting of halo and $C_1$-$C_6$ alkoxy.

In any of the embodiments above, $R^{101}$ is selected from the group consisting of 3-chlorobenzyl, 3-bromobenzyl, 3-iodobenzyl, 2-hydroxy-5-methoxy-benzyl, and 2,5-dimethoxybenzyl. In an embodiment, the phenyl cyclopropyl is trans-2-phenyl-1-cyclopropyl.

In any of the embodiments above, $R^{102}$ is halo, specifically chloro, bromo, or iodo, or $R^2$ is —C≡C—(CH$_2$)$_m$—CH$_3$, —C≡C—(CH$_2$)$_m$-aryl, —C≡C—(CH$_2$)$_m$—C(=O)—O—CH$_3$, —C≡C—(CH$_2$)$_m$—C(=O)—NH—(CH$_2$)$_n$—NH$_2$, wherein m and n are independently 1 to 10, where in certain embodiments m and n are 2 to 6, and in certain other embodiments m and n are 3 to 5, and wherein the CH$_3$ or aryl group is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkyl aminocarbonyl, aminoalkyl aminocarbonyl, and trialkylsilyl; or a pharmaceutically acceptable salt thereof.

In any of the embodiments above, $R^{103}$ and $R^{104}$ are particularly hydroxyl.

In any of the embodiments above, $R^{105}$ is particularly hydrogen.

The term "one or more substituents" in any of the embodiments of the invention refers to 1, 2, 3, 4, or more substituents.

Particular examples of compounds of the invention are those wherein $R^{102}$ is chloro, $R^{101}$ is 3-chlorobenzyl, 3-iodobenzyl, 3-bromobenzyl, 1-naphthylmethyl, 2,5-dimethoxybenzyl, 2-hydroxy-5-methoxybenzyl, or trans-2-phenyl-cyclopropyl, $R^{103}$ and $R^{104}$ are hydroxyl, and $R^{105}$ is hydrogen.

Many of the compounds described above have antagonistic as well as partial agonistic properties at the A$_3$ adenosine receptor, depending upon the parameter studied. The definition of antagonist or agonist is highly dependent upon the cell system and the parameter studied, receptor density, species, and the like.

Figure 4:
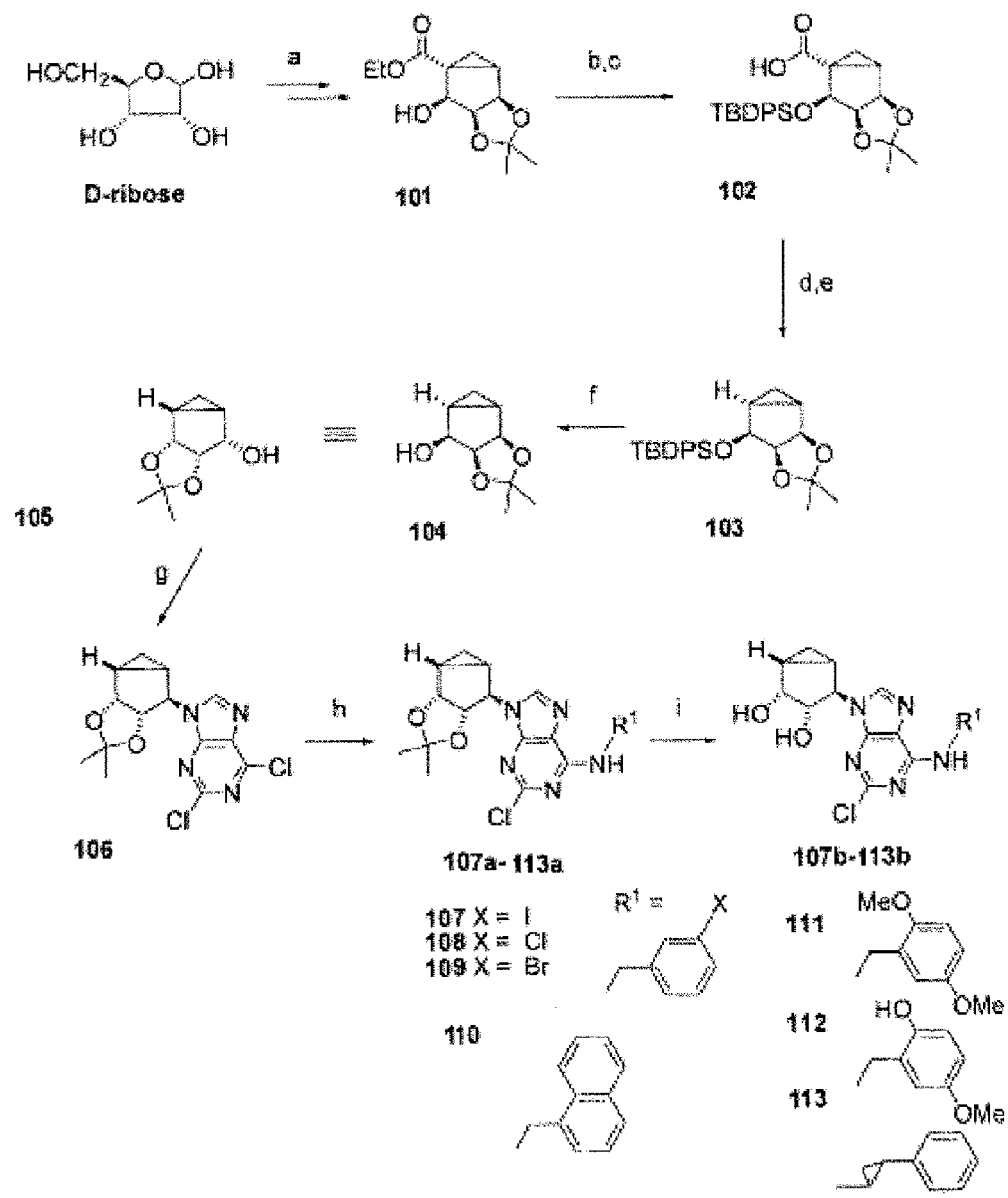
FIG. 4 depicts a reaction scheme to prepare compounds 107b-113b in accordance with an embodiment of the invention. a) 7 steps (see Joshi et al. *Nucleosides, Nucleotides, and Nucleic Acids* 2008, 27, 279 and Joshi et al. *J. Org. Chem.* 2005, 70, 439); b) TBDPS-Cl, imidazole, DMF; c) NaOH, H$_2$O, MeOH, reflux; d) 2-mercaptopyridine N-oxide, DCC, toluene; e) (Me$_3$Si)$_3$SiH, AIBN, toluene; f) Bu$_4$NF, THF; g) 2,6-dichloropurine, PPh$_3$, DIAD, THF; h) RNH$_2$, EtOH; i) TFA/H$_2$O/MeOH.
Figure 5:
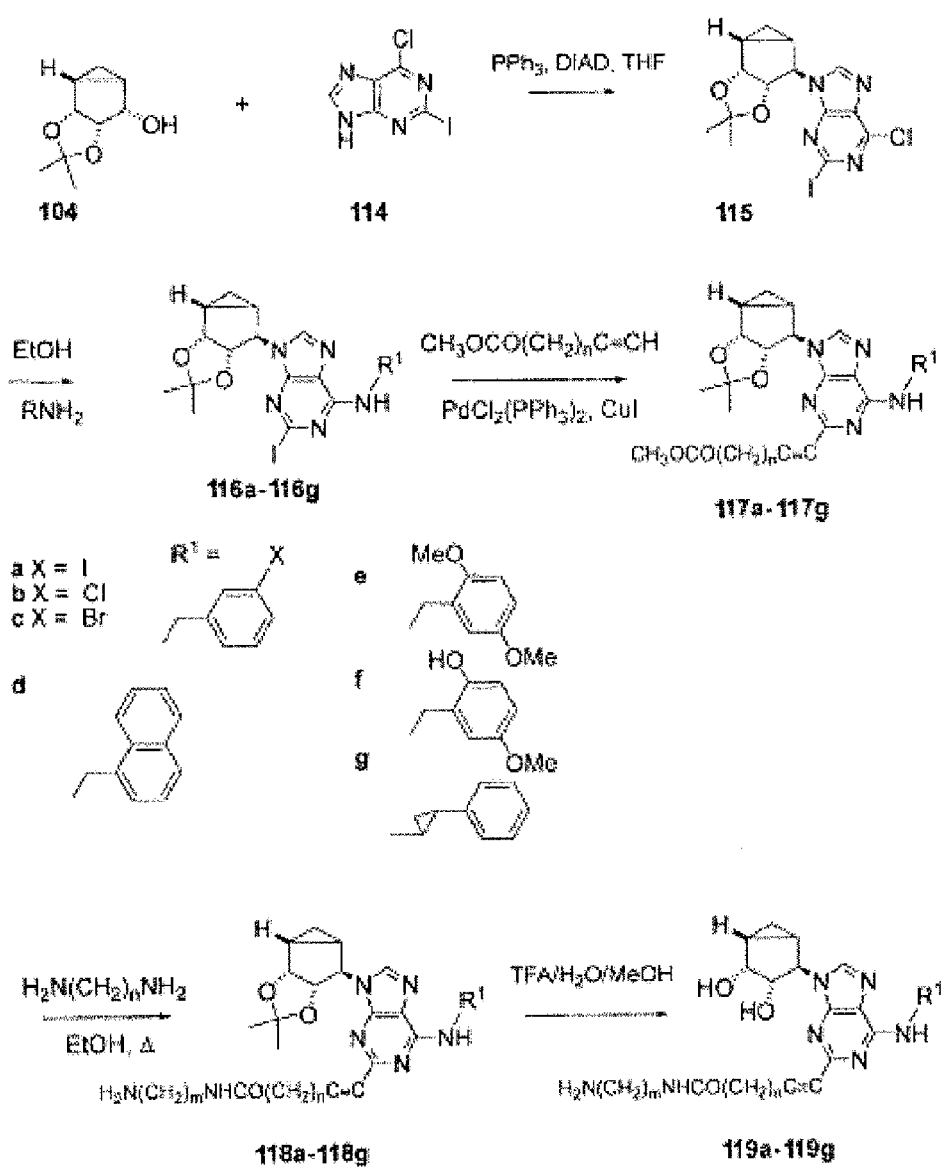
FIG. 5 depicts a reaction scheme to prepare compounds 119a-119g in accordance with an embodiment of the invention.
Figure 6:
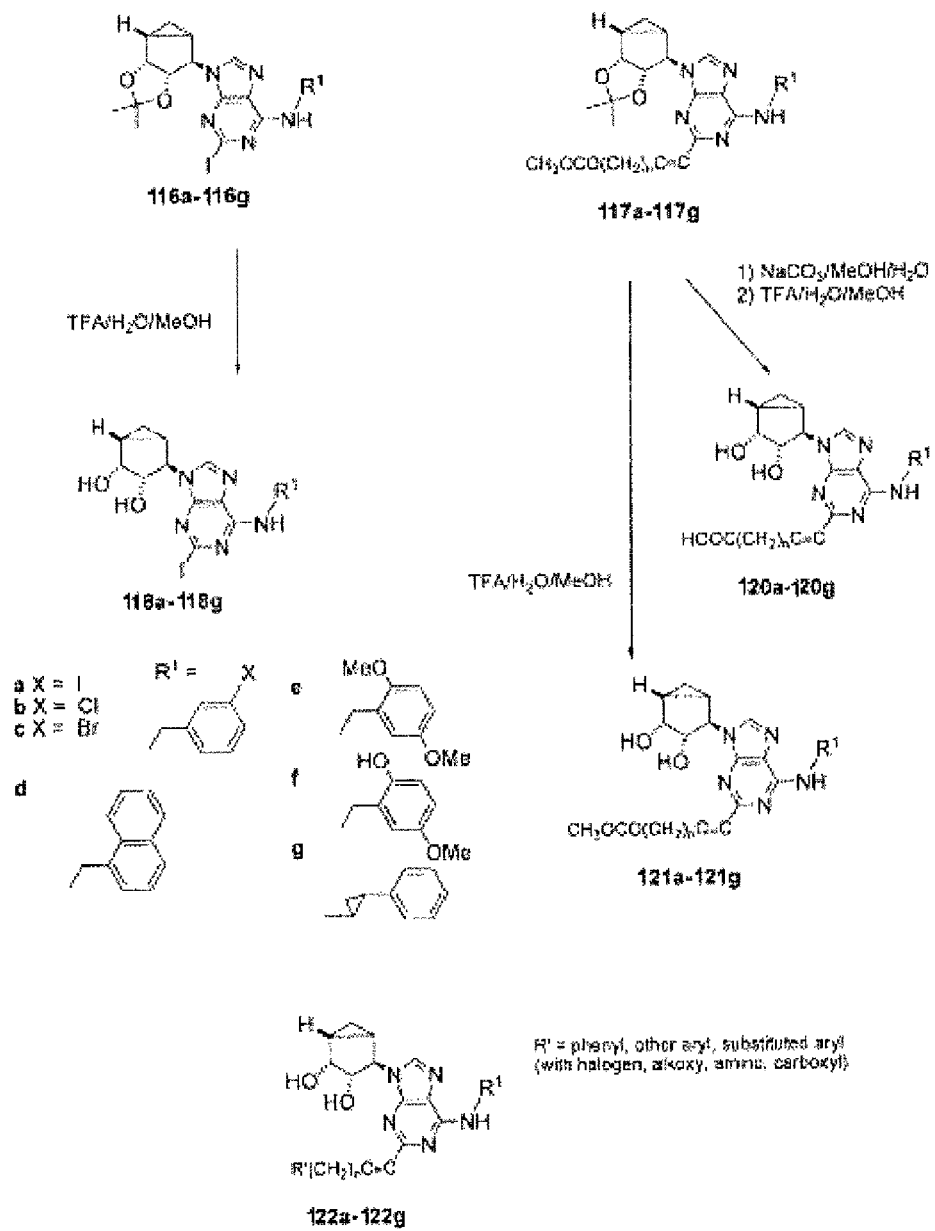
FIG. 6 depicts compounds 122a-122g in accordance with an embodiment of the invention and reaction schemes to prepare compounds 120a-120g and 121a-121g.

The compounds of the invention can be prepared by any suitable method. For example, FIG. 4 illustrates a method of preparing compounds 107b-113b. FIG. 5 illustrates a method of preparing compounds 119a-119g. FIG. 6 illustrates a method of preparing compounds 120a-120g and 121a-121g.

The present invention provides a method for activating A$_3$ adenosine receptors in a cell comprising contacting the cell with an effective amount of one or more of the inventive compounds or a pharmaceutically acceptable salt thereof. The contacting can be in vitro or in vivo. When the contacting is done in vitro, the contacting can be done by any suitable method, many of which are known in the art. For example, the cell can be provided in a culture medium and the inventive compound introduced into the culture medium per se, or as a solution of the compound in an appropriate solvent.

The present invention provides a method of selectively activating A$_3$ adenosine receptors in a mammal, which method comprises administering to a mammal in need of selective activation of its A$_3$ adenosine receptors a therapeutically effective amount, including a prophylactically effective amount, of one or more of the inventive compounds or a pharmaceutically acceptable salt(s) thereof which binds with the A$_3$ receptor so as to stimulate an A$_3$ receptor-dependent response. The compound can be administered acutely or chronically.

In some embodiments, the invention also provides a method for selectively inactivating an A$_3$ adenosine receptor, or partially activating an A$_3$ adenosine receptor, in as animal in need thereof, comprising administering to the mammal an effective amount of a compound or pharmaceutically acceptable salt of the invention. The methods of the invention can be applied to any suitable mammal, particularly human.

In some embodiments, the present invention further provides a method for inactivating A$_3$ adenosine receptors, or partially activating such a receptor, in a cell comprising contacting the cell with an effective amount of one or more of the inventive compounds or a pharmaceutically acceptable salt thereof. The contacting can be in vitro or in vivo. When the contacting is done in vitro, the contacting can be done by any suitable method, many of which are known in the art. For example, the cell can be provided in a culture medium and the inventive compound introduced into the culture medium per se, or as a solution of the compound in an appropriate solvent.

The mammal can be any suitable mammal and typically is a human, a mouse, or a rat. Desirably, the inventive compounds exhibit A$_3$/A$_1$ adenosine receptor selectivity that is less than about 10:1 when determined using human and mouse adenosine receptors.

The method of the present invention has particular usefulness in in vivo applications. For example, A$_3$ adenosine receptor agonists can be used in the treatment of any disease state or condition involving the release of inositol-1,4,5-triphosphate (IP3), diacylglycerol (DAG), and free radicals and subsequent arachidonic acid cascades. Thus, high blood pressure, locomotor hyperactivity, hypertension, acute hypoxia, depression, and infertility can be treated in accordance with the present inventive method, wherein one of the above-described compounds is acutely administered, e.g., within about a few minutes to about an hour of the onset or realization of symptoms. The method also has utility in the treatment of chronic disease states and conditions, in particular those conditions and disease states wherein chronic prophylactic or therapeutic administration of one of the above-described compounds will prevent the onset of symptoms or will reduce recovery time. Examples of disease states and conditions that may be chronically treated in accordance with the present inventive method include inflammatory disorders, such as vascular inflammation and arthritis, allergies, asthma, wound healing, stroke, cardiac failure, acute spinal cord injury, acute head injury or trauma, seizure, neonatal hypoxia (cerebral palsy; prophylactic treatment involves chronic exposure through placental circulation), chronic hypoxia due to arteriovenous malformations and occlusive cerebral artery disease, ischemia and reperfusion injury in skeletal muscle, severe neurological disorders related to excitotoxicity, Parkinson's disease, Huntington's chorea, and other diseases of the CNS, cardiac disease, kidney disease, and contraception.

The present invention further provides a method of cardioprotection for preventing or reducing ischemic damage to the heart in an animal in need thereof comprising administering to the animal a compound or salt as described above, particularly, a compound or salt of formula I, wherein $R^{101}$ is 3-bromobenzyl or 3-iodobenzyl, $R^{102}$ is halo, $R^{103}$ and $R^{104}$ are hydroxyl, and $R^{105}$ is hydrogen.

In accordance with another embodiment, the invention provides isotopically labeled versions of the compounds described above, for example, compounds labeled with a radioactive or non-radioactive isotope, for use in the determination of drug/tissue distribution assays, in the manipulation of oxidative metabolism via the primary kinetic isotope effect, in identifying potential therapeutic agents for the treatment of diseases or conditions associated with target-receptor mediation. The compounds of the invention can be prepared with a radioactive isotope. Any suitable atom can be replaced with a radioactive isotope, for example, a carbon atom, hydrogen atom, a halogen atom, a sulfur atom, nitrogen atom, or an oxygen atom can be replaced with a corresponding isotope. Thus, for example, a halogen atom can be replaced with $^{18}F$, $^{36}Cl$, $^{75}Br$, $^{76}Br$, $^{77}Br$, $^{82}Br$, $^{122}I$, $^{123}I$, $^{125}I$, or $^{131}I$. The use of radiolabeled compounds that may be detected using imaging techniques, such as the Single Photon Emission Computerized Tomography (SPECT), Magnetic Resonance Spectroscopy (MRS), or the Positron Emission Tomography (PET), are known in the art. See, for example, U.S. Pat. Nos. 6,395,742 and 6,472,667.

In accordance with a further embodiment, the invention provides a radiolabeled compound of Formula IV:

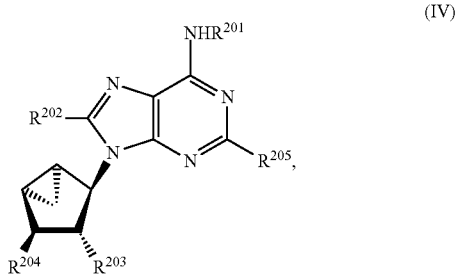

(IV)

wherein $R^{201}$ is selected from the group consisting of $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, $C_6$-$C_{14}$ aryl sulfonyl, heterocyclyl $C_1$-$C_6$ alkyl, heterocyclyl, heteroaryl $C_1$-$C_6$ alkyl, 4-[[[4-[[[(2-amino $C_1$-$C_6$ alkyl)amino]-carbonyl]-$C_1$-$C_6$ alkyl]aniline]carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R^{201}$ is substituted with one or more halogen atoms that are radioactive;

$R^{202}$ is selected from the group consisting of hydrogen, halo, amino, hydrazido, mercapto, $C_1$-$C_{20}$ alkylamino, $C_6$-$C_{14}$ aryl amino, $C_6$-$C_{14}$ aryloxy, $C_1$-$C_{20}$ alkyl, $C_1$-$C_{20}$ alkoxy, $C_1$-$C_{20}$ thioalkoxy, pyridylthio, $C_7$-$C_{12}$ cycloalkyl $C_1$-$C_{20}$ alkyl, $C_7$-$C_{12}$ bicycloalkyl $C_1$-$C_{20}$ alkyl, $C_7$-$C_{12}$ bicycloalkenyl $C_1$-$C_{20}$ alkyl, $C_6$-$C_{14}$ aryl $C_1$-$C_{20}$ alkyl, $C_2$-$C_{20}$ alkenyl, $C_7$-$C_{12}$ cycloalkyl $C_2$-$C_{20}$ alkenyl, $C_7$-$C_{12}$ bicycloalkyl $C_2$-$C_{20}$ alkenyl, $C_7$-$C_{12}$ bicycloalkenyl $C_2$-$C_{20}$ alkenyl, $C_6$-$C_{14}$ aryl $C_2$-$C_{20}$ alkenyl, $C_2$-$C_{20}$ alkynyl, carboxy alkyl $C_2$-$C_{20}$ alkynyl, —C≡C—$(CH_2)_m$—C(=O)—O—$C_1$-$C_6$ alkyl, —C≡C—$(CH_2)_m$—C(=O)—NH—$(CH_2)_m$—$NH_2$, —C≡C—$(CH_2)_m$—$C_1$-$C_6$ alkyl, —C≡C—$(CH_2)_m$-aryl, wherein m and n are independently 1 to 10, $C_7$-$C_{12}$ cycloalkyl $C_2$-$C_{20}$ alkynyl, $C_7$-$C_{12}$ bicycloalkyl $C_2$-$C_{20}$ alkynyl, $C_7$-$C_{12}$ bicycloalkenyl $C_2$-$C_{20}$ alkynyl, $C_6$-$C_{14}$ aryl $C_2$-$C_{20}$ alkynyl, and the alkyl, cycloalkyl, or aryl portion of $R^{202}$ is optionally substituted with one or more substituents selected from the group consisting of halo, hydroxyl, amino, alkylamino, dialkylamino, sulfur, carboxy, alkoxycarbonyl, aminocarbonyl, alkylaminocarbonyl, dialkyl aminocarbonyl, aminoalkyl aminocarbonyl, and trialkylsilyl;

$R^{203}$ and $R^{204}$ are independently selected from the group consisting of hydroxyl, amino, thiol, ureido, $C_1$-$C_6$ alkyl carbonylamino, hydroxy $C_1$-$C_6$ alkyl, and hydrazinyl; and $R^{205}$ is selected from the group consisting of hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

The halogen atom of the radiolabeled compound or salt in $R^{201}$ of the invention can be any suitable isotope, for example, $^{18}F$, $^{76}Br$, or $^{125}I$, preferably $^{76}Br$ or $^{125}I$.

In a particular embodiment, the invention provides radiolabeled compounds or salts wherein $R^{201}$ is 3-bromobenzyl or 3-iodobenzyl, $R^{202}$ is halo, $R^{203}$ and $R^{204}$ are hydroxyl, and $R^{205}$ is hydrogen.

Accordingly, the present invention further provides a method of diagnostic imaging of an $A_3$ adenosine receptor in a tissue or organ of an animal comprising administering an effective amount of a radiolabeled compound or salt as described above to the animal and obtaining an image of the organ or tissue of the animal. The image can be obtained by any suitable imaging technique, for example, SPECT, MRS, and/or PET.

The present invention also provides a diagnostic method for determining a treatment of a patient for a possible agonist or antagonist of the $A_3$ adenosine receptors, the treatment comprising:

(a) administering a radiolabeled compound or salt as described above;

(b) obtaining a biological sample from the patient;

(c) determining the level of expression of the $A_3$ adenosine receptor;

(d) comparing the level of expression of the receptor to that of a normal population; and (e) if the patient's level of expression is higher than that of the normal population, determining a treatment regimen comprising administering an agonist or antagonist of the adenosine receptor whose expression was higher in the patient than that of the normal population.

In accordance with a further embodiment, the invention provides a compound of formula (V):

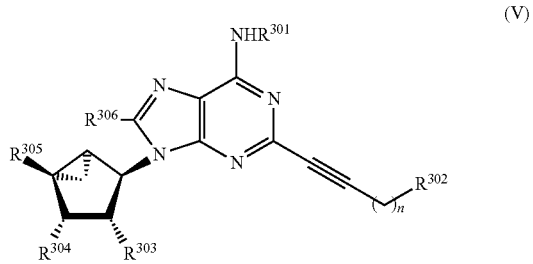

$R^{301}$ is selected from the group consisting of $C_1$-$C_6$ alkyl, $C_1$-$C_6$ alkoxy, hydroxyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl)amino]-carbonyl]-$C_1$-$C_6$ alkyl]aniline]carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R^{301}$ is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof; and the alkyl or cycloalkyl portion of $R^{301}$ is optionally substituted with one or more substituents selected from the group consisting of halo, amino, alkyl, alkoxy, aryloxy, hydroxyalkyl, hydroxyalkenyl, hydroxyalkynyl, aminocarbonylalkoxy, and arylalkoxy, and any combination thereof;

$R^{302}$ is $C_6$-$C_{16}$ aryl or heteroaryl; and the aryl or heteroaryl group is optionally substituted with one or more substituents selected from the group consisting of halo, amino, alkyl, aryl, carboxyl, sulfonyloxy, carboxyalkyl, sulfonyloxyalkyl, alkylcarbonyl, arylcarbonyl, and any combination thereof;

$R^{303}$ and $R^{304}$ are independently selected from the group consisting of hydroxyl, amino, mercapto, ureido, $C_1$-$C_6$ alkyl carbonylamino, hydroxy $C_1$-$C_6$ alkyl, and hydrazinyl; and $R^{305}$ is selected from the group consisting of hydrogen, $C_1$-$C_3$ alkyl aminocarbonyl, di($C_1$-$C_3$ alkyl)aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl;

$R^{306}$ is selected from the group consisting of hydrogen, $C_1$-$C_6$ alkyl, $C_2$-$C_6$ alkenyl, $C_2$-$C_6$ alkynyl, heteroaryl, and $C_1$-$C_6$ aminoalkyl;

n is 0-6;

or a pharmaceutically acceptable salt hereof.

In a preferred embodiment, $R^{306}$ is hydrogen.

In certain preferred embodiments, $R^{305}$ is selected from the group consisting of $C_1$-$C_3$ alkyl aminocarbonyl or di($C_1$-$C_3$ alkyl)aminocar bonyl.

In certain preferred embodiments, $R^{303}$ and $R^{304}$ are both hydroxyl.

In any of the above embodiments, $R^{301}$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, heterocyclyl $C_1$-$C_6$ alkyl, heterocyclyl, and $C_6$-$C_{14}$ aryl $C_3$-$C_8$ cycloalkyl, wherein the aryl or heterocyclyl portion of $R^{301}$ is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof; and the alkyl or cycloalkyl portion of $R^{301}$ is optionally substituted with one or more substituents selected from the group consisting of halo, amino, alkyl, alkoxy, arylalkoxy, hydroxyalkyl, hydroxyalkenyl, hydroxyalkynyl, aminocarbonylalkoxy, and arylalkoxy, and any combination thereof.

In certain preferred embodiments, $R^{301}$ is selected from the group consisting of $C_1$-$C_6$ alkyl, $C_3$-$C_8$ cycloalkyl, $C_3$-$C_8$ cycloalkyl $C_1$-$C_6$ alkyl, $C_6$-$C_{14}$ aryl $C_1$-$C_6$ alkyl, and heterocyclyl $C_1$-$C_6$ alkyl, wherein the aryl or heterocyclyl portion of $R^{301}$ is optionally substituted with one or more substituents selected from the group consisting of halo, amino, hydroxyl, carboxy, alkoxycarbonyl, aminocarbonyl, alkylaminocarbonyl, dialkylaminocarbonyl, and $C_1$-$C_6$ alkyl, and any combination thereof; and the alkyl or cycloalkyl portion of $R^{301}$ is optionally substituted with one or more substituents selected from the group consisting of halo, amino, alkyl, alkoxy, and aryloxy, and any combination thereof.

In certain more preferred embodiments, $R^{301}$ is $C_1$-$C_6$ alkyl. In certain other preferred embodiments, $R^{301}$ is selected from the group consisting of benzyl, 3-chlorobenzyl, and 3-iodobenzyl.

In any of the above embodiments, $R^{302}$ is $C_6$-$C_{16}$ aryl; and the aryl group is optionally substituted with one or more substituents selected from the group consisting of halo, amino, alkyl, aryl, carboxyl, and sulfonyloxy, and any combination thereof.

In any of the above embodiments, $R^{302}$ is selected from the group consisting of 2-pyridyl, 3-pyridyl, and 4-pyridyl.

In certain particular embodiments, $R^{301}$ is $C_1$-$C_6$ alkyl or 3-chlorobenzyl; $R^{302}$ is $C_6$-$C_{16}$ aryl; and the aryl group is optionally substituted with one or more substituents selected from the group consisting of halo, amino, alkyl, aryl, carboxyl, and sulfonyloxy; $R^{303}$ and $R^{304}$ are both hydroxyl; $R^{305}$ is $C_1$-$C_3$ alkyl aminocarbonyl; $R^{306}$ is hydrogen; and n is 0.

In particular embodiments, the compound is selected from the group consisting of:

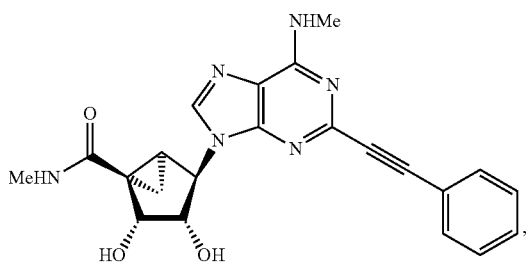

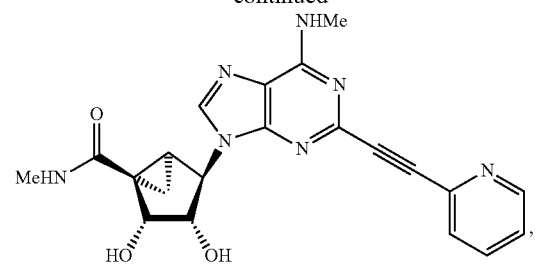
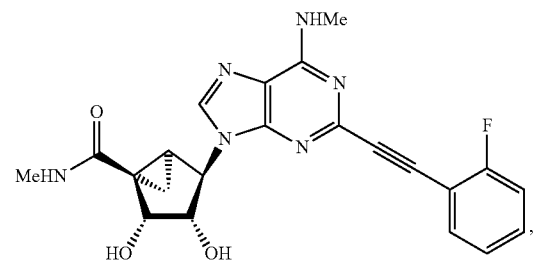
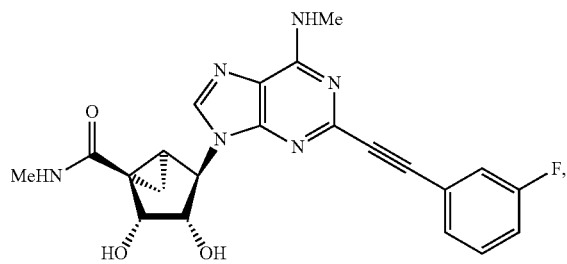
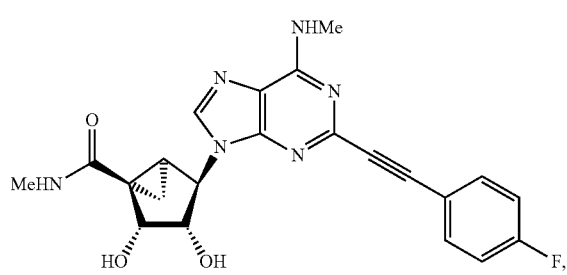
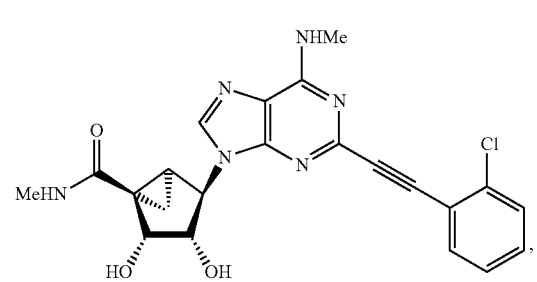
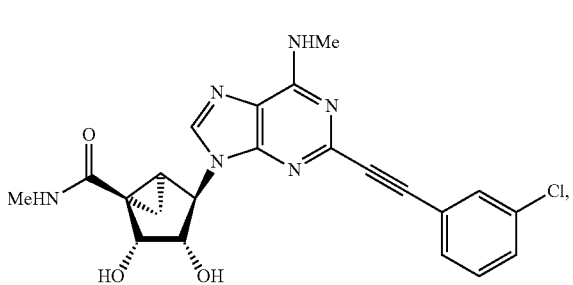
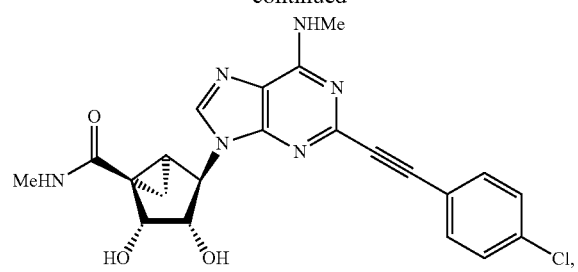
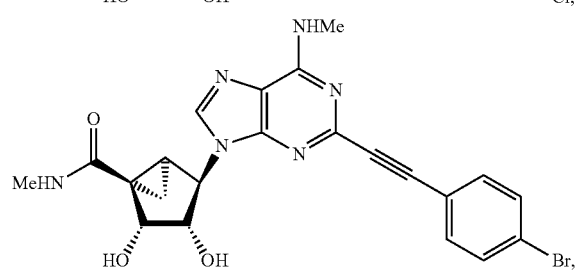
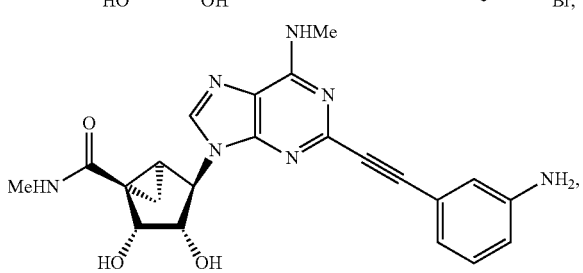
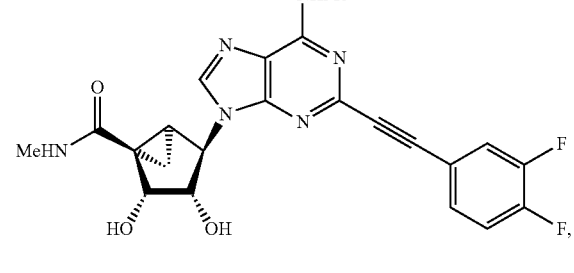
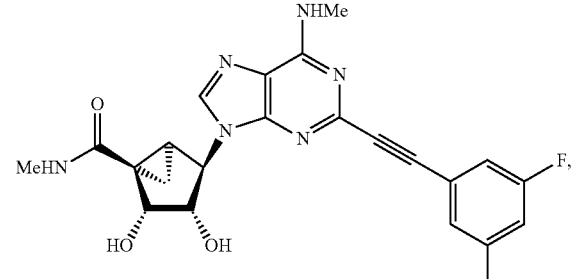
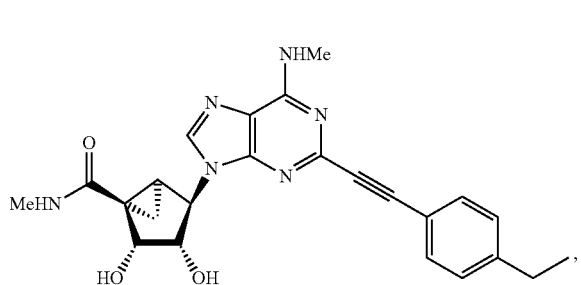

-continued
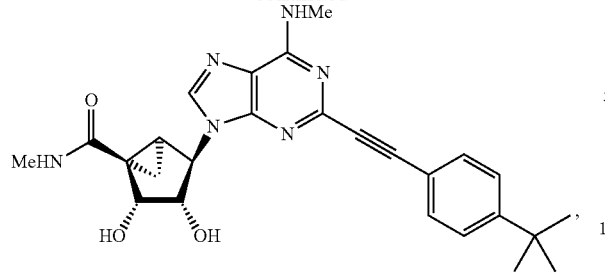,
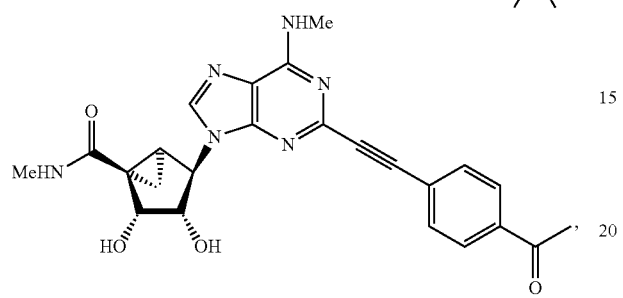,
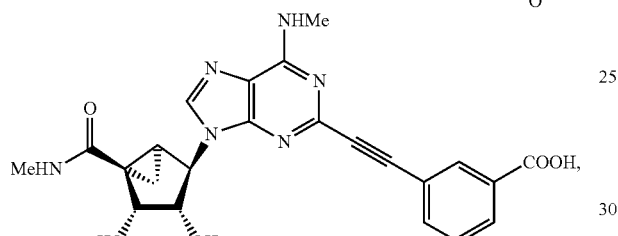,
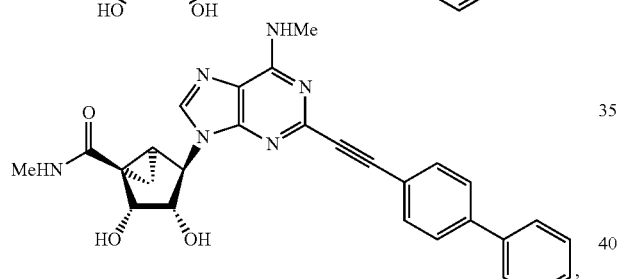,
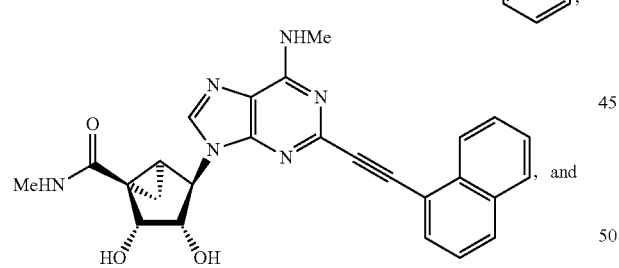, and
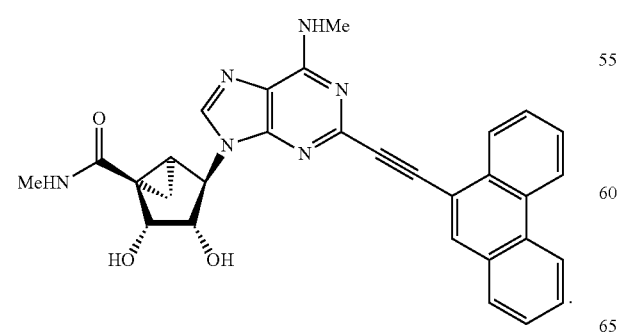.
In particular embodiments, the compound is selected from the group consisting of:

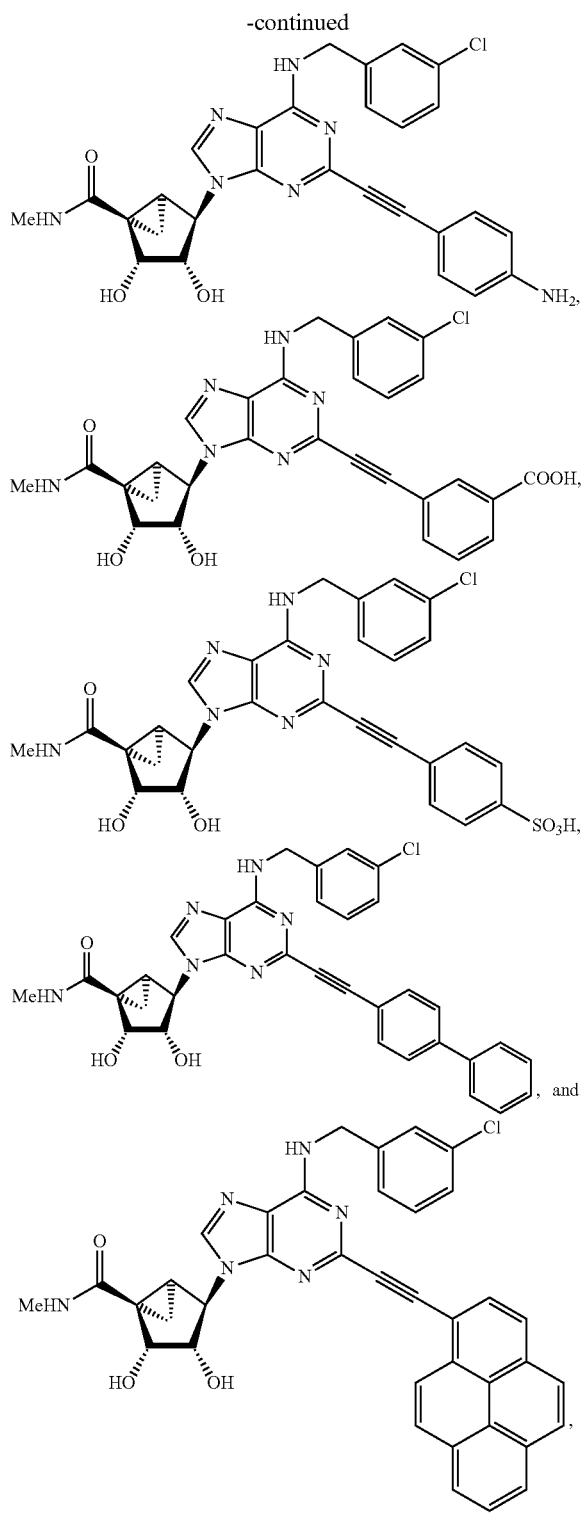

or a pharmaceutically acceptable salt thereof.

In accordance with any of the above formulas, the term "aryl" refers to aromatic moieties such as phenyl, naphthyl, anthracenyl, and biphenyl. The term "heterocyclyl" refers to 3-7 membered rings which can be saturated or unsaturated, comprising carbon and one or more heteroatoms such as O, N, and S, and optionally hydrogen; optionally in combination with one or more aromatic rings. Examples of heterocyclyl groups include pyridyl, piperidinyl, piperazinyl, pyrazinyl, pyrolyl, pyranyl, tetrahydropyranyl, tetrahydrothiopyranyl, pyrrolidinyl, furanyl, tetrahydrofuranyl, thiophenyl, tetrahydrothiophenyl, purinyl, pyrimidinyl, thiazolyl, thiazolidinyl, thiazolinyl, oxazolyl, tetrazolyl, tetrazinyl, benzoxazolyl, morpholinyl, thiophorpholinyl, quinolinyl, and isoquinolinyl. Examples of heteroaryl alkyl include heteroaryl methyl such as 2- or 3-methyl substituted groups, e.g., thienylmethyl, pyridylmethyl, and furylmethyl.

The alkyl, alkoxy, and alkylamino groups can be linear or branched. When an aryl group is substituted with a substituent, e.g., halo, amino, alkyl, hydroxyl, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention.

The term "halo" refers to fluorine, chlorine, bromine, and iodine.

Examples of bicycloalkyls include norbornyl, s-endonorbornyl, carbamethylcylopentyl, and bicyclohexyl. An example of a tricycloalkyl is adamantyl.

When a group is substituted with sulfur, a hydrogen atom of the group is replaced with a sulfur atom or an oxidized sulfur atom. The sulfur atom may be monosubstituted with an alkyl or aryl group to form a thiol group, or may be disubstituted with alkyl and/or aryl groups to form a thioether group. When the sulfur atom is oxidized, the oxidized sulfur atom is a part of sulfoxide group or a sulfone group.

The phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, nonaqueous media such as ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

Examples of pharmaceutically acceptable salts for use in the present inventive pharmaceutical composition include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, maleic and arylsulfonic, for example, benzenesulfonic and p-toluenesulfonic, acids.

The present invention further provides a pharmaceutical composition comprising a compound as described above and a pharmaceutically acceptable carrier. The present invention provides a pharmaceutical composition comprising a pharmaceutically acceptable carrier and an effective amount, e.g., a therapeutically effective amount, including a prophylactically effective amount, of one or more of the aforesaid compounds, or salts thereof, of the present invention.

The pharmaceutically acceptable carrier can be any of those conventionally used and is limited only by chemicophysical considerations, such as solubility and lack of reactivity with the compound, and by the route of administration. It will be appreciated by one of skill in the art that, in addition to the following described pharmaceutical compositions; the compounds of the present invention can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge fauns can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

In certain embodiments, the invention provides a method of treating or preventing a disease, state or condition in a patient in need thereof comprising administering to the patient an effective amount of a compound of any one of embodiments of the invention or a pharmaceutically acceptable salt thereof, wherein the disease, state or condition is selected from the group consisting of vascular inflammation, arthritis, allergies, asthma, wound healing, stroke, cardiac failure, acute spinal cord injury, acute head injury or trauma, seizure, neonatal hypoxia, cerebral palsy, chronic hypoxia due to arteriovenous malformations and occlusive cerebral artery disease, ischemia and reperfusion injury in skeletal muscle, severe neurological disorders related to excitotoxicity, Parkinson's disease, Huntington's chorea, diseases of the CNS, cardiac disease, kidney disease, glaucoma, cancer, neuropathic pain, transient ischemic attacks, myeloprotection, dry eye syndrome, osteoarthritis, rheumatoid arthritis, loss of skin pigmentation, inflammatory bowel disease, pulmonary inflammation, uveitis, and septic shock.

The compounds or salts thereof can be used in any suitable dose. Suitable doses and dosage regimens can be determined by conventional range finding techniques. Generally treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. Typically the dosages range from about 0.001 to about 1000 mg/kg body weight of the animal being treated/day. For example, in embodiments, the compounds or salts may be administered from about 100 mg/kg to about 300 mg/kg, from about 120 mg/kg to about 280 mg/kg, from about 140 mg/kg to about 260 mg/kg, from about 150 mg/kg to about 250 mg/kg, from about 160 mg/kg to about 240 mg/kg, of subject body weight per day, one or more times a day, to obtain the desired therapeutic effect.

Figure 12:
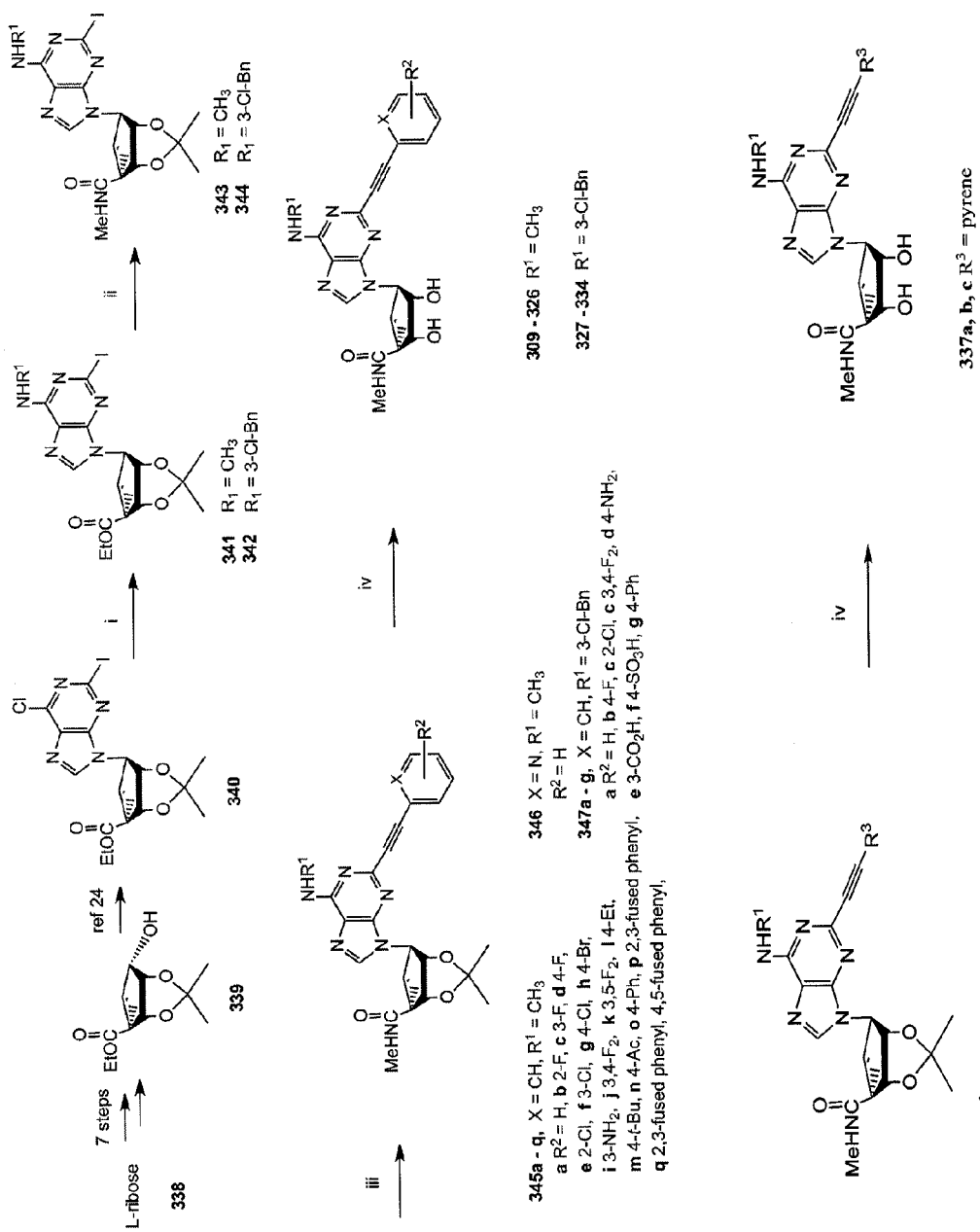
FIG. 12 depicts a reaction scheme for the synthesis of compounds 309-334 in accordance with an embodiment of the invention.

A representative synthetic route used to prepare (N)-methanocarba 5'-N-methyluronamido derivatives containing a 2-arylethynyl group involves a key Sonogashira reaction at a 2-iodoadenine moiety is illustrated in FIG. 12. L-ribose 338 was converted as previously reported into the 2',3'-protected intermediate 339 containing a 5-ethyl ester, which was then subjected to a Mitsunobu reaction with 2-iodo-6-chloropurine to give 340 (Joshi, B. V. et al., *Nucleosides, Nucleotides, and Nucleic Acids*, 2008, 27, 279-291). The N$^6$-methyl or N$^6$-(3-chlorobenzyl) group was added by nucleophilic substitution at room temperature to provide 341 and 342, respectively, followed by aminolysis of the ester at elevated temperature leading to 343 and 344. A Sonogashira reaction was then carried out with a variety of commercially available arylacetylenes to give 343a-m (N$^6$-methyl) and 344a-e (N$^6$-3-chlorobenzyl). Finally, acid hydrolysis of the isopropylidene protecting group provided N$^6$-methyl 309-326 and N$^6$-3-chlorobenzyl 327-334 nucleosides.

Figure 13:
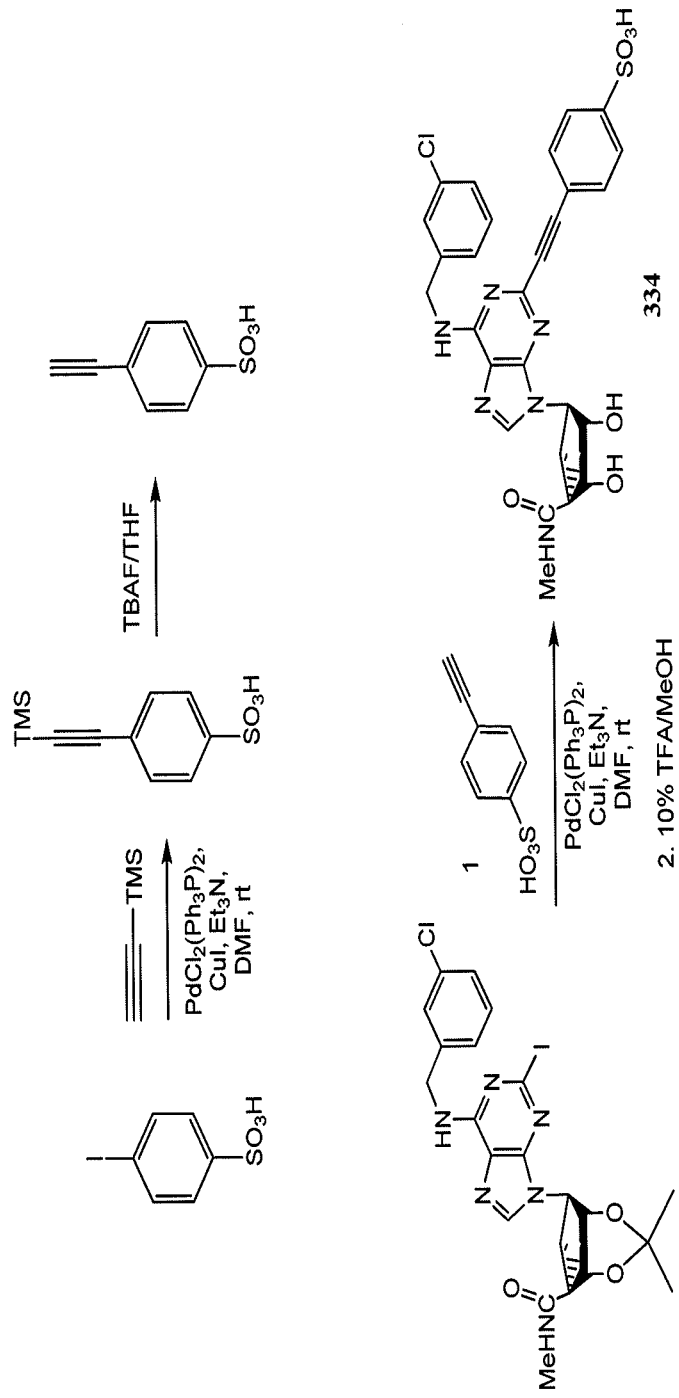
FIG. 13 depicts a reaction scheme for the synthesis of compound 334 in accordance with an embodiment of the invention.

FIGS. 13 and 15 illustrate synthetic routes to compounds 334 and 337b. FIG. 14 illustrates a synthetic route to compounds of formula V wherein R$^5$ is hydrogen.

The following examples further illustrate the invention but, of course, should not be construed as in any way limiting its scope.

L-ribose, and other reagents and solvents were purchased from Sigma-Aldrich (St. Louis, Mo.). $^1$H NMR spectra were obtained with a Varian Gemini 300 spectrometer using CDCl$_3$ and CD$_3$OD as solvents. Chemical shifts are expressed in δ values (ppm) with tetramethylsilane (δ0.00) for CDCl$_3$ and water (δ3.30) for CD$_3$OD. TLC analysis was carried out on aluminum sheets precoated with silica gel F$_{254}$ (0.2 mm) from Aldrich. All target compounds are ≥95% pure as determined by HPLC. HPLC mobile phases consisted of System A: linear gradient solvent system: CH$_3$CN/triethyl ammonium acetate from 5/95 to 60/40 in 20 min, flow rate 1.0 mL/min; System B: linear gradient solvent system: CH$_3$CN/tetrabutyl ammonium phosphate from 20/80 to 60/40 in 20 min, flow rate 1.0 mL/min. Low-resolution mass spectrometry was performed with a JEOL™ SX102 spectrometer with 6-kV Xe atoms following desorption from a glycerol matrix or on an AGILENT™ LC/MS 1100 MSD, with a WATERS™ (Milford, Mass.) ATLANTIS™ C18 column. High resolution mass spectroscopic (HRMS) measurements were performed on a proteomics optimized Q-TOF-2 (MICROMASS-WATERS™) using external calibration with polyalanine, unless noted. Observed mass accuracies are those expected based on known performance of the instrument as well as trends in masses of standard compounds observed at intervals during the series of measurements. Reported masses are observed masses uncorrected for this time-dependent drift in mass accuracy.

EXAMPLE 1

This example illustrates the synthesis of compounds in accordance with an embodiment of the invention.

(1'S,2'R,3'S,4'S,5'S)-4'-[6-Chloro-2-iodo-purin-9-yl]-2',3'-isopropylidene-bicyclo[3.1.0]hexane-1'-carboxylic acid ethyl ester (22), (1'S,2'R,3'S,4'S,5'S)-4'-[6-(3-Chlorobenzylamino)-2-iodopurin-9-yl]-2',3'-O-isopropylidene bicyclo[3.1.0]hexane-1'-carboxylic N-methylamide (23), (1'S,2'R,3'S,4'S,5'S)-4'-[2,6-Dichloro-purin-9-yl]-2',3'-isopropylidene-bicyclo[3.1.0]hexane-F-carboxylic acid methyl ester (24), and (1'S,2'R,3'S,4'S,5'S)-4'-[6-(3-Iodobenzylamino)-2-iodopurin-9-yl]-2',3'-O-isopropylidene bicyclo [3.1.0]hexane-1'-carboxylic N-methylamide (25) were prepared according to a published method. Tchilibon et al., *J. Med. Chem.*, 2005, 48, 1745-1758.

(1'S,2'R,3'S,4'S,5'S)-4'-[6-(2,5-Dimethoxybenzylamino)-2-iodopurin-9-yl]-2',3'-dihydroxybicyclo[3.1.0]hexane-1'-carboxylic acid N-methylamide (2). To a solution of compound 22 (49 mg, 0.1 mmol) in dichloromethane (0.1 mL) was added 2,5-dimethoxybenzylamine (167 mg, 1 mmol). The reaction mixture was left for 16 h at 22° C., transferred to a chromatographic column, and eluted with 30% to 50% ethyl acetate-hexane to afford the corresponding 6-(2,5-dimethoxybenzyl) derivative. The product was dissolved in a 33% solution of methylamine in ethanol and left at room temperature for 48 h. The reaction mixture was evaporated, and the residue was purified by flash chromatography (50% to 100% ethyl acetate-hexane) to afford the corresponding N-methylamide. The product was dissolved in MeOH (3 mL), and TFA (0.3 mL), and water (3 mL) were added, and the reaction mixture was stirred for 16 h at 70° C. The reaction mixture was evaporated, and the residue was purified by flash chromatography (0 to 10% methanol-ethyl acetate) to afford the title compound 2 (10 mg, 21%). $^1$H NMR (CD$_3$OD) 7.94 (s, 1H), 6.98 (d, 1H, J=2.7 Hz), 6.89 (d, 1H, J=9.3 Hz), 6.78 (dd, 1H, J=2.7, 9.0 Hz), 5.09 (d, 1H, J=7.2 Hz), 4.78 (s, 1H), 4.57 (br s, 2H), 3.98 (d, 1H, J=6.6 Hz), 2.88 (s, 3H), 2.01 (m, 1H), 1.78 (t, 1H, J=4.8 Hz), 1.33 (m, 1H). HRMS (ESI MS m/z) Calcd. for C$_{22}$H$_{25}$IN$_6$O$_5$ (M+H)+ 581.10039. found 581.0955.

(1'S,2'R,3'S,4'S,5'S)-4'-[6-Methoxyamino-2-chloropurin-9-yl]-2',3'-dihydroxybicyclo[3.1.0]hexane-1'-carboxylic acid N-methylamide (21). To a solution of compound 24 (20 mg, 0.033 mmol) in dichloromethane (0.1 mL) was added a solution of O-methylhydroxylamine hydrochloride (84 mg, 1 mmol) and triethylamine (101 mg, 1 mmol) in ethanol (0.5 mL). The reaction mixture was left for 16 h at 22° C., diluted with ethyl acetate (30 mL), washed with water, dried, and evaporated. The residue was dissolved in 33% solution of methylamine in ethanol and stirred at room temperature for 48 h. The reaction mixture was evaporated, and the residue was purified by flash chromatography (50% to 100% ethyl acetate-hexane) to afford the corresponding N-methylamide. The product was dissolved in MeOH (3 mL), and TFA (0.3 mL) and water (3 mL) were added. The reaction mixture was stirred for 16 h at 70° C. The reaction mixture was evaporated, and the residue was purified by flash chromatography (0% to 10% methanol-ethyl acetate) to afford the title compound 21 (1.5 mg, 8.5%). $^1$H NMR (CD$_3$OD): 7.45 (s, 1H), 5.07 (d, 1H, J=6.3 Hz), 4.63 (s. 1H), 4.04 (d, 1H, J=6.6 Hz), 3.80 (s, 3H) 2.78 (s, 3H), 2.04 (m, 1H), 1.72 (m, 1H), 1.31 (m, 1H). HRMS (ESI MS m/z) Calcd for C$_{14}$H$_{16}$ClN$_6$O$_4^-$ (M−H$^+$) 367.0927. found 367.0930.

(1'S,2'R,3'S,4'S,5'S)-4'-[6-(3-Chlorobenzylamino)-2-trimethylsilylethynyl-9-yl]-2',3'-dihydroxybicyclo[3.1.0]hexane-1'-carboxylic acid N-methylamide (4). To a solution of (1'S,2'R,3'S,4'S,5'S)-4'-[6-(3-chlorobenzylamino)-2-iodopurin-9-yl]-2',3'-O-isopropylidene bicyclo[3.1.0]hexane-P-carboxylic N-methylamide 23, 30 mg, 0.05 mmol), dichlorobis(triphenylphosphine)palladium(II) (7 mg, 0.01 mmol), and in DMF (0.05 mL) under nitrogen was added trimethylsilylacetylene (20 mg, 0.20 mmol) and then triethylamine (101 mg, 0.5 mmol). The reaction was stirred at room temperature for 16 h, diluted with ethyl acetate, washed with water, dried, and evaporated. The residue was purified by flash chromatography (30% to 100% ethyl acetate-hexane) to afford the corresponding 2-trimethylsilylethynyl derivative. The product was dissolved in MeOH (3 mL), TFA (0.3 mL) and water (3 mL) were added, and the reaction mixture was stirred for 16 h at 70° C. The reaction mixture was evaporated, and the residue was purified by flash chromatography (0 to 10% methanol-ethyl acetate) to afford the title compound 4 (38%). $^1$H NMR (CD$_3$OD): 8.10 (s, 1H), 7.42 (s, 1H), 7.28 (m, 3H), 4.96 (d, 1H, J=6.6 Hz), 4.7-4.9 (br. m. 3H), 3.97 (d, 1H, J=6.6 Hz) 2.84 (s, 3H), 2.09 (m, 1H), 1.86 (t, 1H, J=5.1 Hz), 1.36 (m, 1H), 0.27 (s, 9H). HRMS (ESI MS m/z) Calcd for C$_{25}$H$_{30}$ClN$_6$O$_3$Si$^+$ (M+H)$^+$ 525.1832. found 525.1837.

(1'S,2'R,3'S,4'S,5'S)-4'-[6-(3-Chlorobenzylamino)-2-(1-pentynyl)-9-yl]-2',3'-dihydroxybicyclo[3.1.0]hexane-1'-carboxylic acid N-methylamide (5). To a solution of (1'S,2'R, 3'S,4'S,5'S)-4'-[6-(3-chlorobenzylamino)-2-iodopurin-9-yl]-2',3'-O-isopropylidene bicyclo[3.1.0]hexane-1'-carboxylic N-methylamide (23) (30 mg, 0.05 mmol), dichlorobis(triphenylphosphine)palladium(II) (7 mg, 0.01 mmol), and CuI (1 mg, 0.005 mmol) in DMF (0.05 mL) under nitrogen was added 1-pentyne (14 mg, 0.20 mmol) and then triethylamine (101 mg, 0.5 mmol). The reaction was stirred at room temperature for 16 h, diluted with ethyl acetate, washed with water, dried, and evaporated. The residue was purified by flash chromatography (30% to 100% ethyl acetate-hexane) to afford the corresponding 2-(1-pentynyl) derivative. The product was dissolved in MeOH (3 mL), TFA (0.3 mL) and water (3 mL) were added, and the reaction mixture was stirred for 16 h at 70° C. The reaction mixture was evaporated, and the residue was purified by flash chromatography (0% to 10% methanol-ethyl acetate) to afford the title compound 5. Yield 51%. $^1$H NMR (CD$_3$OD): 8.06 (s, 1H), 7.41 (s, 1H), 7.23-7.30 (m, 3H), 4.99 (d, 1H, J=5.7 Hz), 4.80 (br. s, 3H), 3.96 (d, 1H, J=6.6 Hz), 2.84 (s, 3H), 2.42 (t, 2H, J=7.2 Hz), 2.07 (m, 1H), 1.84 (t, 1H, J=4.5 Hz), 1.65 (sextet, 2H, J=7.2 Hz), 1.36 (m, 1H). HRMS (ESI MS m/z) Calcd for C$_{25}$H$_{28}$ClN$_6$O$_3^+$ (M+H)$^+$ 495.1906. found 495.1911.

(1'S,2'R,3'S,4'S,5'S)-4'-[6-(3-Chlorobenzylamino)-2-(5-methoxycarbonyl-1-pentynyl)-9-yl]-2',3'-dihydroxybicyclo [3.1.0]hexane-1'-carboxylic acid N-methylamide (6) and (1'S,2'R,3'S,4'S,5'S)-4'-[6-(3-chlorobenzylamino)-2-(5-hydroxycarbonyl-1-pentynyl)-9-yl]-2',3'-dihydroxybicyclo [3.1.0]hexane-1'-carboxylic acid N-methylamide (7). To a solution of (1'S,2'R,3'S,4'S,5'S)-4'-[6-(3-chlorobenzylamino)-2-iodopurin-9-yl]-2',3'-O-isopropylidenebicyclo [3.1.0]hexane-1'-carboxylic N-methylamide (23) (30 mg, 0.05 mmol), dichlorobis(triphenylphosphine)palladium(II) (7 mg, 0.01 mmol), and CuI (1 mg, 0.005 mmol) in DMF (0.05 mL) under nitrogen was added methyl ω-hexynoate (26 mg, 0.20 mmol) and then triethylamine (101 mg, 0.5 mmol). The reaction was stirred at room temperature for 16 h, diluted with ethyl acetate, washed with water, dried, and evaporated. The residue was purified by flash chromatography (30% to 100% ethyl acetate-hexane) to afford the corresponding 2-(5-methoxycarbonylpentyn-1-yl) derivative. The product was dissolved in MeOH (3 mL), TFA (0.3 mL) and water (3 mL) were added, and the reaction mixture was stirred for 16 h at 70° C. The reaction mixture was evaporated, and the residue was purified by flash chromatography (0% to 10% methanol-ethyl acetate) to afford the title compound 6 (31%). $^1$H NMR (CD$_3$OD): 7.98 (s, 1H), 7.31 (s, 1H), 7.15-7.31 (m, 3H), 4.91 (d, 1H, J=6.9 Hz), 4.70 (br. s, 3H), 3.89 (d, 1H, J=6.6 Hz), 3.57 (s, 3H), 2.75 (s, 3H), 2.44 (m, 4H), 1.98 (m, 1H), 1.84 (m, 2H), 1.75 (m, 1H), 1.27 (m, 1H). HRMS (ESI MS m/z) Calcd for C$_{27}$H$_{30}$ClN$_6$O$_5^+$ (M+H)$^+$ 553.1961. found 553.1970. Further elution with 20% methanol-ethyl acetate provided the title compound 7 (21%). $^1$H NMR (CD$_3$OD): 7.96 (s, 1H), 7.31 (s, 1H), 7.15-7.22 (m, 3H), 4.97 (d, 1H, J=6.6 Hz), 4.75 (br. s., 3H), 3.90 (d, 1H, J=6.6 Hz), 2.76 (s, 3H), 2.41 (t, 2H, J=7.2 Hz), 2.29 (t, 2H, J=7.2 Hz), 1.96 (m, 1H), 1.83 (m, 3H), 1.74 (m, 1H), 1.26 (m, 1H). HRMS (ESI MS m/z) Calcd for C$_{26}$H$_{28}$ClN$_6$O$_5^+$ (M+H)$^+$ 539.1804. found 537.1673.

(1'S,2'R,3'S,4'S,5'S)-4'-[6-(3-Chlorobenzylamino)-2-(1-ethynyl)-9-yl]-2',3'-dihydroxybicyclo[3.1.0]hexane-1'-carboxylic acid N-methylamide (3). To a solution of compound 4 (10 mg) in THF (1 mL) was added 1M solution of tetrabutylammonium fluoride in THF (0.2 mL). The reaction mixture was stirred for 1 h, evaporated, and the residue was purified by flash chromatography (0% to 10% methanol-ethyl acetate) to afford the title compound 3. Yield 75%. $^1$H NMR (CD$_3$OD) 8.1 (s, 1H), 7.41 (d, 1H, J=2.7 Hz), 6.89 (d, 1H, J=9.3 Hz), 6.78 (dd, 1H, J=2.7, 9.0 Hz), 5.06 (d, 1H, J=6.6 Hz), 4.83 (br. s., 2H), 3.99 (d, 1H, J=6.6 Hz), 2.87 (s, 3H), 2.06 (m, 1H), 1.83 (t, 1H, J=4.8 Hz), 1.38 (m, 1H). HRMS (ESI MS m/z) Calcd for C$_{22}$H$_{22}$ClN$_6$O$_3$ (M+H)+ 453.1437. found 453.1444.

(1'S,2'R,3'S,4'S,5'S)-4'-[6-(3-Chlorobenzylamino)-2-[5-(β-aminoethylaminocarbonyl)-1-pentynyl)]-9-yl]-2',3'-dihydroxybicyclo[3.1.0]hexane-1'-carboxylic acid N-methylamide (8). To a solution of ester 6 (2.4 mg, 0.0045 mmol) in methanol (0.05 mL) was added ethylenediamine (1 mL). The reaction mixture was stirred at room temperature for 60 h, and was evaporated to dryness. The residue was purified by flash chromatography (30 to 70% MeOH-EtOAc) to afford the title amide 8 (2.0 mg, 0.0034 mmol, 76%). $^1$H NMR: 7.98 (s, 1H), 7.31 (s, 1H), 7.16-7.22 (m, 3H), 4.92 (d, 1H, J=6.6 Hz), 4.69 (s, 1H), 4.74 (br. s, 2H, under HDO peak) 3.88 (d, 1H, J=6.6 Hz), 3.14 (m, 2H, J=6.3 Hz), 2.75 (s, 3H), 2.63 (t, 2H, J=6.3 Hz), 2.44 (m, 2H), 2.33 (t, 2H, J=7.5 Hz), 1.97 (m, 1H), 1.87 (m, 2H), 1.75 (t, 1H, J=4.8 Hz), 1.28 (m, 1H).

(1'S,2'R,3'S,4'S,5'S)-4'-6-[3-[5-(Methoxycarbonyl)-1-pentynyl]phenylmethylamino]-2-chloro-9-yl}-2',3'-dihydroxybicyclo[3.1.0]hexane-1'-carboxylic acid N-methylamide (26) and (1'S,2'R,3'S,4'S,5'S)-4'-6-[3-[5-(hydroxycarbonyl)-1-pentynyl]phenylmethylamino]-2-chloro-9-yl}-2',3'-dihydroxybicyclo[3.1.0]hexane-1'- carboxylic acid N-methylamide (9). To a solution of compound 25 (60 mg, 0.1 mmol), dichlorobis(triphenylphosphine)palladium(II) (14 mg, 0.02 mmol), and CuI (2 mg, 0.01 mmol) in DMF (0.1 mL) under nitrogen was added methyl w-hexynoate (63 mg, 0.5 mmol) and then triethylamine (202 mg, 1 mmol). The reaction was stirred at room temperature for 16 h, diluted with ethyl acetate, washed with water, dried, and evaporated. The residue was purified by flash chromatography (30% to 100% ethyl acetate-hexane) to afford corresponding 3-(5-methoxycarbonylpentyn-1-yl)phenylaminomethyl derivative. The product was dissolved in MeOH (6 mL), TFA (0.5 mL) and water (2 mL) were added, and the reaction mixture was stirred for 16 h at 70° C. The reaction mixture was evaporated, and the residue was purified by flash chromatography (0% to 10% methanol-ethyl acetate) to afford compounds title methyl ester 27 (28 mg, 0.051 mmol, 51%). $^1$H NMR (CD$_3$OD) 8.04 (s, 1H), 7.39 (s, 1H), 7.24-7.32 (m, 3H), 5.06 (d, 1H, J=6.6 Hz), 4.80 (s, 1H), 4.72 (br. s, 2H), 3.99 (d, 1H, J=6.6 Hz), 3.64 (s, 3H), 2.85 (s, 3H), 2.48 (t, 2H, J=6.9 Hz), 2.45 (t, 2H, J=6.9 Hz), 2.04 (m, 1H), 2.01 (m, 2H), 1.80 (t, 1H, J=5.1 Hz), 1.36 (m, 1H). HRMS (ESI MS m/z) Calcd for $C_{27}H_{30}ClN_6O_5^+$ (M+H)$^+$ 553.1961. found 553.1981. Further elution with 20% MeOH-EtOAc provided the carboxylic acid 9 (12 mg, 0.028 mmol, 22%). $^1$H NMR (DMSO-d6) 8.89 (t, 1H, J=6.0 Hz), 8.10 (s, 1H), 7.57 (q, 1H, J=5.2, 4.8), 7.37 (s, 1H), 7.23-7.34 (m, 3H), 5.45 (br s, 1H), 4.94 (d, 1H, J=4.7 Hz), 4.84 (br s, 1H), 4.66 (s, 1H), 4.62 (d, 2H, J=4.8), 3.89 (d, 1H, J=5.1), 2.67 (d, 3H, J=3.9 Hz), 2.44 (t, 2H, J=6.9 Hz), 2.36 (t, 2H, J=8.1 Hz), 1.83 (m, 1H), 1.75 (m, 2H), 1.60 (t, 1H, J=5.2 Hz), 1.30 (m, 1H).

(1'S,2'R,3'S,4'S,5'S)-4'-6-[3-[5-β-Aminoethylaminocarbonyl)-1-pentynyl]phenylmethylamino]-2-chloro-9-yl}-2',3'-dihydroxybicyclo[3.1.0]hexane-1'-carboxylic acid N-methylamide (10). To a solution of ester 27 (60 mg, 0.11 mmol) in methanol (0.1 mL) was added ethylenediamine (2 mL). The reaction mixture was stirred at room temperature for 60 h, and was evaporated to dryness. The residue was purified by flash chromatography (30 to 70% MeOH-EtOAc) to afford the title amide 10 (57 mg, 0.98 mmol, 88%). $^1$H NMR (CD$_3$OD) 8.14 (s, 1H), 7.51 (s, 1H), 7.15-7.31 (m, 3H), 5.17 (d, 1H, J=7.2 Hz), 4.91 (s, 1H), 4.83 (br. s, 2H) 4.10 (d, 1H, J=6.6 Hz), 3.35 (t, 3H, J=6.0 Hz), 2.96 (s, 3H), 2.82 (t, 2H, J=6.6 Hz), 2.56 (t, 2H, J=6.9 Hz), 2.49 (t, 2H, J=7.8 Hz), 2.16 (m, 1H), 2.01 (m, 2H), 1.91 (t, 1H, J=4.8 Hz), 1.47 (m, 1H). HRMS (ESI MS m/z) Calcd for C28H34ClN8O4+ (M+H)+ 581.2386. found 581.2392.

(1'S,2'R,3'S,4'S,5'S)-4'-6-[3-[5-(β-Acetylaminoethylaminocarbonyl)-1-pentynyl]phenylmethylamino]-2-chloro-9-yl}-2',3'-dihydroxybicyclo[3.1.0]hexane-1'-carboxylic acid N-methylamide (11). To a solution of amine 10 (2 mg, 0.0034 mmol) in methanol (1 mL) was added acetic anhydride (10 mkL, 0.01 mmol). The reaction mixture was stirred for 16 h, evaporated, and the residue was evaporated with dioxane (3×1 mL) to afford compound 11 (2.2 mg, 0.0034 mL, quant. yield). $^1$H NMR (CD$_3$OD) 7.93 (s, 1H), 7.15-7.22 (m, 4H), 4.97 (d, 1H, J=4.8 Hz), 4.70 (s, 1H), 4.62 (br. s, 2H) 3.90 (d, 1H, J=6.6 Hz), 3.16 (s, 4H), 2.76 (s, 3H), 2.36 (t, 2H, J=6.6 Hz), 2.26 (t, 2H, J=7.8 Hz), 1.95 (m, 1H), 1.82 (s, 3H), 1.77 (m, 2H), 1.72 (t, 11-1, J=4.8 Hz), 1.28 (m, 1H). HRMS (ESI MS m/z) Calcd for $C_{30}H_{36}ClN_8O_5^+$ (M+H)$^+$ 623.2492 Found 623.2501.

Figure 3:
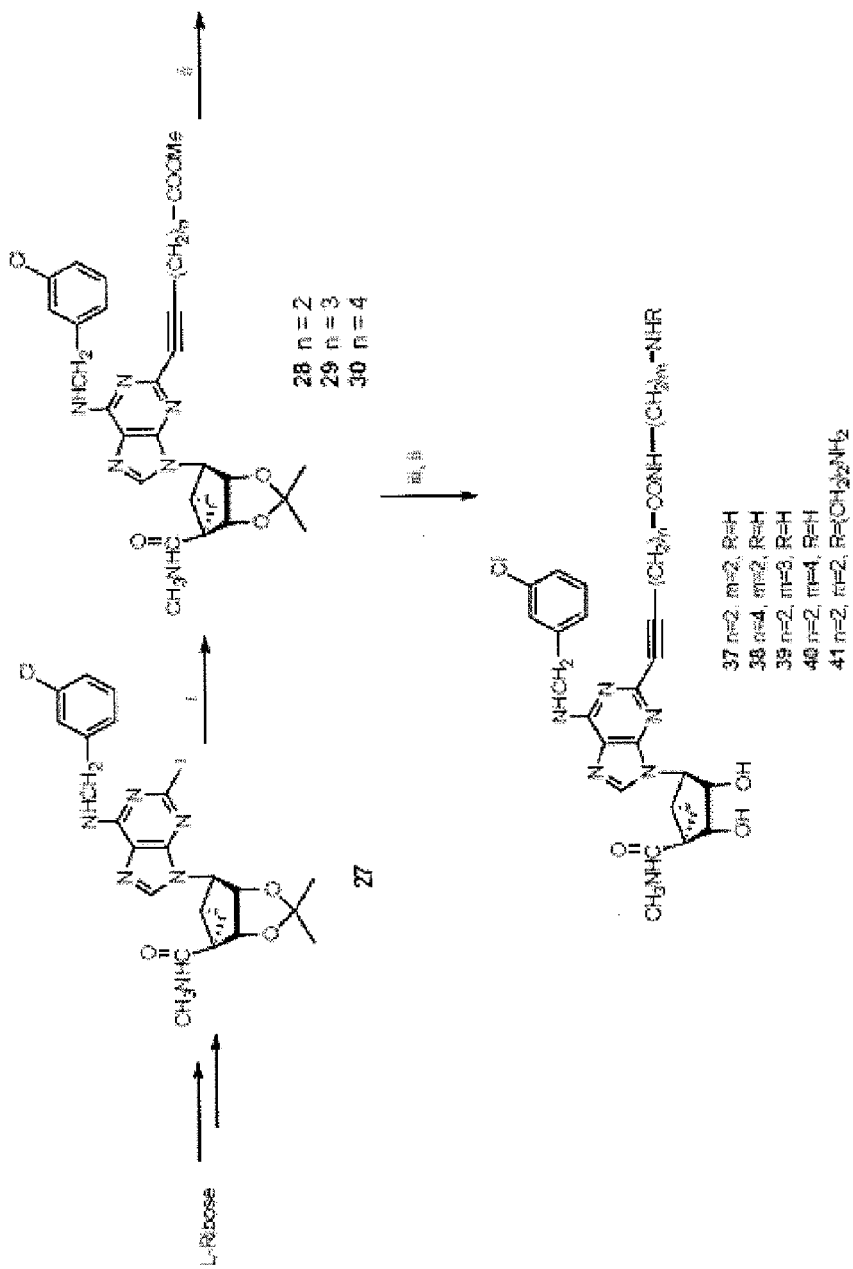
FIG. 3 depicts a reaction scheme for the synthesis of compounds 37 to 41 in accordance with an embodiment of the invention.

(1'S,2'R,3'S,4'S,5'S)-4'-[6-(3-Chlorobenzylamino)-2-(4-methoxycarbonyl-1-butynyl)-9-yl]-2',3'-O-isopropylidenebicyclo[3.1.0]hexane-1'-carboxylic acid N-methylamide (28) (FIG. 3). To a solution of compound 27 (52 mg, 0.087 mmol) in anhydrous DMF (1.5 mL), PdCl$_2$(PPh$_3$)$_2$ (12 mg, 0.017 mmol), CuI (2 mg, 0.010 mmol), methyl-ω-pentynate (39 mg, 0.347 mmol) and then triethylamine (0.12 mL, 0.86 mmol) was added. The reaction mixture was stirred at room temperature for overnight. Solvent was evaporated under vacuum, and the residue was purified on flash silica gel column chromatography (CH$_2$Cl$_2$:MeOH=30:1) to give compound 28 (40 mg, 78%) as foamy syrup. $^1$H NMR (CD$_3$OD, 300 MHz) δ 8.16 (s, 1H), 7.42-7.44 (m, 4H), 5.81 (d, J=6.7 Hz, 1H), 5.02 (s, 1H), 4.82 (m, 2H) 3.78 (s, 3H), 2.85 (s, 3H), 2.72-281 (m, 5H), 2.09-2.14 (m, 1H), 1.55 (s, 3H), 1.41 (t, J=5.1 Hz, 1H), 1.29 (s, 3H), 0.82-0.96 (m, 1H). HRMS calculated for $C_{29}H_{32}ClN_6O_5$ (M+H)$^+$ : 579.2105. found 579.2123.

(1'S,2'R,3'S,4'S,5'S)-4'-[6-(3-Chlorobenzylamino)-2-(6-methoxycarbonyl-1-hexynyl)-9-yl]-2',3'-O-isopropylidenebicyclo[3.1.0]hexane-1'-carboxylic acid N-methylamide (30). Compound 30 (74%) was synthesized from 27 following the same procedure as for compound 28. $^1$H NMR (CD$_3$OD, 300 MHz) δ 8.12 (s, 1H), 7.41-7.20 (m, 4H), 5.75 (d, J=6.9 Hz, 1H), 4.98 (s, 1H), 4.86 (m, 2H), 3.66 (s, 3H), 2.84 (s, 3H), 2.38-2.55 (m, 4H), 2.06-2.15 (m, 1H), 1.64-1.91 (m, 4H), 1.53 (s, 3H), 1.38 (m, 1H), 1.24-1.32 (m, 4H), 0.84-0.97 (m, 1H). HRMS calculated for $C_{31}H_{36}ClN_6O_5$ (M+H)$^+$ : 607.2426. found 607.2436.

(1'S, 2'R, 3'S, 4'S, 5'S)-4'-[6-(3-Chlorobenzylamino) 2-(4-(β-aminoethylaminocarbonyl)-1-butynyl)-9-yl]-2',3'-dihydroxybicyclo[3.1.0]hexane-1'-carboxylic acid N-methylamide (37). To a solution of compound 28 (20 mg, 0.034 mmol) in methanol (0.3 mL), ethylenediamine (1.5 mL) was added and stirred for overnight at room temperature. Solvent was evaporated and the residue was roughly purified on flash silica gel column chromatography. The aminated product was dissolved in methanol (1.5 mL) and 10% trifluoroacetic acid (1.5 mL) and heated at 70° C. for 15 h. Solvent was evaporated and the residue was purified on flash silica gel column chromatography (CH$_2$Cl$_2$:MeOH:NH$_4$OH=10:1:0.1) to give compound 37 (15 mg, 79%). $^1$H NMR (CD$_3$OD, 300 MHz) δ 8.09 (s, 1H), 7.39 (s, 1H), 7.27-7.32 (m, 3H), 4.99 (d, J=6.6 Hz, 1H), 4.78-4.91 (m, 2H), 3.97 (d, J=6.6 Hz, 1H), 3.33-3.36 (m, 4H), 2.87 (s, 3H), 2.75-2.80 (m, 4H), 2.53 (t, J=7.2 Hz, 2H), 2.59-3.41 (m, 1H), 1.88 (t, J=4.5 Hz, 1H), 1.34-1.43 (m, 1H). HRMS calculated for $C_{27}H_{31}ClN_6O_2Na$ (M+Na)$^+$: 589.2068. found 589.2054.

(1'S,2'R,3'S,4'S,5'S)-4'-[6-(3-Chlorobenzylamino)-2-(6-(β-aminoethylaminocarbonyl)-1-hexynyl)-9-yl]-2',3'-dihydroxybicyclo[3.1.0]hexane-1'-carboxylic acid N-methylamide (38). Compound 38 (82%) was synthesized from compound 30 following the same procedure as for compound 37. $^1$H NMR (CD$_3$OD, 300 MHz) δ 8.06 (s, 1H), 7.40 (s, 1H), 7.28-7.31 (m, 3H), 5.01 (d, J=6.7 Hz, 1H), 4.84 (m, 2H), 3.98 (d, J=6.7 Hz, 1H), 3.24 (t, J=6.3 Hz, 2H), 2.85 (s, 3H), 2.72 (t, J=6.3 Hz, 2H), 2.48 (t, J=6.2 Hz, 2H), 2.27 (t, J=7.5 Hz, 2H), 2.23 (m, 1H), 1.74-1.88 (m, 3H), 1.60-1.73 (m, 2H), 1.32-1.42 (m, 1H), 0.81-0.98 (m, 1H). $^1$HRMS calculated for $C_{29}H_{36}ClN_8O_4$ (M+H)$^+$ : 595.2527. found 595.2548.

(1'S, 2'R, 3'S, 4'S, 5'S)-4'-[6-(3-Chlorobenzylamino)-2-(4-(β-aminopropylaminocarbonyl)-1-butynyl)-9-yl]-2',3'-dihydroxybicyclo[3.1.0]hexane-1'-carboxylic acid N-methylamide (39). Compound 39 (78%) was synthesized from compound 28 following the same procedure as for compound 37. $^1$H NMR (CD$_3$OD, 300 MHz) δ 8.09 (s, 1H), 7.39 (s, 1H), 7.25-7.32 (m, 3H), 5.03 (d, J=6.6 Hz, 1H), 4.81-4.86 (m, 2H), 4.99 (d. J=6.6 Hz, 1H), 3.35-3.37 (m, 2H), 2.87 (s, 3H), 2.67-2.82 (m, 4H), 2.52 (t, J=6.9 Hz, 2H), 2.06-2.10 (m, 1H), 1.85 (t, J=3.6 Hz, 1H), 1.62-1.71 (m, 2H), 1.36-1.40 (m, 1H). 0.78-0.92 (m, 1H). HRMS calculated for $C_{28}H_{34}ClN_8O_4$ (M+H)$^+$ : 581.2392. found 581.2376.

(1'S, 2'R, 3'S, 4'S, 5'S)-4'-[6-(3-Chlorobenzylamino)-2-(4-(β-aminobutylaminocarbonyl)-1-butynyl)-9-yl]-2',3'-dihydroxybicyclo[3.1.0]hexane-1'-carboxylic acid N-methylamide (40). Compound 40 (74%) was synthesized from compound 28 following the same procedure as for compound 37. $^1$H NMR (CD$_3$OD, 300 MHz) δ 8.09 (s, 1H), 7.40 (s, 1H), 7.28-7.32 (m, 3H), 5.04 (d, J=5.9 Hz, 1H), 4.82-4.86 (m, 2H), 3.99 (d, J=6.0 Hz, 1H), 3.34-3.38 (m, 2H), 2.87 (s, 3H), 2.69-2.82 (m, 4H), 2.48-2.54 (m, 2H), 2.06-2.10 (m, 1H), 1.86 (t, 5.1 Hz, 1H), 1.52-1.56 (m, 4H), 1.36-1.41 (m, 1H), 0.76-0.97 (m, 1H). HRMS calculated for C$_{29}$H$_{36}$ClN$_8$O$_4$ (M+H)$^+$ : 595.2548. found 595.2533.

(1'S,2'R,3'S,4'S,5'S)-4'-[6-(3-Chlorobenzylamino)-2-(4-(β-aminoethyl-N-aminoethylaminocarbonyl)-1-butynyl)-9-yl]-2',3'-dihydroxybicyclo[3.1.0]hexane-1'-carboxylic acid N-methylamide (41). Compound 41 (69%) was synthesized from compound 28 following the same procedure as for compound 37. $^1$H NMR (CD$_3$OD, 300 MHz) δ 8.10 (s, 1H), 7.40 (s, 1H), 7.25-7.33 (m, 3H), 5.05 (d, J=5.4 Hz, 1H), 4.78-4.86 (m, 2H), 4.01 (d, J=6.3 Hz, 1H), 3.33-3.36 (m, 4H), 2.87 (s, 3H), 2.73-2.86 (m, 6H), 2.58 (t, J=6.9 Hz, 2H), 2.06-2.10 (m, 1H), 1.86 (t, J=5.1 Hz, 1H), 1.36-1.41 (m, 1H), 0.88-0.94 (m, 1H). HRMS calculated for C$_{29}$H$_{37}$ClN$_9$O$_4$ (M+H)$^+$ : 610.2657. found 610.2676.

(1'S,2'R,3'S,4'S,5'S)-4'-[6-(3-Chlorobenzylamino)-2-(4-methoxycarbonyl)-1-butynyl)-9-yl]-2',3'-dihydroxybicyclo[3.1.0]hexane-1'-carboxylic acid N-methylamide (35). A solution of compound 28 (67 mg, 0.115 mmol) in methanol (3 mL) and 10% triflromethanesulfonic acid (2 mL) was heated at 70° C. for overnight. Solvent was evaporated and the residue was purified on flash silica gel column chromatography (CH$_2$Cl$_2$:MeOH=20:1) to give compound 35 (46 mg, 75%). $^1$H NMR (CD$_3$OD, 300 MHz) δ 8.13 (s, 1H), 7.40 (s, 1H), 7.22-7.45 (m, 3H), 5.10 (d, J=6.3 Hz, 1H), 4.80-4.86 (m, 2H), 4.03 (d, J=6.6 Hz, 1H), 3.63 (s, 3H), 2.86 (s, 3H), 2.76-2.85 (m, 2H), 2.46-2.58 (m, 2H), 2.05-2.10 (m, 1H), 1.77-1.83 (m, 1H), 1.35-1.40 (m, 1H), 0.82-0.96 (m, 1H). HRMS calculated for C$_{26}$H$_{28}$ClN$_6$O$_5$ (M+H)$^+$ : 539.1731. found 539.1743.

(1'S,2'R,3'S,4'S,5'S)-4'-[6-(3-Chlorobenzylamino)-2-(6-methoxycarbonyl)-1-hexynyl)-9-yl]-2',3'-dihydroxybicyclo[3.1.0]hexane-1'-carboxylic acid N-methylamide (36). Compound 36 (71%) was synthesized from compound 30 following the same procedure as for compound 35. $^1$H NMR (CD$_3$OD, 300 MHz) δ 8.11 (s, 1H), 7.43 (s, 1H), 7.24-7.45 (m, 3H), 5.02 (d, J=6.3 Hz, 1H), 4.80-4.86 (m, 2H), 3.99 (d, J=6.6 Hz, 1H), 3.67 (s, 3H), 2.87 (s, 3H), 2.51 (t, J=6.9 Hz, 2H), 2.42 (t, J=7.5 Hz, 2H), 2.07-2.1 (m, 1H), 1.66-1.88 (m, 4H), 1.35-1.40 (m, 2H), 0.98-1.21 (m, 1H). HRMS calculated for C$_{28}$H$_{32}$ClN$_6$O$_5$ (M+H)$^+$ : 567.2123. found 567.2114.

(1'S,2'R,3'S,4'S,5'S)-4'-[6-(3-Chlorobenzylamino)-2-(4-hydroxycarbonyl)-1-butynyl)-9-yl]-2',3'-dihydroxybicyclo[3.1.0]hexane-1'-carboxylic acid N-methylamide (33). To a solution of ester 35 (30 mg, 0.055 mmol) in methanol (1.5 mL), 1M solution of potassium hydroxide (1 mL) was added and stirred at room temperature for overnight. The reaction mixture was neutralized with acetic acid and solvent was evaporated and the residue was purified on flash silica gel column chromatography (CH$_2$Cl$_2$:MeOH=10:1) to give compound 33 (23 mg, 80%). $^1$H NMR (CD$_3$OD, 300 MHz) δ 8.06 (s, 1H), 7.38 (s, 1H), 7.24-7.35 (m, 3H), 5.14 (d, J=5.8 Hz, 1H), 4.79-4.86 (m, 2H), 4.03 (d, J=6.3 Hz, 1H), 2.87 (s, 3H), 2.42-2.80 (m, 4H), 2.04-2.32 (m, 1H), 1.82 (t, J=4.8 Hz, 1H), 1.36-1.40 (m, 1H), 0.84-0.97 (m, 1H). HRMS calculated for C$_{25}$H$_{26}$ClN$_6$O$_5$ (M+H)$^+$ : 525.9562. found 525.9583.

(1'S,2'R,3'S,4'S,5'S)-4'-[6-(3-Chlorobenzylamino)-2-(4-hydroxycarbonyl)-1-hexynyl)-9-yl]-2',3'-dihydroxybicyclo[3.1.0]hexane-1'-carboxylic acid N-methylamide (34). Compound 34 (77%) was prepared from compound 35 following the same method as for compound 33. $^1$H NMR (CD$_3$OD, 300 MHz) δ 8.08 (s, 1H), 7.43 (s, 1H), 7.24-7.42 (m, 3H), 5.06 (d, J=6.6 Hz, 1H), 4.81-4.85 (m, 2H), 4.02 (d, J=6.0 Hz, 1H), 2.87 (s, 3H), 2.50 (t, J=6.9 Hz, 2H), 2.35 (t, J=7.5 Hz, 2H), 2.12-2.04 (m, 1H), 1.70-1.87 (m, 4H), 1.35-1.40 (m, 2H), 0.84-0.96 (m, 1H). HRMS calculated for C$_{27}$H$_{30}$ClN$_6$O$_5$ (M+H)$^+$ : 553.1966. found 553.1976.

(1'S,2'R,3'S,4'S,5'S)-4'-[6-(3-Chlorobenzylamino)-2-(N-biotinyl(β-aminoethylaminocarbonyl)-1-butynyl)-9-yl]-2',3'-dihydroxybicyclo[3.1.0]hexane-1'-carboxylic acid N-methylamide (42). To a solution of compound 37 (4 mg, 0.007 mmol) in dry DMF (0.5 mL), biotin (1.89 mg, 0.0077 mmol), HATU (3.2 mg, 0.0084 mmol) and DIEA (1.6 μL, 0.009 mmol) was added and stirred at room temperature for overnight. Solvent was evaporated and the residue was purified on flash silica gel column chromatography (CH$_2$Cl$_2$:MeOH:NH$_4$OH=5:1:0.1) to give compound 42 (3.5 mg, 62%). $^1$H NMR (CD$_3$OD, 300 MHz) δ 8.14 (s, 1H), 7.43 (s, 1H), 7.29-7.39 (m, 3H), 5.07 (d, J=6.9 Hz, 1H), 4.78-4.86 (m, 2H), 4.48-4.52 (m, 1H), 4.28-4.32 (m, 1H), 4.04 (d, J=6.3 Hz, 1H), 3.70-3.82 (m, 2H), 3.24-3.31 (m, 1H), 3.08-3.23 (m, 1H), 2.91 (s, 3H), 2.70-2.83 (m, 4H), 2.56 (t, J=7.5 Hz, 2H), 2.04-2.15 (m, 2H), 1.89 (t, J=5.1 Hz, 1H), 1.33-1.70 (m, 10H), 0.84-1.02 (m, 1H). HRMS calculated for C$_{37}$H$_{46}$ClN$_{10}$O$_6$S (M+H)$^+$ : 793.3011. found 793.3030.

(1'S,2'R,3'S,4'S,5'S)-4'-[6-(3-Chlorobenzylamino)-2-(N-biotinyl {5-aminopentanyl}(β-aminoethylaminocarbonyl)-1-butynyl)-9-yl]-2',3'-dihydroxybicyclo[3.1.0]hexane-1'-carboxylic acid N-methylamide (43). To a solution of compound 37 (3.4 mg, 0.0059 mmol) in DMF (0.5 mL), sulfo-NHS-LC-Biotin (10 mg, 0.017 mmol) and a drop of triethyl amine was added and stirred for overnight at room temperature. Solvent was evaporated and the residue was purified on flash silica gel column chromatography (CH$_2$Cl$_2$:MeOH:NH$_4$OH=7:1:0.1) to give compound 43 (2.9 mg, 55%). %). $^1$H NMR (CD$_3$OD, 300 MHz) δ 7.99 (s, 1H), 7.29 (s, 1H), 7.19-7.32 (m, 3H), 4.93 (d, J=5.4 Hz, 1H), 4.70-4.80 (m, 2H), 4.36-4.42 (m, 1H), 4.16-4.22 (m, 1H), 3.88 (d, J=6.9 Hz, 1H), 3.42-3.62 (m, 2H), 3.03-3.15 (m, 4H), 2.89 (s, 3H), 2.56-2.86 (m, 6H), 2.41 (t, J=6.6 Hz, 1H), 1.96-2.13 (m, 5H), 1.15-1.16 (m, 14H), 0.74-0.88 (m, 1H). C$_{43}$H$_{57}$ClN$_{11}$O$_7$S (M+H)$^+$ : 906.3852. found 906.3878.

(1'S,2'R,3'S,4'S,5'S)-4'-[6-(3-Chlorobenzylamino)-2-(N-Cyanine(β-aminoethylaminocarbonyl)-1-butynyl)-9-yl]-2',3'-dihydroxybicyclo[3.1.0]hexane-1'-carboxylic acid N-methylamide (44). To a solution of compound 37 (1.69 mg, 0.0029 mmol) in DMF (0.3 mL), Cy5 fluorescent dye (2.36 mg, 0.0029 mmol) and bicarbonate buffer (60 μL) was added and stirred at room temperature for overnight. The reaction mixture was covered with aluminum foil in order to protect from light. Solvent was evaporated and the residue was purified on flash silica gel column chromatography (CH$_2$Cl$_2$:MeOH:NH$_4$OH=3:1:0.1) to give compound 44 (3.2 mg, 89%) as a dark blue syrup. $^1$H NMR (CD$_3$OD, 300 MHz) δ 8.21-8.42 (m, 1H), 8.08 (s, 1H), 7.85-7.93 (m, 2H), 7.29-7.46 (m, 6H), 6.28-6.45 (m, 1H), 5.07 (d, J=6.9 Hz, 1H), 4.84-4.86 (m, 2H), 3.97-4.20 (m, 3H), 3.53 (t, J=6.0 Hz, 2H), 3.12 (t, J=6.0 Hz, 2H), 2.89 (s, 3H), 2.49 (t, J=7.5 Hz, 2H), 2.52-2.64 (m, 2H), 2.01-2.17 (m, 2H), 1.56-1.89 (m, 9H), 1.22-1.49 (m, 10H), 0.86-0.96 (m, 1H).

HRMS calculated for C$_{60}$H$_{68}$Cl$_1$N$_{10}$O$_{11}$S$_2$ (M$^+$): 1203.4199. found 1203.4175.

EXAMPLE 2

This example illustrates some of the biological properties of compounds in accordance with an embodiment of the invention.

[$^{125}$I]N$^6$-(4-amino-3-iodo-benzyl)adenosine-5'-N-methyluronamide ([$^{125}$I]I-AB-MEGA; 2000 Ci/mmol), [$^3$H]R-PIA (R—N$^6$-[phenylisopropyl]adenosine, 34 Ci/mmol), [$^3$H]CGS21680 (2-[p-(2-carboxyethyl)phenylethylamino]-5'-N-ethylcarboxamido-adenosine, 47 Ci/mmol) and [$^3$H]cAMP (40 Ci/mmol) were from Amersham Pharmacia Biotech (Buckinghamshire, UK). NECA, CGS21680, CPA, and R-PIA were purchased from Sigma-RBI (St. Louis, Mo.). Other chemicals were from standard commercial sources and of analytical grade.

CHO cells stably expressing human recombinant ARs were cultured in DMEM and F12 (1:1) supplemented with 10% fetal bovine serum, 100 units/ml penicillin, 100 µg/mL streptomycin, 2 µmol/ml glutamine and 800 µg/ml geneticin. After harvest and homogenization, cells were centrifuged at 500 g for 10 min, and the pellet was re-suspended in 50 mM Tris.HCl buffer (pH 7.4) containing 10 mM MgCl$_2$, 1 mM EDTA. The suspension was homogenized with an electric homogenizer for 10 sec, and was then re-centrifuged at 20,000 g for 20 min at 4° C. The resultant pellets were resuspended in buffer in the presence of 3 Units/ml adenosine deaminase, and the suspension was stored at −80° C. until the binding experiments. The protein concentration was measured as described in Bradford, M. M. et al., *Anal. Biochem.* 1976, 72, 248. For A$_3$AR binding assays, each tube contained 100 µl of membrane suspension, 50 µl of [$^{125}$I]I-AB-MECA (final concentration 0.5 nM), and 50 µl of increasing concentrations of compounds in Tris.HCl buffer (50 mM, pH 7.4) containing 10 mM MgCl$_2$. Nonspecific binding was determined using 10 µM NECA. The mixtures were incubated at 25° C. for 60 min. Binding reactions were terminated by filtration through WHATMAN™ GF/B filters under reduced pressure using a MT-24 cell harvester (Brandell, Gaithersburg, Md.). Filters were washed three times with ice-cold buffer. Radioactivity was determined in a Beckman 5500B γ-counter. The binding of [$^3$H]R-PIA to A$_1$ARs and the binding of [$^3$H]CGS21680 to A$_{2A}$ARs were as previously described.[10] Similar competition binding assays were conducted using HEK 293 cell membranes expressing mouse ARs using [$^{125}$I]I-AB-MECA to label A$_1$ or A$_3$ARs and [$^3$H]CGS 21680 to label A$_{2A}$ARs as described in Kreckler L M et al., *J. Pharmacol. Exp. Ther.* 2006, 317, 172. IC$_{50}$ values were converted to K$_i$ values as described in Cheng Y-C and Prusoff W H., *Biochem. Pharmacol.* 1973, 22, 3099. Data were expressed as mean±standard error and set forth in Table 1.

TABLE 1

Affinity of a series of (N)-methanocarba adenosine derivatives at three subtypes of ARs in various species.

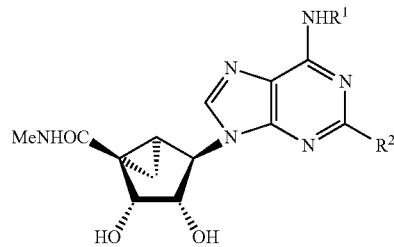

| Cmpd. | R$^1$ | R$^2$ | Species | A$_1$$^a$ K$_i$, nM | A$_2$A$^a$ K$_i$, nM (or % inhib.) | A$_3$$^a$ K$_i$, nM | Selectivity A$_1$/A$_3$ |
|---|---|---|---|---|---|---|---|
| 1 | 3-chlorobenzyl | I | M | 210 ± 34.4 | (40%)$^i$ | 1.18 ± 0.11 | 178 |
|   |   |   | H$^e$ | 2200 | >10000 | 3.6 | 610 |
|   |   |   | R$^e$ | ND | ND | 3.9 | — |
| 2 | 2,5-dimethoxybenzyl | I | M | 293 ± 29 | (14%)$^i$ | 1.51 ± 0.36 | 194 |
|   |   |   | H | 3070 ± 820 | (35%)$^f$ | 1.30 ± 0.27 | 2360 |
| 3 | 3-chlorobenzyl | ethynyl | M | 45.6 ± 7.9 | (41%)$^i$ | 0.85 ± 0.08 | 53.6 |
|   |   |   | H | 174 ± 23 | (48%)$^f$ | 1.30 ± 0.38 | 134 |
| 4 | 3-chlorobenzyl | 2-trimethylsilyl-ethynyl | M | 159 ± 22 | (20%)$^i$ | 4.46 ± 0.57 | 35.6 |
|   |   |   | H | 160 ± 40 | (52%)$^f$ | 0.98 ± 0.14 | 160 |
| 5 | 3-chlorobenzyl | 1-pentynyl | M | 1390 ± 430 | (42%)$^i$ | 6.06 ± 1.21 | 229 |
|   |   |   | H | 1040 ± 83 | (80%)$^f$ | 0.82 ± 0.20 | 1300 |
| 6 | 3-chlorobenzyl | 5-carbomethoxy-1-pentynyl | M | 1340 ± 330 | (50%)$^i$ | 4.65 ± 0.53 | 288 |
|   |   |   | H | 482 ± 23 | (49%)$^f$ | 1.17 ± 0.27 | 412 |
| 7 | 3-chlorobenzyl | 5-carboxy-1-pentynyl | M | 10500 ± 1900 | (8%)$^i$ | 24.4 ± 3.1 | 431 |
|   |   |   | H | 14900 ± 3500 | (43%)$^f$ | 2.38 ± 0.56 | 6260 |
| 8 | 3-chlorobenzyl | 5-(2-aminoethyl)aminocarbonyl-1-pentynyl | M | 546 ± 62 | (31%)$^i$ | 8.60 ± 1.02 | 64 |
|   |   |   | H | 454 ± 44 | (81%)$^f$ | 2.17 ± 0.51 | 209 |
| 9 | 3-(5-carboxy-1-pentynyl)benzyl | Cl | M | 703 ± 71 | (5%)$^i$ | 14.4 ± 2.5 | 49 |
|   |   |   | H | 320 ± 31 | (14%)$^f$ | 17.1 ± 1.2 | 19 |
| 10 | 3-(5-(2-aminoethyl)aminocarbonyl-1-pentynyl)benzyl | Cl | M | 151 ± 18 | (39%) | 11.9 ± 2.4 | 13 |
|   |   |   | H | 271 ± 23 | (58%)$^f$ | 5.21 ± 0.91 | 52 |
| 11 | 3-(5-(2-acetamido-ethyl)aminocarbonyl-1-pentynyl)benzyl | Cl | M | 45.4 ± 3.4 | (68%)$^i$ | 4.65 ± 0.22 | 9.8 |
|   |   |   | H | 181 ± 22 | (80%)$^f$ | 2.88 ± 0.54 | 63 |

TABLE 1-continued

Affinity of a series of (N)-methanocarba adenosine derivatives at three subtypes of ARs in various species.

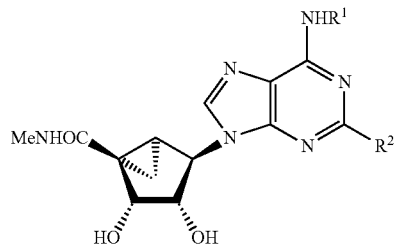

| Cmpd. | R[1] | R[2] | Species | A$_1$[a] K$_i$, nM | A$_2$A[a] K$_i$, nM (or % inhib.) | A$_3$[a] K$_i$, nM | Selectivity A$_1$/A$_3$ |
|---|---|---|---|---|---|---|---|
| 12 | Methyl | Cl | M | 55.3 ± 6.0 | 20400 ± 3200 | 49.0 ± 3.9 | 1.1 |
|  |  |  | H | 2011 ± 1700 | (6%)[d,f] | 2.2 ± 0.6 | 950 |
|  |  |  | R[d,g] | 805[g] | >10,000[g] | 160 ± 30 | 5.0 |
| 13 | 3-Chlorobenzyl | Cl | M | 15.3 ± 5.8 | 10400 ± 1700 | 1.49 ± 0.46 | 10.3 |
|  |  |  | H[c,d] | 260 ± 60 | 2300 ± 100 | 0.29 ± 0.04 | 900 |
|  |  |  | R[d] | ND | ND | 1.0 |  |
| 14 | 3-Bromobenzyl | Cl | M | 8.79 ± 0.12 | 6390 ± 870 | 0.90 ± 0.22 | 9.8 |
|  |  |  | H[c,d] | 270 | 1300 | 0.38 | 710 |
|  |  |  | R[c] | ND | ND | 0.76 | — |
| 15 | 3-Iodobenzyl | Cl | M | 7.32 ± 1.5 | 5350 ± 860 | 0.80 ± 0.14 | 9.2 |
|  |  |  | H[c] | 136 ± 22 | 784 ± 97 | 1.5 ± 0.2 | 100 |
|  |  |  | R | 83.9 g | 1660[g] | 1.1 | 76 |
| 16 | 3-(3-Hydroxy-1-propynyl)benzyl | Cl | M | 111 ± 22 | (11%)[i] | 1.94 ± 1.1 | 57.2 |
|  |  |  | H[d] | 2600 ± 300 | (56%)[f] | 2.9 ± 0.7 | 900 |
|  |  |  | R[d] | ND | ND | 1.6 ± 0.6 |  |
| 17 | 2,5-Dimethoxybenzyl | Cl | M | 29.0 ± 3.3 | 44700 ± 5700 | 1.72 ± 0.04 | 17 |
|  |  |  | H[c,d] | 1600 | 10000 | 1.4 | 1100 |
|  |  |  | R[d] | ND | ND | 0.87 |  |
| 18 | 2,2-Diphenylethyl | Cl | M | 6.83 ± 1.5 | 1810 ± 581 | 1.67 ± 0.09 | 4.1 |
|  |  |  | H[c,e] | 1300 ± 100 | 1600 ± 100 | 0.69 ± 0.02 | 1900 |
|  |  |  | R[c] | ND | ND | 10 ± 4 |  |
| 19 | Cyclopropylphenyl | Cl | M | 6.60 ± 1.3 | 38200 ± 5300 | 2.79 ± .089 | 2.4 |
|  |  |  | H[c,d] | 770 ± 50 | 4800 ± 200 | 0.78 ± 0.06 | 990 |
| 20 | 3-Chlorobenzyl | SMe | M | 98.9 ± 18.8 | (32%)[i] | 1.19 ± 0.09 | 83 |
|  |  |  | H[c] | 610 | 10000 | 1.5 | 410 |
| 21 | Methoxy | Cl | M | 1160 ± 130 | (2%)[i] | 877 ± 149 | 1.3 |
|  |  |  | H | 265 ± 45 | (2%)[f] | 149 ± 15 | 1.8 |
| 31 | 3-Iodobenzyl | H | H | 700 ± 270 | 6200 ± 100 | 2.4 ± 0.5 | 100[j] |
| 32 | cyclopentyl | Cl | H | 18.3 ± 6.3 | 3250 ± 300 | 3.7 ± 0.9 | 101[j] |
| 33 | 3-Chlorobenzyl | C≡C(CH$_2$)$_2$COOH | H | (17 ± 3%) | (24 ± 12%) | 61.1 ± 35.8 | 106.2 ± 17.7[j] |
| 34 | 3-Chlorobenzyl | C≡C(CH$_2$)$_4$COOH | H | (5 ± 3%) | (38 ± 2%) | 12.4 ± 1.8 | ND |
| 35 | 3-Chlorobenzyl | C≡C(CH$_2$)$_2$COOCH+hd 3 | H | (19 ± 3%) | (43 ± 5%) | 5.5 ± 0.3 | 74.4 ± 5.1[j] |
| 36 | 3-Chlorobenzyl | C≡C(CH$_2$)$_4$COOCH+hd 3 | H | (21 ± 8%) | 3540 ± 1370 | 11.1 ± 2.3 | 90.0 ± 6.2[j] |
| 37 | 3-Chlorobenzyl | C≡C(CH$_2$)$_2$CONH(CH$_2$)$_2$NH$_2$ | H | (25 ± 12%) | 550 ± 83 | 2.5 ± 0.5 | ND |
| 38 | 3-Chlorobenzyl | C≡C(CH$_2$)$_4$CONH(CH$_2$)$_2$NH$_2$ | H | (21 ± 6%) | 277 ± 33 | 3.4 ± 0.7 | 100.0 ± 2.4[j] |
| 39 | 3-Chlorobenzyl | C≡C(CH$_2$)$_2$CONH(CH$_2$)$_3$NH$_2$ | H | (16 ± 4%) | 979 ± 181 | 3.1 ± 0.4 | 97.9 ± 18.4[j] |
| 40 | 3-Chlorobenzyl | C≡C(CH$_2$)$_2$CONH(CH$_2$)$_4$NH$_2$ | H | (30 ± 7%) | 766 ± 109 | 2.1 ± 0.4 | 102.1 ± 13.0[j] |
| 41 | 3-Chlorobenzyl | C≡C(CH$_2$)$_2$CO[NH(CH$_2$)$_2$]$_2$NH$_2$ | H | (14 ± 8%) | 890 ± 110 | 15.4 ± 4.4 | 87.6 ± 21.2[j] |
| 42 | 3-Chlorobenzyl | C≡C(CH$_2$)$_2$CONH(CH$_2$)$_2$NH-biotin | H | (13 ± 6%) | (51 ± 2%) | 36.4 ± 5.6 | 84.5 ± 12.0[j] |
| 43 | 3-Chlorobenzyl | C≡C(CH$_2$)$_2$CONH(CH$_2$)$_2$NH—CO(CH$_2$)$_5$NH-biotin | H | (8 ± 4%) | (47 ± 11%) | 57.7 ± 16.2 | 106.5 ± 17.7[j] |
| 44 | 3-Chlorobenzyl | C≡C(CH$_2$)$_2$CONH(CH$_2$)$_2$NH—CO—(CH$_2$)$_5$Cy5 | H | (10 ± 4%) | 4730 ± 1020 | 17.2 ± 3.1 | 94.4 ± 9.6[j] |

[a]Competition radioligand binding assays using [$^{125}$I]N$^6$-(4-amino-3-iodobenzyl)adenosine-5'-N-methyl-uronamide (A$_1$ and A$_3$ARs) and [$^3$H]2-[p-(2-carboxyethyl)phenyl-ethylamino]-5'-N-ethylcarboxamidoadenosine (A$_{2A}$AR) were conducted with membranes prepared from HEK293 cells expressing recombinant mouse A$_1$, A$_{2A}$, or A$_3$ARs. At rat and human ARs, the A$_1$ radioligand was either [$^3$H]R-phenylisopropyladenosine or [$^3$H]2-chloro-N$^6$-cyclopentyladenosine. Values are expressed as the mean ± SEM. ND, not determined.
[b]Data from Ge et al. (J. Pharmacol. Exp. Ther., 2006, 319, 1200).
[c]EC$_{50}$ value in activation of the A$_{2B}$AR is ≥10 μM.
[d]Data from Tchilibon et al. (J. Med. Chem., 2005, 48, 1745).
[e]Data from Kim et al. (J. Med. Chem., 1994, 37, 3614).
[f]Percent Inhibition at 10 μM.
[g]Data from Lee et al. (Bioorg. Med. Chem. Lett., 2001, 11, 1333).
[i]Percent Inhibition at 100 μM.
[j]% Efficacy at the human A$_3$ AR was determined by inhibition of forskolin-stimulated cyclic AMP production in AR transfected CHO cells.
Data are at 10 μM in comparison to the maximal effect of a full agonist (5'-N-ethylcarboxamidoadenosine) at 100%.

EXAMPLE 3

This example demonstrates a method of preparing compounds in accordance with an embodiment of the invention. D-ribose was protected with TBDPS-Cl followed by alkaline hydrolysis, thus providing acid 102. Reductive decarboxylation of acid 102 was carried out using non-toxic tris(trimethylsilyl)silane as a hydrogen donor and produced the silyl ether 103 in 40% yield. The silyl ether 103 was deprotected with TBAF. The resultant alcohol 104 was converted into a key dichloropurine derivative 106 through a Mitsonobu reaction (FIG. 4). Derivative 106 reacted with an excess of the corresponding primary amine to give the $N^6$ substituted and 2',3'-isopropylidene protected derivatives compounds 117a-113a, followed by acid catalyzed deprotection to give the $N^6$-3-halobenzyl and related arylmethyl derivatives 107b-113b.

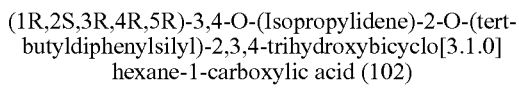

(1R,2S,3R,4R,5R)-3,4-O-(Isopropylidene)-2-O-(tert-butyldiphenylsilyl)-2,3,4-trihydroxybicyclo[3.1.0]hexane-1-carboxylic acid (102)

tert-Butyldiphenylsilyl chloride (2.70 g, 10 mmol) and triethylamine (2.0 g, 20 mmol) were added to a solution of alcohol 101 (prepared from D-ribose following the standard procedure (Joshi et al. supra) 1.22 g, 5 mmol) and imidazole (140 mg, 2 mmol) in DMF (3 mL) while stirring at room temperature. The solution was stirred at 60° C. for 16 h. The reaction mixture was cooled to room temperature and diluted with a 4:1 ethyl acetate-hexane mixture (50 mL), washed with water, dried, and solvent was evaporated. The residue was purified by flash chromatography (0 to 10% ethyl-acetate-hexane) to give ethyl (1R,2S,3R,4R,5R)-2,3-O-(isopropylidene)-4-O-(tert-butyldiphenylsilyl)-2,3,4-trihydroxybicyclo[3.1.0]hexane-1-carboxylate. The compound was dissolved in MeOH (5 mL), 2N aq. NaOH (5 mL) was added, and the reaction mixture was refluxed for 2 h. The reaction mixture was neutralized with $NaH_2PO_4$, and extracted with DCM. The combined DCM solutions were dried and evaporated, and the residue was purified by flash chromatography to give title compound 102 (1.65 g, 73%). $^1H$ NMR (CDCl$_3$), δ: 7.72 (d, 4H, J=7.8 Hz), 7.39 (m, 6H), 5.05 (d, 1H, J=6.3 Hz), 4.43 (t, 1H, J=6.0 Hz), 4.08 (t, 1H, J=6.6 Hz), 2.26 (m, 1H), 1.97 (s, 3H), 1.56 (s, 3H), 1.52 (m, 1H), 1.21 (s, 3H), 1.08 (s, 9H).

(1S,2S,3R,4R,5R)-3,4-O-(Isopropylidene)-2-O-(tert-butyldiphenylsilyl)-2,3,4-trihydroxybicyclo[3.1.0]hexane (103)

A 1M solution of DCC in oxygen-free toluene (0.96 mL) was added to a solution of acid 102 (363 mg, 0.80 mmol), 2-mercaptopyridine N-oxide (112 mg, 0.88 mmol), and AIBN (40 mg, 0.24 mmol) in dry oxygen-free toluene (4 mL). The reaction mixture was stirred for 4 h at 25° C., tris(trimethylsilyl)silane (0.50 mL, 1.6 mmol) was added, and the reaction mixture was heated at 85° C. for 4 h. The reaction mixture was evaporated, and the residue was separated by flash chromatography (0 to 10% ethyl acetate-hexane mixture) to afford the title compound 103 (121 mg, 40%). $^1H$ NMR (CDCl$_3$), δ: 7.76 (d, 4H, J=7.8 Hz), 7.39 (m, 6H), 4.66 (t, 1H, J=6.0 Hz), 4.44 (t, 1H, J=6.6 Hz), 4.03 (t, 1H, J=6.6 Hz), 1.6 (m, 1H), 1.57 (s, 3H), 1.45 (m, 1H), 1.33 (s, 1H), 1.20 (s, 3H), 1.09 (s, 9H), 0.58 (m, 1H).

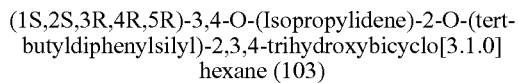

(1R,2R,3S,4S,5S)-2,3-O-(Isopropylidene)-2,3,4-trihydroxy-bicyclo[3.1.0]hexane (104), Method B A 1M solution of tert-butylammonium fluoride in THF (1 mL) was added to a solution of silylether 103 (102 mg, 0.25 mmol) in THF (1 mL). The reaction mixture was left at 20° C. for 16 h and evaporated. The residue was diluted with ethyl acetate (20 mL) and washed with a small amount of brine. The ethyl acetate solution was dried and evaporated, and the residue was purified by flash chromatography to afford the title compound 104 (33 mg, 84%). $^1H$ NMR and MS are provided under Method A.

General Procedure for Preparation of Compounds 107b-113b.

An amine (RNH$_2$ in Scheme 3, 0.5 mmol) was added to a solution of 106 (20 mg, 0.06 mmol) in DCM (0.1 mL). The reaction mixture was stirred at room temperature for 16 h. The solvent was removed under vacuum, and the residue was separated by flash chromatography (30 to 100% ethyl acetate-hexane) to afford the corresponding 6-alkylaminopurine derivative that was dissolved in a mixture of MeOH (4 mL), TFA (0.2 mL) and water (2 mL). The reaction mixture was stirred at 70° C. for 16 h, and then evaporated. The residue was evaporated twice with water, and the residue was purified by flash chromatography (50 to 100% ethyl acetate).

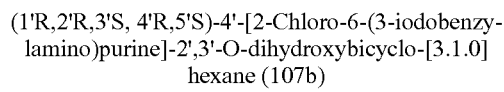

(1'R,2'R,3'S, 4'R,5'S)-4'-[2-Chloro-6-(3-iodobenzylamino)purine]-2',3'-O-dihydroxybicyclo-[3.1.0]hexane (107b)

Yield 15 mg (51% $^1H$ NMR (CD$_3$OD), δ: 8.16 (s, 1H), 7.49 (s, 1H), 7.60 (d, 1H, 8.5 Hz), 7.40 (d, 1H, 8.5 Hz), 7.10 (t, 1H, 8.5 Hz), 4.71 (s, 2H), 3.90 (d, 3.3 Hz, 1H), 3.65 (s, 1H), 2.05-1.95 (m, 1H), 1.67-1.63 (m, 1H), 1.36 (s, 1H), 1.31-1.27 (m, 1H), 0.95-0.87 (m, 1H), 0.77-0.75 (m, 1H). HRMS calculated for $C_{18}H_{18}Cl_1N_5O_2^+$ (M+H)$^+$ : 498.0194. found, 498.0194. HPLC: RT 21.6 min (98%) in solvent system A, 17.0 min (98%) in system B.

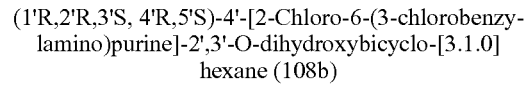

(1'R,2'R,3'S, 4'R,5'S)-4'-[2-Chloro-6-(3-chlorobenzylamino)purine]-2',3'-O-dihydroxybicyclo-[3.1.0]hexane (108b)

Yield 58%. $^1H$ NMR (CD$_3$OD), δ: 8.16 (br. s., 1H), 7.41 (s, 1H), 7.29 (m, 3H), 4.79 (s, 1H), 4.75 (br. s, 2H), 4.70 (br. t., 1H, J=5.4 Hz), 3.86 (d, 1H, J=6.6 Hz), 1.97 (m, 1H), 1.65 (m, 1H), 1.30 (m, 1H), 0.75 (m, 1H). HRMS (ESI MS m/z): calculated for $C_{18}H_{18}Cl_2N_5O_2^+$ (M+H)$^+$ , 406.0832. found, 406.0825. HPLC RT 20.3 min (98%) in solvent system A, 15.6 min (98%) in system B.

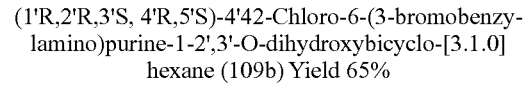

(1'R,2'R,3'S, 4'R,5'S)-4'42-Chloro-6-(3-bromobenzylamino)purine-1-2',3'-O-dihydroxybicyclo-[3.1.0]hexane (109b) Yield 65%

$^1H$ NMR (CD$_3$OD): 8.03 (s, 1H), 7.45 (s, 1H), 7.29 (m, 2H), 7.12 (t, 1H, J=7.8 Hz), 4.68 (s, 1H), 4.63 (br. s, 2H), 4.59 (br. t., 1H, J=5.4 Hz), 3.79 (d, 1H, J=6.6 Hz), 1.86 (m, 1H), 1.55 (m, 1H), 1.20 (m, 1H), 0.64 (m, 1H). HRMS (ESI MS m/z) calculated for $C_{18}H_{18}BrClN_5O_2^+$ (M+H)$^+$ , 450.0327. found 450.0315. HPLC RT 20.74 min (98%) in solvent system A, 16.1 min (99%) in system B.

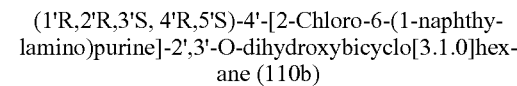

(1'R,2'R,3'S, 4'R,5'S)-4'-[2-Chloro-6-(1-naphthylamino)purine]-2',3'-O-dihydroxybicyclo[3.1.0]hexane (110b)

Yield 48%. $^1H$ NMR (CD$_3$OD): 8.13 (br. d., 2H, J=7.8 Hz), 7.84 (m, 2H), 7.49 (m, 4H), 5.21 (s, 1H), 4.79 (br. s, 1H), 4.78 (br. s, 2H), 4.67 (br. t., 1H, J=5.1 Hz), 3.88 (d, 1H, J=6.6 Hz), 1.93 (m, 1H), 1.62 (m, 1H), 1.25 (m, 1H), 0.73 (m, 1H). HRMS (ESI MS m/z) calculated for $C_{22}H_2ClN_5O_2^+$ (M+H)+, 422.1378. found 422.1385. HPLC RT 21.5 min (97%) in solvent system A, 17.0 min (98%) in system B.

(1'R,2'R,3'S, 4'R,5'S)-4'-[2-Chloro-6-(2,5-dimethoxybenzylamino)purine]-2',3'-O-dihydroxybicyclo-[3.1.0]hexane (111b)

Yield 44%. $^1$H NMR (CD$_3$OD): 8.4 (very br. s, 1H), 6.95 (s, 1H, J=2.7 Hz), 6.89 (d, 1H, J=9.3 Hz), 6.78 (dd, 1H, J=2.7, 9.0 Hz), 4.80 (s, 1H), 4.75 (br. m, 3H), 3.87 (d, 1H, J=6.3 Hz), 3.83 (s, 3H), 3.71 (s, 3H), 1.95 (m, 1H), 1.64 (m, 1H), 1.29 (m, 1H), 0.74 (m, 1H). HRMS (ESI MS m/z) calculated for $C_{20}H_{23}ClN_5O_4^+$ (M+H)+, 432.1433. found 432.1439. HPLC RT 18.7 min (98%) in solvent system A, 16.6 min (98%) in system B.

(1'R,2'R,3'S, 4'R,5'S)-4'42-Chloro-6-(2-hydroxy-5-methoxybenzylamino)purine-1-2',3'-O-dihydroxybicyclo-[3.1.0]hexane (112b)

Yield 39%. $^1$H NMR (CD$_3$OD): 8.07 (s, 1H), 6.60-6.82 (m, 3H), 4.69 (s, 1H), 4.59 (br. t., 1H, J=6.0 Hz), 4.56 (br. s, 2H), 3.79 (d, 1H, J=6.6 Hz), 3.61 (s, 3H) 1.86 (m, 1H), 1.55 (m, 1H), 1.20 (m, 1H), 0.65 (m, 1H). HRMS (ESI MS m/z) calculated for $C_{19}H_{21}ClN_5O_4^+$ (M+H)+, 418.1277. found, 418.1277. HPLC RT 16.0 min (100%) in solvent system A, 11.0 min (98%) in system B.

(1'R,2'R,3'S, 4'R,5'S)-4'-[2-Chloro-6-(trans-2-phenylcyclopropylamino)purine]-2',3'-O-dihydroxybicyclo-[3.1.0]hexane (113b)

Yield 52%. $^1$H NMR (CD$_3$OD): 8.16 (very br. s., 1H), 7.0-7.48 (m, 5H), 4.79 (s, 1H), 4.68 (br. s, 2H), 3.88 (d, 1H, J=5.7 Hz), 2.17 (m, 1H) 1.97 (m, 1H), 1.65 (m, 1H), 1.29 (m, 2H), 0.74 (m, 1H). HRMS (ESI MS m/z) calculated for $C_{20}H_{21}ClN_5O_2^+$ (M+H)+, 398.1378. found, 398.1372. HPLC RT 20.3 mM (99%) in solvent system A, 15.6 min (98%) in system B.

EXAMPLE 4

This Example illustrates the ability of the compounds in accordance with an embodiment of the invention to bind to $A_3$ adenosine receptors. The binding affinity values are set forth in Table 2.

Receptor Binding and Functional Assays

[$^{125}$I]N$^6$-(4-Amino-3-iodobenzyl)adenosine-5'-N-methyluronamide (1-AB-MECA; 2000 Ci/mmol), [$^3$H]cyclic AMP (40 Ci/mmol), and other radioligands were purchased from Perkin-Elmer Life and Analytical Science (Boston, Mass.). [$^3$H]CCPA (2-chloro-N$^6$-cyclopentyladenosine) was a custom synthesis product (Perkin Elmer). Test compounds were prepared as 5 mM stock solutions in DMSO and stored frozen.

Cell culture and membrane preparation: CHO (Chinese hamster ovary) cells expressing the recombinant human $A_3$AR were cultured in DMEM (Dulbecco's modified Eagle's medium) supplemented with 10% fetal bovine serum, 100 units/mL penicillin, 100 µg/mL streptomycin, 2 µmol/mL glutamine and 800 µg/mL geneticin. The CHO cells expressing rat $A_3$ARs were cultured in DMEM and F12 (1:1). Cells were harvested by trypsinization. After homogenization and suspension, cell membranes were centrifuged at 500 g for 10 min, and the pellet was re-suspended in 50 mM Tris.HCl buffer (pH 8.0) containing 10 mM MgCl$_2$, 1 mM EDTA and 0.1 mg/mL CHAPS (3[(3-cholamidopropyl)dimethylammonio]-propanesulfonic acid). The suspension was homogenized with an electric homogenizer for 10 sec, and was then re-centrifuged at 20,000 g for 20 min at 4° C. The resultant pellets were resuspended in buffer in the presence of adenosine deaminase (3 Units/mL), and the suspension was stored at −80° C. until the binding experiments. The protein concentration was measured using the Bradford assay. Bradford, M. M. *Anal. Biochem.* 1976, 72, 248.

Binding assays at the $A_1$ and $A_{2A}$ receptors: For binding to human $A_1$ receptors, see (a) Schwabe, U.; Trost, T. Naunyn-Schmiedeberg's *Arch. Pharmacol.* 1980, 313, 179. (b) Perreira, M.; Jiang, J. K.; Klutz, A. M.; Gao, Z. G.; Shainberg, A.; Lu, C.; Thomas, C. J.; Jacobson, K A. *J. Med. Chem.* 2005, 48, 4910.

[$^3$H]R-PIA (N$^6$-[(R)-phenylisopropyl]adenosine, 2 nM) or [$^3$H]CCPA (0.5 nM) was incubated with membranes (40 µg/tube) from CHO cells stably expressing human $A_1$ receptors at 25° C. for 60 min in 50 mM Tris.HCl buffer (pH 7.4; MgCl$_2$, 10 mM) and increasing concentrations of the test ligand in a total assay volume of 200 µA Nonspecific binding was determined using 10 µM of CPA (N$^6$-cyclopentyladenosine). For human $A_{2A}$ receptor binding (Jarvis, M. F.; Schutz, R.; Hutchison, A. J.; Do, E.; Sills, M. A.; Williams, M. J. *Pharmacol. Exp. Ther.* 1989, 251, 888-893) membranes (20 µg/tube) from HEK-293 cells stably expressing human $A_{2A}$ receptors were incubated with [$^3$H]CGS21680 (2-[p-(2-carboxyethyl)phenyl-ethylamino]-5'-N-ethylcarboxamido-adenosine, 15 nM) and increasing concentrations of the test ligand at 25° C. for 60 min in 200 µl 50 mM Tris.HCl, pH 7.4, containing 10 mM MgCl$_2$. NECA (10 µM) was used to define nonspecific binding. The reaction was terminated by filtration with GF/B filters.

Binding assay at the human $A_3$ receptor: For the competitive binding assay, each tube contained 50 µL membrane suspension (20 µg protein), 25 µL of [$^{125}$I]I-AB-MECA (1.0 nM), Olah, M. E., Gallo-Rodriguez, C., Jacobson, K. A., Stiles, G. L. *Mol. Pharmacol.* 1994, 45, 978, and 25 µL of increasing concentrations of the test ligands in Tris.HCl buffer (50 mM, pH 8.0) containing 10 mM MgCl$_2$, 1 mM EDTA. Nonspecific binding was determined using 10 µM of Cl-IB-MECA in the buffer. The mixtures were incubated at 37° C. for 60 min. Binding reactions were terminated by filtration through Whatman GF/B filters under reduced pressure using a MT-24 cell harvester (Brandell, Gaithersburgh, Md., USA). Filters were washed three times with 9 mL ice-cold buffer. Radioactivity was determined in a Beckman 5500B γ-counter. IC$_{50}$ values were converted to K$_i$ values as described in Cheng, Y.; Prusoff, W. H. *Biochem. Pharmacol.* 1973, 22, 3099.

Cyclic AMP accumulation assay: Intracellular cyclic AMP levels were measured with a competitive protein binding method. Nordstedt, C.; Fredholm, B. B. *Anal. Biochem.* 1990, 189, 231; Post, S. R.; Ostrom, R. S.; Insel, P. A. *Methods Mol. Biol.* 2000, 126, 363.

CHO cells that expressed the recombinant human or rat $A_3$AR or the human $A_1$ or $A_{2B}$AR were harvested by trypsinization. After centrifugation and resuspended in medium, cells were planted in 24-well plates in 1.0 mL medium. After 24 h, the medium was removed and cells were washed three times with 1 mL DMEM, containing 50 mM HEPES, pH 7.4. Cells were then treated with the agonist NECA and/or test compound (e.g. 7b) in the presence of rolipram (10 µM) and adenosine deaminase (3 units/mL). After 45 mM forskolin (10 µM) was added to the medium, and incubation was continued for an additional 15 min. The reaction was terminated by removing the supernatant, and cells were lysed upon the addition of 200 µL of 0.1 M ice-cold HCl.

The cell lysate was resuspended and stored at −20° C. For determination of cyclic AMP production, protein kinase A (PKA) was incubated with [$^3$H]cyclic AMP (2 nM) in $K_2HPO_4$/EDTA buffer ($K_2HPO_4$, 150 mM; EDTA, 10 mM), 20 μL of the cell lysate, and 30 μL 0.1 M HCl or 50 μL of cyclic AMP solution (0-16 pmol/200 μL for standard curve). Bound radioactivity was separated by rapid filtration through Whatman GF/C filters and washed once with cold buffer. Bound radioactivity was measured by liquid scintillation spectrometry.

[$^{35}$S]GTPγS binding assay: [$^{35}$S]GTPγS binding was measured by a variation of the method described. (a) Lorenzen, A.; Lang H.; Schwabe U. *Biochem. Pharmacol.* 1998, 56, 1287. (b) Jacobson, K. A.; Ji, X.-d.; Li, A. H.; Melman, N.; Siddiqui, M. A.; Shin, K. J.; Marquez, V. E.; Ravi, R. G. *J. Med. Chem.* 2000, 43, 2196. Each assay tube consisted of 200 μL buffer containing 50 mM Tris HCl (pH 7.4), 1 mM EDTA, 1 mM $MgCl_2$, 1 μM GDP, 1 mM dithiothreitol, 100 mM NaCl, 3 U/ml ADA, 0.2 nM [$^{35}$S]GTPγS, 0.004% 3-[(3-cholamidopropyl)dimethylammonio]propanesulfonate (CHAPS), and 0.5% bovine serum albumin. Incubations were started upon addition of the membrane suspension (CHO cells stably expressing either the native human $A_1AR$ or $A_3AR$, 5 μg protein/tube) to the test tubes, and they were carried out in duplicate for 30 min at 25° C. The reaction was stopped by rapid filtration through Whatman GF/B filters, pre-soaked in 50 mM Tris HCl, 5 mM $MgCl_2$ (pH 7.4) containing 0.02% CHAPS. The filters were washed twice with 3 mL of the same buffer, and retained radioactivity was measured using liquid scintillation counting. Non-specific binding of [$^{35}$S]GTPγS was measured in the presence of 10 μM unlabelled GTPγS. None of the compounds>10% stimulation; thus, they are antagonists of the $A_3$ adenosine receptor.

TABLE 2

Affinity data for compounds in accordance with an embodiment of the invention.

| | In Formula I, $R^2$ = Cl, $R^3$ and $R^4$ = OH and $R^5$ = H | Affinity ($K_i$ nM) or % inhibition[a] | | | % Efficacy[b] |
|---|---|---|---|---|---|
| Compound | $R^1$ | $A_1$ | $A_{2A}$ | $A_3$ | $A_3$ |
| 107b | 3-I-Phenyl-$CH^2$ | 3040 ± 610 | 1080 ± 310 | 1.44 ± 0.60 | 1.0 ± 3.2 |
| 108b | 3-Cl-Phenyl-$CH^2$ | 3070 ± 1500 | 4510 ± 910 | 1.06 ± 0.36 | 2.9 ± 3.7 |
| 109b | 3-Br-Phenyl-$CH^2$ | 1760 ± 1010 | 1600 ± 480 | 0.73 ± 0.30 | 5.8 ± 0.8 |
| 110b | 1-Naphthyl-$CH^2$ | 1120 ± 640 | 1530 ± 350 | 1.42 ± 0.12 | 3.1 ± 0.3 |
| 111b | 2,5-diMeO-Ph-$CH^2$ | 3000 ± 1260 | 2620 ± 730 | 1.58 ± 0.56 | 4.6 ± 3.8 |
| 112b | 2-OH-5-MeO-Ph-$CH^2$ | 1110 ± 300 | 6870 ± 1440 | 4.06 ± 0.35 | 0.4 ± 1.3 |
| 113b | trans-2-Ph-cyclopropyl | 1790 ± 1430 | 2010 ± 890 | 1.30 ± 0.39 | 9.7 ± 4.1 |

[a]All experiments were done on CHO or HEK ($A_{2A}$ only) cells stably expressing one of four subtypes of human ARs. The binding affinity for $A_1$, $A_{2A}$ and $A_3$ARs was expressed as $K_i$ values (n = 3-5) and was determined by using agonist radioligands ([$^3$H]CCPA or ([$^3$H]R-PIA), ([$^3$H]CGS21680), [$^{125}$I]I-AB-MECA, respectively. The potency at the $A_{2B}$AR was expressed as $EC_{50}$ values and was determined by stimulation of cyclic AMP production in AR-transfected CHO cells. A percent in parentheses refers to inhibition of radioligand binding at 10 μM.
[b]measured by [$^{35}$S]GTPγS binding assay.

In accordance with one method of biological assay, compounds 107b-109b (3-halobenzyl) in the (N)-methanocarba series were potent $A_3$ AR antagonists with binding $K_i$ values of 0.7-1.4 nM. Compound 109b (3-bromobenzyl analogue) proved to be the most potent $A_3AR$ antagonist of this series in binding with a $K_i$ value of 0.73 nM, and it displayed high selectivity (2400-fold and 2190-fold in comparison to the $A_1$ and $A_{2A}AR$, respectively). The most $A_3AR$ selective compound was the 3-chloro analogue 108b with 2900-fold and 4250-fold selectivity in comparison to the $A_1$ and $A_{2A}AR$, respectively. The SAR of substitution of the $N^6$-benzyl group further showed that dimethoxy substitution (111b), fusion of the phenyl ring to a second ring (110b), and extension by one carbon (i.e., in the rotationally constrained 2-phenylcyclopropyl analogue, 113b) were all tolerated with nanomolar binding affinity at the $A_3AR$. Compound 112b, a demethylated analogue of 11b, was slightly less potent in binding to the $A_3AR$.

Figure 7:
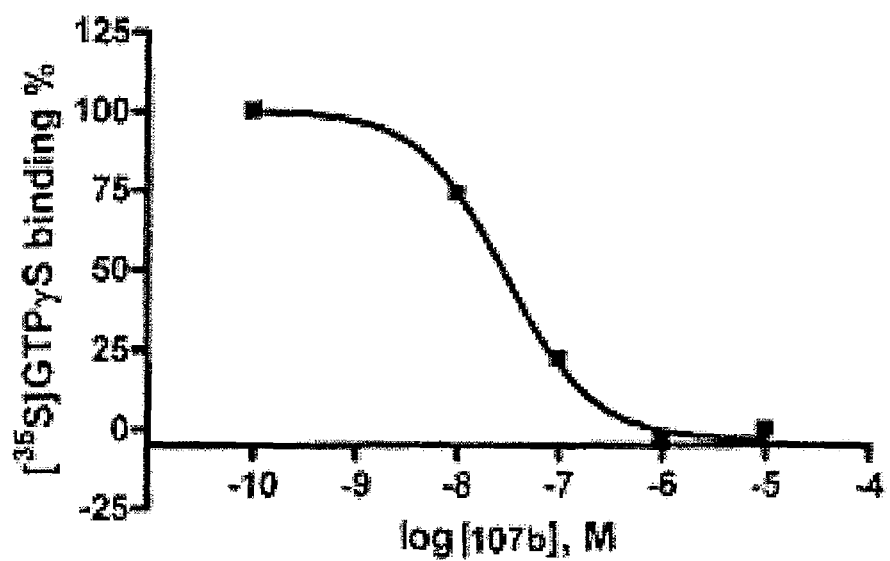
FIG. 7 depicts functional antagonism by the compound 107b of the invention in the guanine nucleotide binding assay ([$^{35}$S]GTPγS) in membranes of CHO cells expressing human A$_3$AR.
Figure 8:
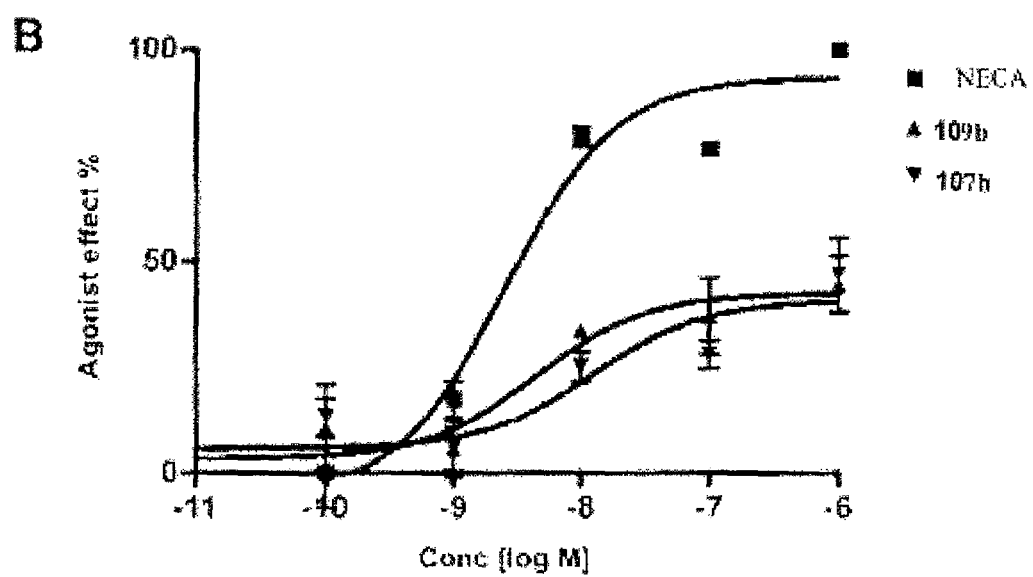
FIG. 8 depicts functional agonism of compounds 107b and 109b in accordance with an embodiment of the invention in an assay of adenylate cyclase membranes of CHO cells expressing hA$_3$AR. The full agonist NECA (5'-N-ethylcarboxamidoadenosine), representing 100% efficiency, is shown comparison.
Figure 9:
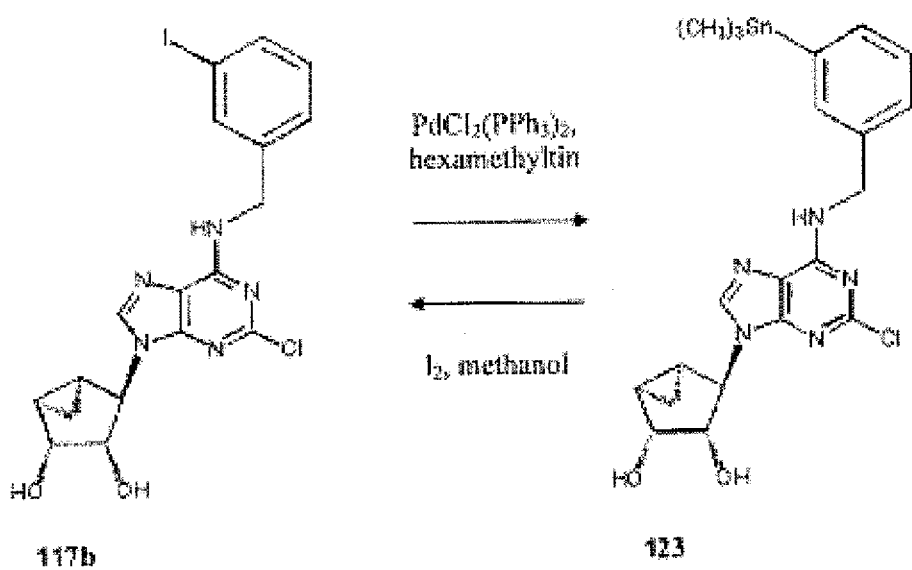
FIG. 9 depicts the conversion of iodo compound 117b into trimethylstannylated compound 123.

In a functional assay of [$^{35}$S]GTPγS binding induced by $A_3AR$ activation, 107b completely inhibited stimulation by 1 μM NECA (5'-N-ethylcarboxamidoadenosine) with an $IC_{50}$ of 29.8 nM (FIG. 7). Schild analysis of the right shifts by 107b of the response curves in the inhibition of adenylate cyclase by NECA provided a $K_B$ value of 8.9 nM.

When compared in the ability to stimulate the $A_3AR$ using multiple functional criteria, different results were obtained. In the cAMP assays, compounds 107b and 109b exhibited partial agonism at $A_3AR$ with percent relative efficacies of 44±6 and 46±4, respectively, and the $EC_{50}$ values were respectively, 12±1 and 4.2±0.6 nM.

EXAMPLE 5

This example illustrates a method of preparing a radioiodinated compound in accordance with an embodiment of the invention. Compound 107b having $^{125}$I was prepared as follows. The (radio)iodination of compound 107b on its $N^6$-3-iodobenzyl substituent was accomplished in high yield by iododestannylation of a 3-(trimethylstannyl)benzyl precursor through a "cold" iodination reaction.

Materials and Instrumentation.

Hexamethyltin and other reagents, including pharmacological agents, were purchased from Sigma-Aldrich Chemical Company, except where noted. Sodium [$^{125}$I]iodide (17.4 Ci/mg) in NaOH (1.0×10$^{−5}$ M) was supplied by Perkin-Elmer Life and Analytical Science. $^1$H NMR spectra were obtained with a Varian Gemini 300 spectrometer using $CDCl_3$ and $CD_3OD$ as solvents. Chemical shifts are expressed in δ values (ppm) with tetramethylsilane (δ 0.00) for $CDCl_3$ and water (δ 3.30) for $CD_3OD$. TLC analysis was carried out on aluminum sheets precoated with silica gel $F_{254}$ (0.2 mm) from Aldrich. HPLC mobile phases consisted of $CH_3CN$/tetrabutyl ammonium phosphate (5 mM) from 20/80 to 60/40 in 20 min, flow rate 1.0 ml/min. High-resolution mass measurements were performed on Micromass/Waters LCT Premier Electrospray Time of Flight (TOF) mass spectrometer coupled with a Waters HPLC system.

Preparation of 123: (1'R,2'R,3'S, 4'R,5'S)-4'-[2-Chloro-6-(3-trimethylstannylbenzylamino)purine]-2', 3'-O-dihydroxybicyclo-[3.1.0]hexane (101)

107b (8.95 mg, 0.018 mmol), $PdCl_2(PPh_3)_2$ (2.7 mg), and hexamethyltin (11 μL, 0.054 mmol) were mixed together in anhydrous dioxane (2 ml), and the resulting reaction mixture was stirred at 70° C. for 2 h. The mixture was concentrated under reduced pressure. The product was purified by flash chromatography by using $CHCl_3$: MeOH (10:1) as the eluant to afford the stannyl derivative 123 (9.3 mg, 90%) as an oil. $^1$H NMR (300 MHz, $CDCl_3$), 7.81 (s, 1H), 7.53 (s, 1H), 7.34 (m, 2H), 7.33 (m, 1H), 6.49 (br s, 1H), 4.88 (br s, 2H), 4.00 (m, 2H), 3.71 (s, 1H), 3.65 (m, 1H), 3.47 (m, 1H), 2.02 (m, 1H), 1.96 (s, 1H), 1.64 (m, 1H), 1.28 (m, 2H), 0.81 (m, 1H), 0.29 (s, 9H). HRMS (M+1)$^+$: calculated for $C_{21}H_{27}ClIN_5O_2Sn^+$ (M+H)$^+$535.6338. found 536.0823 HPLC: Rt=22.1 min. HPLC system: 5 mM TBAP/CH$_3$CN from 80/20 to 60/40 in 25 min, then isocratic for 2 min; flow rate of 1 ml/min.

The trimethylstannyl intermediate 123 (0.1 mg) was reacted sodium [$^{125}$I] iodide in NaOH (1.0×10$^{-5}$ M) to obtain [$^{125}$I] 107b, following the procedure disclosed in Vaidyanathan G., et al., *Nat. Protocols* 1: 707-713 (2006).

Figure 10A:
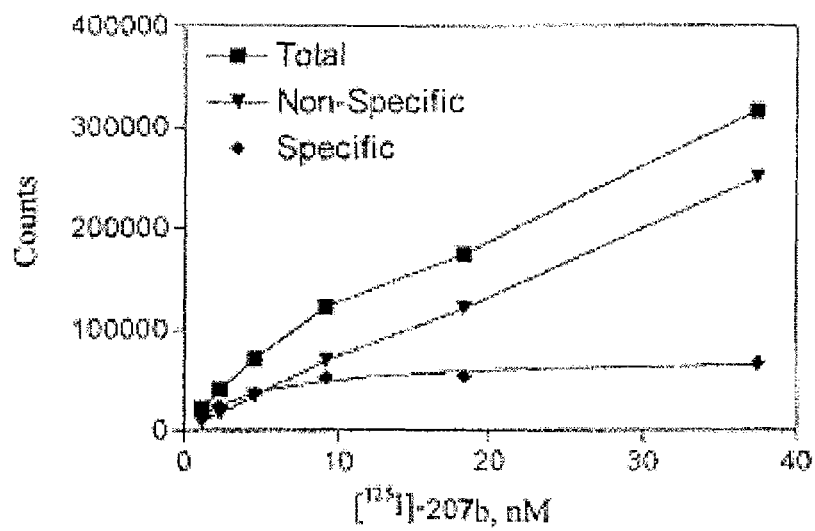
FIG. 10A depicts the non-specific, specific, and total binding of [$^{125}$I] 207b on mouse $A_3$ adenosine receptor.
Figure 10B:
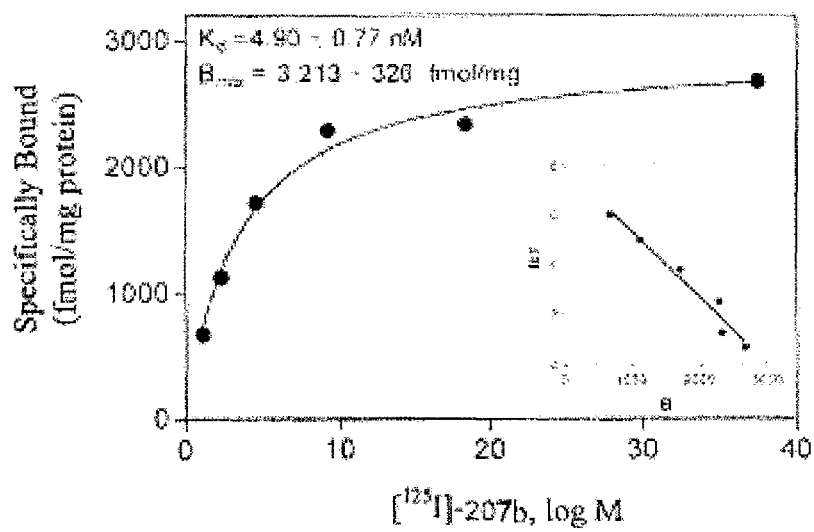
FIG. 10B depicts the extent of specific binding as a function of the concentration of the compound.

FIG. 10A depicts the non-specific, specific, and total binding of [$^{125}$I] 107b on mouse A$_3$ adenosine receptor. FIG. 10B depicts the extent of specific binding as a function of the concentration of the compound. The compound was an agonist of the mouse A$_3$ adenosine receptor.

EXAMPLE 6

This example illustrates a method of preparing a radiolabeled ligand, that is $^{76}$Br-labeled compound 109b in accordance with an embodiment of the invention. Bromine-76 was prepared from an arsenic metal target using the $^{75}$As ($^3$He, 2n) yielding $^{76}$Br nuclear reaction. The $^{76}$Br was processed after allowing for the decay of the simultaneously produced Br-75 ($t_{1/2}$=1.6 h).

An aliquot of the aqueous solution of Br-76 (about 10-20 μl, 18.5-37.0 MBq) is added to a 1-mL reaction vial and the solvent evaporated with argon flow. Trimethylstannyl intermediate 123 in acetonitrile is added to the vial containing the Br-76 radioactivity and followed by adding 37% peracetic acid in acetonitrile. The vial is sealed and placed on an 80° C. heating block and heated for 30 min. At the end of the reaction, the reaction mixture is loaded onto a Phenomenex Luna C18 (2) column (250×4.6 mm) and eluted with 100 mM ammonium acetate/acetonitrile (60/40) at a flow rate of 1.2 mL/min. The radioactivity peak containing the desired product ($t_R$=10 min) is collected and analyzed on a separate HPLC system for determination of purity and specific activity.

Figure 11:
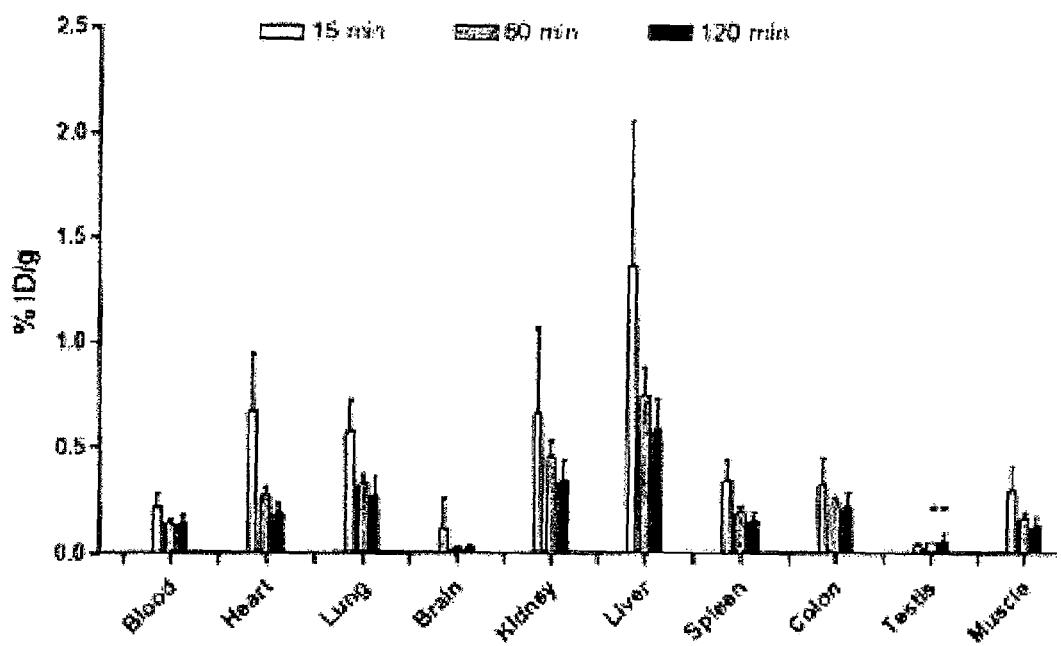
FIG. 11 depicts the biodistribution of Br-76 labeled compound 209b at 15, 60, and 120 min post injection in rats. The Y-axis represents % Initial Dose per gram and X-axis shows various organs.

In vivo biodistribution of compound Br-76 labeled compound 109b was carried out in rats. All studies in live animals were conducted under protocol approved by the NIH Animal Care and Use Committee. The biodistribution was evaluated after intravenous administration to adult Sprague-Dawley rats. The animals were sacrificed at 15, 30, 60, and 120 mM and various tissues were harvested for gamma counting. The data are reported in units of percentage of injected dose per gram in FIG. 11. The compound exhibited antagonistic properties to the A$_3$ adenosine receptor albeit at a low magnitude of uptake. The low uptake may be due to the lower age of the animals. The uptake in the A$_3$AR-containing testes continued to increase with time after injection (0.09% ID/g at 15 min to 0.18% ID/g at 2 h). Blood continued to provide an input function over 2 h. In spite of a potential testes-blood barrier, uptake of the antagonist increased with time, which indicates that the compound may be a viable molecular imaging probe for pathological conditions with elevated A$_3$AR.

EXAMPLE 7

This Example illustrates the ability of the compounds in accordance with an embodiment of the invention to bind to adenosine receptors. The binding affinity values are set forth in Table 3.

Receptor Binding and Functional Assays

[$^3$H]R—N$^6$-Phenylisopropyladenosine (52, [$^3$H]R-PIA, 63 Ci/mmol), [$^{125}$I]N$^6$-(4-Amino-3-iodobenzyl)adenosine-5'-N-methyluronamide (53, [$^{125}$I]I-AB-MECA, 2200 Ci/mmol), and [$^3$H](2-[p-(2-carboxyethyl)phenyl-ethylamino]-5'-N-ethylcarboxamido-adenosine) (54, [$^3$H] CGS21680, 40.5 Ci/mmol) were purchased from PerkinElmer Life and Analytical Science (Boston, Mass.). Test compounds were prepared as 5 mM stock solutions in DMSO and stored frozen.

Cell Culture and Membrane Preparation

CHO cells stably expressing the recombinant hA$_1$, hA$_3$, and rA$_3$Rs, and HEK-293 cells stably expressing the hA$_{2A}$AR were cultured in Dulbecco's modified Eagle medium (DMEM) and F12 (1:1) supplemented with 10% fetal bovine serum, 100 units/mL penicillin, 100 μg/mL streptomycin, and 2 μmol/mL glutamine. In addition, 800 μg/mL geneticin was added to the A$_{2A}$ media, while 500 μg/mL hygromycin was added to the A$_1$ and A$_3$ media. After harvesting, cells were homogenized and suspended in PBS. Cells were then centrifuged at 240 g for 5 min, and the pellet was resuspended in 50 mM Tris-HCl buffer (pH 7.5) containing 10 mM MgCl$_2$. The suspension was homogenized and was then ultra-centrifuged at 14,330 g for 30 min at 4° C. The resultant pellets were resuspended in Tris buffer, incubated with adenosine deaminase (3 units/mL) for 30 min at 37° C. The suspension was homogenized with an electric homogenizer for 10 sec, pipetted into 1 mL vials and then stored at -80° C. until the binding experiments. The protein concentration was measured using the BCA Protein Assay Kit from Pierce Biotechnology, Inc. (Rockford, Ill.).

Binding Assays:

Into each tube in the binding assay was added 50 μL of increasing concentrations of the test ligand in Tris-HCl buffer (50 mM, pH 7.5) containing 10 mM MgCl$_2$, 50 μL of the appropriate agonist radioligand, and finally 100 μL of membrane suspension. For the A$_1$AR (22 μg of protein/tube) the radioligand used was [$^3$H]51 (final concentration of 3.5 nM) or [$^3$H]52 (final concentration of 1.0 nM). For the A$_{2A}$AR (20 μg/tube) the radioligand used was [$^3$H]53 (10 nM). For the A$_3$AR (21 μg/tube) the radioligand used was [$^{125}$I]54 (0.34 nM). Nonspecific binding was determined using a final concentration of 10 μM 51 diluted with the buffer. The mixtures were incubated at 25° C. for 60 min in a shaking water bath. Binding reactions were terminated by filtration through Brandel GF/B filters under a reduced pressure using a M-24 cell harvester (Brandel, Gaithersburg, Md.). Filters were washed three times with 3 mL of 50 mM ice-cold Tris-HCl buffer (pH 7.5). Filters for A$_1$ and A$_{2A}$AR binding were placed in scintillation vials containing 5 mL of HYDROFLUOR™ scintillation buffer and counted using a Perkin Elmer Liquid Scintillation Analyzer (TRI-CARB™ 2810TR). Filters for A$_3$AR binding were counted using a Packard COBRA™ II γ-counter. The K$_i$ values were determined using GraphPad Prism for all assays.

Similar competition binding assays were conducted using HEK 293 cell membranes expressing mARs using [$^{125}$I]I-AB-MECA to label A$_1$ or A$_3$ARs and [$^3$H]CGS 21680 to label A$_{2A}$ARs.$^{56}$ IC$_{50}$ values were converted to K$_i$ values as described.$^{57}$ [$^{125}$I]N$^6$-(4-amino-3-iodo-benzyl)adenosine-5'-N-methyluronamide ([$^{125}$I]I-AB-MECA; 2000 Ci/mmol), [$^3$H]R-PIA (R—N$^6$-[phenylisopropyl]adenosine, 34 Ci/mmol), [$^3$H]CGS21680 (2-[p-(2-carboxyethyl)phenyl-ethylamino]-5'-N-ethylcarboxamido-adenosine, 47 Ci/mmol) and [$^3$H]cAMP (40 Ci/mmol) were from Amersham Pharmacia Biotech (Buckinghamshire, UK).

cAMP Accumulation Assay:

Intracellular cAMP levels were measured with a competitive protein binding method. CHO cells that expressed the recombinant hA$_3$AR were harvested by trypsinization. After centrifugation and resuspended in medium, cells were planted in 24-well plates in 1.0 mL medium. After 24 h, the medium was removed and cells were washed three times with 1 mL DMEM, containing 50 mM HEPES, pH 7.4. Cells were then treated with the agonist 51 or test compound in the presence of rolipram (10 µM) and adenosine deaminase (3 units/mL). After 45 min forskolin (10 µM) was added to the medium, and incubation was continued for an additional 15 min. The reaction was terminated by removing the supernatant, and cells were lysed upon the addition of 200 µL of 0.1 M ice-cold HCl. The cell lysate was resuspended and stored at −20° C. For determination of cAMP production, 100 µL of the HCl solution was used in the Sigma Direct cAMP Enzyme immunoassay following the instructions provided with the kit. The results were interpreted using a Bio-Tek Instruments ELx808 Ultra Microplate reader at 405 nm.

TABLE 3

Binding affinity of a series of (N)-methanocarba adenosine derivatives at three subtypes of hARs and the functional efficacy at the hA$_3$AR.

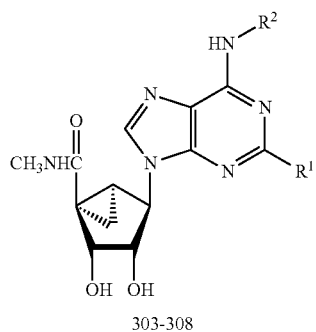

303-308

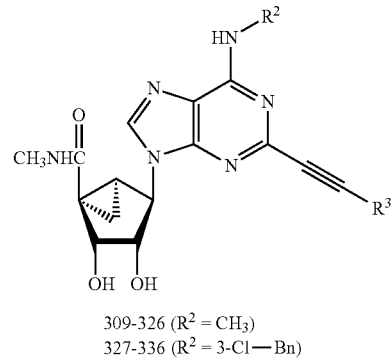

309-326 (R$^2$ = CH$_3$)
327-336 (R$^2$ = 3-Cl—Bn)

| Cmpd/ MRS | Structure R$^1$ or R$^3$ | R$^2$ | Affinity (K$_i$, nM) or % inhibition$^a$ hA$_1$ | hA$_{2A}$ | hA$_3$ | % Efficacy hA$_3$ |
|---|---|---|---|---|---|---|
| 303$^c$ | Cl | 3-Cl—Bn | 260 ± 60 | 2300 ± 100 | 0.29 ± 0.04 | 103 ± 7 |
| 304$^{c,d}$ | Cl | 3-I—Bn | 136 ± 22 | 784 ± 97 | 1.5 ± 0.2 | 100 |
| 305$^c$ | H | 3-I—Bn | 700 ± 270 | 6200 ± 100 | 2.4 ± 0.5 | 100 |
| 306$^d$ | C≡CH | 3-Cl—Bn | 174 ± 23 | (48%) | 1.30 ± 0.38 | ND |
| 307$^d$ | C≡C(CH$_2$)$_2$CH$_3$ | 3-Cl—Bn | 1040 ± 83 | (80%) | 0.82 ± 0.20 | ND |
| 308$^{c,d}$ | Cl | CH$_3$ | 2100 ± 1700 | (6%) | 2.2 ± 0.6 | |
| 309 5644 | phenyl | CH$_3$ | (18% ± 8%) | (14% ± 7%) | 0.85 ± 0.22 | |
| 310 5661 | 2-pyridyl | CH$_3$ | (13% ± 8%) | (13% ± 4%) | 1.01 ± 0.36 | |
| 311 5673 | 2-fluorophenyl | CH$_3$ | (20% ± 7%) | (17% ± 2%) | 0.97 ± 0.38 | |
| 312 5671 | 3-fluorophenyl | CH$_3$ | (14% ± 2%) | (10% ± 5%) | 0.97 ± 0.24 | |
| 313 5657 | 4-fluorophenyl | CH$_3$ | (27% ± 17%) | (19% ± 3%) | 0.53 ± 0.09 | |
| 314 5663 | 2-chlorophenyl | CH$_3$ | (22% ± 6%) | (30% ± 5%) | 0.58 ± 0.04 | |
| 315 5674 | 3-chlorophenyl | CH$_3$ | (11% ± 4%) | 1270 ± 300 | 1.60 ± 0.60 | |
| 316$^e$ 5675 | 4-chlorophenyl | CH$_3$ | (13% ± 1%) | (30% ± 1%) | 1.22 ± 0.31 | |
| 317 5672 | 4-bromophenyl | CH$_3$ | (11% ± 11%) | (26% ± 1%) | 0.91 ± 0.06 | |
| 318 5668 | 3-aminophenyl | CH$_3$ | (16% ± 2%) | (19% ± 14%) | 1.07 ± 0.14 | |
| 319 5676 | 3,-difluorophenyl | CH$_3$ | (6% ± 6%) | (6% ± 6%) | 1.65 ± 0.08 | |
| 320 5677 | 3,5-difluorophenyl | CH$_3$ | (6% ± 2%) | (47% ± 4%) | 1.66 ± 0.36 | |
| 321 5670 | 4-ethylphenyl | CH$_3$ | (14% ± 4%) | (38% ± 5%) | 3.78 ± 1.16 | |
| 322 5662 | 4-t-butylphenyl | CH$_3$ | (27% ± 7%) | (7% ± 5%) | 10.1 ± 1.9 | |
| 323 5696 | 4-acetylphenyl | CH$_3$ | (8% ± 2%) | (62% ± 3%) | 2.57 ± 0.78 | |
| 324 5667 | 4-phenylphenyl | CH$_3$ | (20% ± 11%) | (29% ± 8%) | 3.10 ± 1.26 | |
| 325 5665 | 1-naphthyl | CH$_3$ | (24% ± 2%) | (34% ± 8%) | 1.67 ± 0.18 | |

TABLE 3-continued

Binding affinity of a series of (N)-methanocarba adenosine derivatives at three subtypes of hARs and the functional efficacy at the hA₃AR.

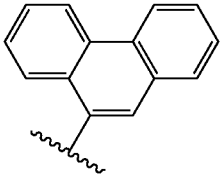 [SMILES: *c1cc2ccccc2c2ccccc12]

303-308

309-326 ($R^2 = CH_3$)
327-336 ($R^2 = 3$-Cl—Bn)

| Cmpd/ MRS | Structure | | Affinity ($K_i$, nM) or % inhibition[a] | | | % Efficacy |
|---|---|---|---|---|---|---|
| | $R^1$ or $R^3$ | $R^2$ | $hA_1$ | $hA_{2A}$ | $hA_3$ | $hA_3$ |
| 326 5666 | 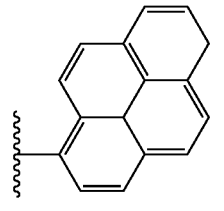 [SMILES: *C1=C2C=CC3=C4C(=CC=C(C=C1)C24)CC=C3] | $CH_3$ | (15% ± 9%) | (52% ± 1%) | 3.48 ± 1.36 | |
| 327 5655 | phenyl | 3-Cl—Bn | (18% ± 2%) | (27% ± 3%) | 1.34 ± 0.30 | |
| 328 5678 | 4-fluorophenyl | 3-Cl—Bn | (19% ± 11%) | (42% ± 2%) | 2.16 ± 0.34 | |
| 329 5697 | 2-chlorophenyl | 3-Cl—Bn | (20% ± 4%) | (52% ± 12%) | 1.92 ± 0.57 | |
| 330 5703 | 3-chlorophenyl | 3-Cl—Bn | (0% ± 0%) | 1620 | 1.95 | |
| 331 5698 | 3,4-difluorophenyl | 3-Cl—Bn | (3% ± 1%) | (41% ± 10%) | 2.13 | |
| 332a 5699 | 4-aminophenyl | 3-Cl—Bn | (2%) | (44% ± 4%) | 2.27 ± 0.70 | |
| 332b 5723 | 3-iodo-4-aminophenyl | 3-Cl—Bn | | | | |
| 333 5700 | 3-carboxylphenyl | 3-Cl—Bn | (1% ± 1%) | (38% ± 5%) | 6.75 ± 2.78 | |
| 334 5701 | 4-sulfonyloxyphenyl | 3-Cl—Bn | | | | |
| 335 5679 | 4-phenylphenyl | 3-Cl—Bn | (0% ± 0%) | (0% ± 0%) | 3.06 ± 1.35 | |
| 336 5704 | 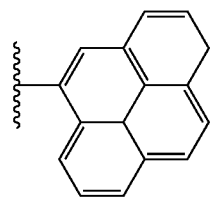 [SMILES: *C1=CC2=C3C(=CC=C4C=CC=C1C43)CC=C2] | 3-Cl—Bn | (6%) | (66%) | 68.3 ± 12.5 | |
| 337a 5702 | 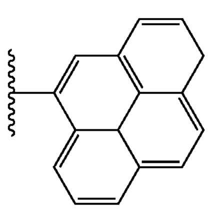 | 3-Cl—Bn | | | | |

TABLE 3-continued

Binding affinity of a series of (N)-methanocarba adenosine derivatives at three subtypes of hARs and the functional efficacy at the hA₃AR.

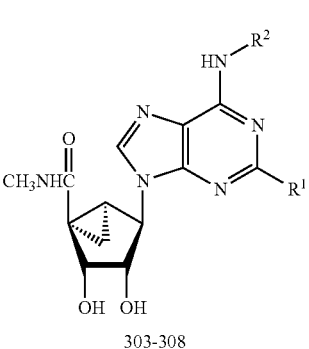

303-308

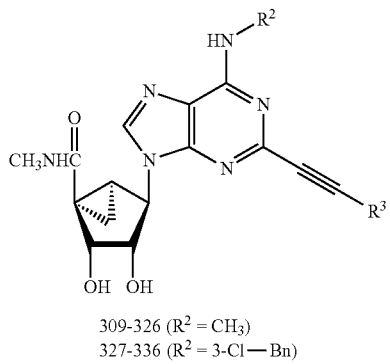

309-326 ($R^2 = CH_3$)
327-336 ($R^2 = 3$-Cl—Bn)

| Cmpd/ | Structure | | Affinity ($K_i$, nM) or % inhibition[a] | | | % Efficacy |
|---|---|---|---|---|---|---|
| MRS | $R^1$ or $R^3$ | $R^2$ | $hA_1$ | $hA_{2A}$ | $hA_3$ | $hA_3$ |
| 337b | [pyrenyl group] | 3-Cl—Bn | | | | |

[a]All experiments were done on CHO or HEK293 ($A_{2A}$ only) cells stably expressing one of three subtypes of the four human ARs. The binding affinity for $A_1$, $A_{2A}$ and $A_3$ARs was expressed as $K_i$ values (n = 3-5) and was determined by using agonist radioligands ([³H]52; [³H]54; or [¹²⁵I]53; respectively), unless noted. A percent in parentheses refers to inhibition of radioligand binding at 10 μM.
[b]Unless noted, the efficacy at the human $A_3$AR was determined by inhibition of forskolin-stimulated cAMP production in AR-transfected CHO cells. At a concentration of 10 μM, in comparison to the maximal effect of 51 (= 100%) at 10 μM. Data are expressed as mean ± standard error (n = 3).
[c]Values from Lee, K. et al., *Bioorg. Med. Chem. Lett.* 2001, 11, 1333-1337, Tchilibon, S. et al., *J. Med. Chem.* 2005, 48, 1745-1758.
[d]Values from Melman, A. et al., *Bioorg. Med. Chem. Lett.* 2008, 18, 2813-2819.
ND, not determined.

EXAMPLE 8

This Example illustrates the ability of the compounds in accordance with an embodiment of the invention to bind to three subtypes of mARs receptors. The binding affinity values are set forth in Table 4.

TABLE 4

Binding affinity of a series of (N)-methanocarba adenosine derivatives at three subtypes of mARs.

| | Affinity (Ki, nM) or % inhibition[a] | | | % Efficacy[a] |
|---|---|---|---|---|
| Cmpd. | $mA_1$ | $mA_{2A}$ | $mA_3$ | $mA_3$ |
| 303[b] | 15.3 ± 5.8 | 10,400 ± 1,700 | 1.49 ± 0.46 | |
| 304[b] | 7.32 ± 1.5 | 5,350 ± 860 | 0.80 ± 0.14 | |
| 306[b] | 45.6 ± 7.9 | (41%)¹ | 0.85 ± 0.08 | |
| 307[b] | 1390 ± 430 | (42%)¹ | 6.06 ± 1.21 | |
| 308[b] | 55.3 ± 6.0 | 20,400 ± 3,200 | 49.0 ± 3.9 | |
| 313 | (25%) | | | 66 |
| 314 | (45%) | | | 55 |
| 327 | (41%) | | | 16 |
| 328 | (39%) | | | 7.5 |
| 329 | (36%) | | | 7.5 |
| 331 | (14%) | | | 14 |
| 332a | (93%) | | | 17 |
| 335 | (28%) | | | 22 |

[a]Competition radioligand binding assays using [¹²⁵I]N6-(4-amino-3-iodobenzyl)adenosine-5′-N-methyl-uronamide ($A_1$ and $A_3$ARs) and [³H]2-[p-(2-carboxyethyl)phenyl-ethylamino]-5′-N-ethylcarboxamidoadenosine (A2AAR) were conducted with membranes prepared from HEK293 cells expressing recombinant $mA_1$, $A_{2A}$, or $A_3$ARs.
[b]Values from Melman, A. et al., *Bioorg. Med. Chem. Lett.* 2008, 18, 2813-2819.

EXAMPLE 9

This example demonstrates a method of preparing compounds in accordance with an embodiment of the invention.

(1S,2R,3S,4R,5S)-2,3-Dihydroxy-N-methyl-4-(6-(methylamino)-2-(phenylethynyl)-9H-purin-9-yl)bicyclo[3.1.0]hexane-1-carboxamide (309)

A solution of compound 345a (29 mg, 0.06 mmol) in methanol (2 mL) and 10% trifluoromethane sulfonic acid (2 mL) was heated at 70° C. for 5 h. Solvent was evaporated under vacuum, and the residue was purified on flash silica gel column chromatography ($CH_2Cl_2$:MeOH=25:1) to give compound 309 (21 mg, 81%) as a syrup. ¹H NMR ($CD_3OD$, 400 MHz) δ 8.12 (s, 1H), 7.67-7.65 (m, 2H), 7.47-7.43 (m, 2H), 5.06 (d, J=5.2 Hz, 1H), 4.08 (d, J=6.4 Hz, 1H), 3.15 (br s, 3H), 2.84 (s, 3H), 2.13-2.10 (m, 1H), 1.88 (t, J=5.2 Hz, 1H), 1.41-1.39 (m, 1H). HRMS calculated for $C_{22}H_{23}N_6O_3$ $(M+H)^+$: 419.1832. found 419.1818.

(1S,2R,3S,4R,5S)-2,3-Dihydroxy-N-methyl-4-(6-(methylamino)-2-(pyridin-2-ylethynyl)-9H-purin-9-yl)bicyclo[3.1.0]hexane-1-carboxamide (310)

Compound 310 (80%) was prepared from compound 346 following the same method as used for compound 309. ¹H NMR ($CD_3OD$, 400 MHz) δ 8.65 (s, 1H), 8.01 (s, 1H), 7.91-7.97 (m, 1H), 7.87 (d, J=8.8 Hz, 1H), 7.53-7.48 (m, 1H), 5.15 (d, J=5.6 Hz, 1H), 4.09 (d, J=8.4 Hz, 1H), 3.14 (br s, 3H), 2.83 (s, 3H), 2.13-2.06 (m, 1H), 1.85 (t, J=5.2 Hz, 1H), 1.42-1.40 (m, 1H). HRMS calculated for $C_2H_{22}N_7O_3$ $(M+H)^+$: 420.1784. found 420.1797.

(1S,2R,3S,4R,5S)-4-(2-((2-Fluorophenyl)ethynyl)-6-(methylamino)-9H-purin-9-yl)-2,3-dihydroxy-N-methylbicyclo[3.1.0]hexane-1-carboxamide (311)

Compound 311 (82%) was prepared from compound 345b following the same method as used for compound 309. $^1$H NMR (CD$_3$OD, 400 MHz) δ 8.11 (s, 1H), 7.49-7.39 (m, 3H), 7.25-7.20 (m, 1H), 5.06 (d, J=5.2 Hz, 1H), 4.9 (s, 1H), 4.02 (d, J=6.8 Hz, 1H), 3.15 (br s, 1H), 2.84 (s, 3H), 2.13-2.10 (m, 1H), 1.88 (t, J=4.8 Hz, 1H), 1.41-1.38 (m, 1H). HRMS calculated for $C_{22}H_{22}FN_6O_3$ $(M+H)^+$: 437.1737. found 437.1753.

(1S,2R,3S,4R,5S)-4-(2-((3-Fluorophenyl)ethynyl)-6-(methylamino)-9H-purin-9-yl)-2,3-dihydroxy-N-methylbicyclo[3.1.0]hexane-1-carboxamide (312)

Compound 312 (78%) was prepared from compound 345c following the same method as used for compound 309. $^1$H NMR (CD$_3$OD, 400 MHz) δ 8.11 (s, 1H), 7.67 (t, J=6.0 Hz, 1H), 7.52-7.47 (m, 1H), 7.28-7.22 (m, 2H), 5.07 (d, J=6.8 Hz, 1H), 4.03 (d, J=6.8 Hz, 1H), 3.13 (br s, 1H), 2.84 (s, 3H), 2.13-2.10 (m, 1H), 1.88 (t, J=4.8 Hz, 1H), 1.41-1.40 (m, 1H). HRMS calculated for $C_{22}H_{22}FN_6O_3$ $(M+H)^+$: 437.1737. found 437.1718.

(1S,2R,3S,4R,5S)-4-(2-((4-Fluorophenyl)ethynyl)-6-(methylamino)-9H-purin-9-yl)-2,3-dihydroxy-N-methylbicyclo[3.1.0]hexane-1-carboxamide (313.)

Compound 313 (81%) was prepared from compound 345d following the same method as used for compound 309. $^1$H NMR (CD$_3$OD, 400 MHz) δ 8.11 (s, 1H), 7.75-7.68 (m, 2H), 7.23-7.18 (m, 2H), 5.05 (d, J=6.0 Hz, 1H), 4.02 (d, J=6.4 Hz, 1H), 3.14 (br s, 3H), 2.84 (s, 3H), 2.13-2.10 (m, 1H), 1.89 (t, J=4.8 Hz, 1H), 1.41-1.39 (m, 1H). HRMS calculated for $C_{22}H_{22}FN_6O_3$ $(M H)^+$: 437.1737. found 437.1722.

(1S,2R,3S,4R,5S)-4-(2-((2-Chlorophenyl)ethynyl)-6-(methylamino)-9H-purin-9-yl)-2,3-dihydroxy-N-methylbicyclo[3.1.0]hexane-1-carboxamide (314)

Compound 314 (85%) was prepared from compound 345e following the same method as used for compound 309. $^1$H NMR (CD$_3$OD, 400 MHz) δ 8.11 (s, 1H), 7.72 (d, J=7.2 Hz, 1H), 7.54 (d, J=7.2 Hz, 1H), 7.46-7.36 (m, 2H), 5.10 (d, J=6.4 Hz, 1H), 4.04 (d, J=6.8 Hz, 1H), 3.15 (br s, 3H), 2.83 (s, 3H), 2.12-2.08 (m, 1H), 1.86 (t, J=4.8 Hz, 1H), 1.41-1.39 (m, 1H). HRMS calculated for $C_{22}H_{22}ClN_6O_3$ $(M+H)^+$: 453.1442. found 453.1449.

(1S,2R,3S,4R,5S)-4-(2-((3-Chlorophenyl)ethynyl)-6-(methylamino)-9H-purin-9-yl)-2,3-dihydroxy-N-methylbicyclo[3.1.0]hexane-1-carboxamide (315)

Compound 315 (82%) was prepared from compound 345f following the same method as used for compound 309. $^1$H NMR (CD$_3$OD, 400 MHz) δ 8.11 (s, 1H), 7.67 (s, 1H), 7.59 (d, J=7.2 Hz, 1H), 7.49-7.42 (m, 2H), 5.06 (d, J=6.4 Hz, 1H), 4.02 (d, J=6.8 Hz, 1H), 3.14 (br s, 3H), 2.84 (s, 3H), 2.13-2.10 (m, 1H), 1.88 (t, J=4.8 Hz, 1H), 1.41-1.39 (m, 1H). HRMS calculated for $C_{22}H_{22}ClN_6O_3$ $(M+H)^+$: 453.1442. found 453.1442.

(1S,2R,3S,4R,5S)-4-(2-((4-Chlorophenyl)ethynyl)-6-(methylamino)-9H-purin-9-yl)-2,3-dihydroxy-N-methylbicyclo[3.1.0]hexane-1-carboxamide (316)

Compound 316 (84%) was prepared from compound 345g following the same method as used for compound 309. $^1$H NMR (CD$_3$OD, 400 MHz) δ 8.10 (s, 1H), 7.64 (d, J=8.4 Hz, 2H), 7.46 (d, J=8.4 Hz, 2H), 5.06 (d, J=5.6 Hz, 1H), 4.88 (s, 1H), 4.02 (d, J=6.4 Hz, 1H), 3.15 (br s, 3H), 2.84 (s, 3H), 2.13-2.09 (m, 1H), 1.88 (t, J=4.8 Hz, 1H), 1.41-1.38 (m, 1H). HRMS calculated for $C_{22}H_{22}ClN_6O_3$ $(M+H)^+$: 453.1460. found 453.1454.

(1S,2R,3S,4R,5S)-4-(2-((4-Bromophenyl)ethynyl)-6-(methylamino)-9H-purin-9-yl)-2,3-dihydroxy-N-methylbicyclo[3.1.0]hexane-1-carboxamide (317)

Compound 317 (76%) was prepared from compound 345h following the same method as used for compound 309. $^1$H NMR (CD$_3$OD, 400 MHz) δ 8.10 (s, 1H), 7.62 (d, J=8.8 Hz, 2H), 7.56 (d, J=8.4 Hz, 2H), 5.05 (d, J=6.8 Hz, 1H), 4.88 (s, 1H), 4.02 (d, J=6.4 Hz, 1H), 3.14 (br s, 3H), 2.84 (s, 3H), 2.13-2.09 (m, 1H), 1.88 (t, J=5.2 Hz, 1H), 1.41-1.38 (m, 1H). HRMS calculated for $C_{22}H_{22}BrN_6O_3$ $(M+H)^+$: 497.0937. found 497.0948.

(1S,2R,3S,4R,5S)-4-(2-((3-Aminophenyl)ethynyl)-6-(methylamino)-9H-purin-9-yl)-2,3-dihydroxy-N-methylbicyclo[3.1.0]hexane-1-carboxamide (318)

Compound 318 (67%) was prepared from compound 345i following the same method as used for compound 309. $^1$H NMR (CD$_3$OD, 400 MHz) δ 8.09 (s, 1H), 7.14 (t, J=8.0 Hz, 1H), 6.98-6.94 (m, 2H), 6.80-6.78 (m, 1H), 5.06 (d, J=5.6 Hz, 1H), 4.02 (d, J=6.4 Hz, 1H), 3.15 (br s, 3H), 2.85 (s, 3H), 2.12-2.09 (m, 1H), 1.87 (t, J=4.8 Hz, 1H), 1.41-1.39 (m, 1H). HRMS calculated for $C_{22}H_{22}N_7O_3$ $(M+H)^+$: 432.1784. found 432.1799.

(1S,2R,3S,4R,5S)-4-(2-((3,4-Difluorophenyl)ethynyl)-6-(methylamino)-9H-purin-9-yl)-2,3-dihydroxy-N-methylbicyclo[3.1.0]hexane-1-carboxamide (319)

Compound 319 (83%) was prepared from compound 345j following the same method as used for compound 309. $^1$H NMR (CD$_3$OD, 400 MHz) δ 8.12 (s, 1H), 7.58-7.50 (m, 1H), 7.50-7.48 (m, 1H), 7.40-7.34 (m, 1H), 5.06 (d, J=6.4 Hz, 1H), 4.02 (d, J=6.4 Hz, 1H), 3.14 (br s, 3H), 2.84 (s, 3H), 2.13-2.09 (m, 1H), 1.88 (t, J=4.8 Hz, 1H), 1.41-1.40 (m, 1H). HRMS calculated for $C_{22}H_{21}F_2N_6O_3$ $(M+H)^+$: 455.1643. found 455.1639.

(1S,2R,3S,4R,5S)-4-(2-((3,5-Difluorophenyl)ethynyl)-6-(methylamino)-9H-purin-9-yl)-2,3-dihydroxy-N-methylbicyclo[3.1.0]hexane-1-carboxamide (320)

Compound 320 (84%) was prepared from compound 345k following the same method as used for compound 309. $^1$H NMR (CD$_3$OD, 400 MHz) δ 8.12 (s, 1H), 7.31-7.26 (s, 2H), 7.14-7.09 (m, 1H), 7.49-7.42 (m, 2H), 5.06 (d, J=5.2 Hz, 1H), 4.89 (s, 1H), 4.03 (d, J=6.4 Hz, 1H), 3.14 (br s, 3H), 2.84 (s, 3H), 2.12-2.09 (m, 1H), 1.88 (t, J=4.8 Hz, 1H), 1.41-1.39 (m, 1H). HRMS calculated for $C_{22}H_{21}F_2N_6O_3$ $(M+H)^+$: 455.1643. found 455.1630.

(1S,2R,3S,4R,5S)-4-(2-((4-Ethylphenyl)ethynyl)-6-(methylamino)-9H-purin-9-yl)-2,3-dihydroxy-N-methylbicyclo[3.1.0]hexane-1-carboxamide (321)

Compound 321 (79%) was prepared from compound 345l following the same method as used for compound 309. $^1$H NMR (CD$_3$OD, 400 MHz) δ 8.09 (s, 1H), 7.57 (d, J=8.0 Hz, 2H), 7.29 (d, J=8.0 Hz, 2H), 5.06 (d, J=5.2 Hz, 1H), 4.91 (s, 1H), 4.02 (d, J=6.4 Hz, 1H), 3.15 (br s, 3H), 2.84 (s, 3H), 2.74-2.68 (m, 2H), 2.13-2.09 (m, 1H), 1.88 (t, J=4.8 Hz, 1H), 1.41-1.38 (m, 1H), 1.30 (t, J=7.6 Hz, 3H). HRMS calculated for C$_{24}$H$_{27}$N$_6$O$_3$ (M+H)$^+$: 447.2145. found 447.2130.

(1S,2R,3S,4R,5S)-4-(2-((4-tert-Butylphenyl)ethynyl)-6-(methylamino)-9H-purin-9-yl)-2,3-dihydroxy-N-methylbicyclo[3.1.0]hexane-1-carboxamide (322)

Compound 322 (83%) was prepared from compound 345m following the same method as used for compound 309. $^1$H NMR (CD$_3$OD, 400 MHz) δ 8.10 (s, 1H), 7.59 (d, J=8.4 Hz, 2H), 7.50 (d, J=8.4 Hz, 2H), 5.06 (d, J=6.4 Hz, 1H), 4.02 (d, J=6.4 Hz, 1H), 3.15 (br s, 3H), 2.85 (s, 3H), 2.13-2.10 (m, 1H), 188 (t, J=4.8 Hz, 1H), 1.41-1.39 (m, 10H). HRMS calculated for C$_{26}$H$_{31}$N$_6$O$_3$ (M+H)$^+$: 475.2458. found 475.2450.

(1S,2R,3S,4R,5S)-4-(2-((4-Acetylphenyl)ethynyl)-6-(methylamino)-9H-purin-9-yl)-2,3-dihydroxy-N-methylbicyclo[3.1.0]hexane-1-carboxamide (323)

Compound 323 (80%) was prepared from compound 345n following the same method as used for compound 309. $^1$H NMR (CD$_3$OD, 400 MHz) δ 8.11 (s, 1H), 8.06 (d, J=8.4 Hz, 2H), 7.77 (d, J=8.0 Hz, 2H), 5.06 (d, J=6.4 Hz, 1H), 4.03 (d, J=6.4 Hz, 1H), 3.15 (br s, 3H), 2.84 (s, 3H), 2.64 (s, 3H), 2.14-2.10 (m, 1H), 1.88 (t, J=4.8 Hz, 1H), 1.41-1.39 (m, 1H). HRMS calculated for C$_{24}$H$_{25}$N$_6$O$_4$ (M+H)$^+$: 461.1937. found 461.1937.

(1S,2R,3S,4R,5S)-4-(2-(Biphenyl-4-ylethynyl)-6-(methylamino)-9H-purin-9-yl)-2,3-dihydroxy-N-methylbicyclo[3.1.0]hexane-1-carboxamide (324)

Compound 324 (74%) was prepared from compound 345o following the same method as used for compound 309. $^1$H NMR (CD$_3$OD, 400 MHz) δ 8.11 (s, 1H), 7.75-7.67 (m, 6H), 7.47 (t, J=7.6 Hz, 2H), 7.38 (t, J=7.2 Hz, 1H), 5.06 (d, J=6.0 Hz, 1H), 4.89 (s, 1H), 4.03 (d, J=6.4 Hz, 1H), 3.16 (br s, 3H), 2.84 (s, 3H), 2.13-2.10 (m, 1H), 189 (t, J=4.8 Hz, 1H), 1.42-1.39 (m, 1H). HRMS calculated for C$_{28}$H$_{27}$N$_6$O$_3$ (M+H)$^+$: 495.2145. found 495.2141.

(1S,2R,3S,4R,5S)-2,3-Dihydroxy-N-methyl-4-(6-(methylamino)-2-(naphthalen-1-ylethynyl)-9H-purin-9-yl)bicyclo[3.1.0]hexane-1-carboxamide (325)

Compound 325 (73%) was prepared from compound 345p following the same method as used for compound 309. $^1$H NMR (CD$_3$OD, 400 MHz) δ 8.56 (d, J=7.6 Hz, 1H), 8.11 (s, 1H), 8.00-7.90 (m, 3H), 7.68 (t, J=5.6 Hz, 1H), 7.62-7.53 (m, 2H), 5.10 (d, J=5.2 Hz, 1H), 4.93 (s, 1H), 4.06 (d, J=6.4 Hz, 1H), 3.19 (br s, 3H), 2.79 (s, 3H), 2.15-2.12 (m, 1H), 189 (t, J=4.8 Hz, 1H), 1.41-1.38 (m, 1H). HRMS calculated for C$_{26}$H$_{25}$N$_6$O$_3$ (M+H)$^+$: 469.1988. found 469.2005.

(1S,2R,3S,4R,5S)-2,3-Dihydroxy-N-methyl-4-(6-(methylamino)-2-(phenanthren-9-ylethynyl)-9H-purin-9-yl)bicyclo[3.1.0]hexane-1-carboxamide (326)

Compound 326 (65%) was prepared from compound 345q following the same method as used for compound 309. $^1$H NMR (CD$_3$OD, 400 MHz) δ 8.84-8.77 (m, 2H), 8.66-8.63 (m, 1H), 8.26 (s, 1H), 8.12 (s, 1H), 7.97 (d, J=7.6 Hz, 1H), 7.80-7.73 (m, 3H), 7.66 (t, J=7.2 Hz, 1H), 5.10 (d, J=6.0 Hz, 1H), 4.92 (s, 1H), 4.07 (d, J=6.4 Hz, 1H), 3.20 (br s, 3H), 2.81 (s, 3H), 2.15-2.12 (m, 1H), 1.90 (t, J=4.8 Hz, 1H), 1.42-1.38 (m, 1H). HRMS calculated for C$_{30}$H$_{27}$N$_6$O$_3$ (M+H)$^+$: 519.2145. found 519.2137.

(1S,2R,3S,4R,5S)-4-(6-(3-Chlorobenzylamino)-2-(phenylethynyl)-9H-purin-9-yl)-2,3-dihydroxy-N-methylbicyclo[3.1.0]hexane-1-carboxamide (327)

PdCl$_2$(PPh$_3$)$_2$ (6.13 mg, 0.008 mmol), CuI (1.2 mg, 0.004 mmol), phenylacetylene (30 μL, 0.26 mmol) and triethylamine (60 μL, 0.4 mmol) was added to a solution of compound 344 (26 mg, 0.04 mmol) in anhydrous DMF (1 mL), and stirred at room temperature overnight. Solvent was evaporated under vacuum, and the residue was roughly purified on flash silica gel column chromatography. The resulting compound was dissolved in methanol (2 mL) and 10% trifluoromethane sulfonic acid (2 mL) and heated at 70° C. for 5 h. Solvent was evaporated under vacuum, and the residue was purified on flash silica gel column chromatography (CH$_2$Cl$_2$:MeOH=25:1) to give compound 327 (17 mg, 76%) as a syrup. $^1$H NMR (CD$_3$OD, 400 MHz) δ 8.13 (s, 1H), 7.66-7.63 (m, 2H), 7.46-7.42 (m, 4H), 7.37-7.26 (m, 3H), 5.06 (d, J=5.6 Hz, 1H), 4.9 (br s, 2H) 4.04 (d, J=6.4 Hz, 1H), 2.84 (s, 3H), 2.14-2.11 (m, 1H), 1.88 (t, J=4.8 Hz, 1H), 1.41-1.37 (m, 1H). HRMS calculated for C$_{28}$H$_{26}$ClN$_6$O$_3$ (M+H)$^+$: 529.1755. found 529.1740.

(1S,2R,3S,4R,5S)-4-(6-(3-Chlorobenzylamino)-2-((4-fluorophenyl)ethynyl)-9H-purin-9-yl)-2,3-dihydroxy-N-methylbicyclo[3.1.0]hexane-1-carboxamide (328)

Compound 328 (68%) was prepared from compound 344 following the same method as used for compound 327. $^1$H NMR (CD$_3$OD, 400 MHz) δ 8.13 (s, 1H), 7.70-7.63 (m, 2H), 7.59-7.55 (m, 1H), 7.45 (s, 1H), 7.37-7.21 (m, 3H), 7.19-7.16 (m, 1H), 5.06 (d, J=5.6 Hz, 1H), 4.9 (s, 1H), 4.58 (br s, 2H), 4.04 (d, J=7.6 Hz, 1H), 2.84 (s, 3H), 2.17-2.10 (m, 1H), 1.88 (t, J=4.8 Hz, 1H), 1.41-1.38 (m, 1H). HRMS calculated for C$_{28}$H$_{25}$ClFN$_6$O$_3$ (M+H)$^+$: 547.1661. found 547.1652.

(1S,2R,3S,4R,5S)-4-(6-(3-Chlorobenzylamino)-2-((2-chlorophenyl)ethynyl)-9H-purin-9-yl)-2,3-dihydroxy-N-methylbicyclo[3.1.0]hexane-1-carboxamide (29)

Compound 329 (65%) was prepared from compound 344 following the same method as used for compound 327. $^1$H NMR (CD$_3$OD, 400 MHz) δ 8.14 (s, 1H), 7.72-7.70 (m, 1H), 7.53 (d, J=8.0 Hz, 1H), 7.47-7.25 (m, 6H), 5.11 (d, J=6.8 Hz, 1H), 4.90 (s, 1H), 4.05 (d, J=6.8 Hz, 1H), 2.82 (s, 3H), 2.12-2.09 (m, 1H), 1.86 (t, J=4.8 Hz, 1H), 1.40-1.38 (m, 1H). HRMS calculated for C$_{28}$H$_{24}$Cl$_2$N$_6$O$_3$Na (M+Na): 585.1185. found 585.1167.

(1S,2R,3S,4R,5S)-4-(6-(3-Chlorobenzylamino)-2-((3-chlorophenyl)ethynyl)-9H-purin-9-yl)-2,3-dihydroxy-N-methylbicyclo[3.1.0]hexane-1-carboxamide (330)

Compound 330 (66%) was prepared from compound 344 following the same method as used for compound 327. $^1$H NMR (CD$_3$OD, 400 MHz) δ 8.15 (s, 1H), 7.66-7.57 (m, 2H), 7.48-7.26 (m, 6H), 5.07 (d, J=6.4 Hz, 1H), 4.85 (s, 1H), 4.04 (d, J=6.8 Hz, 1H), 2.84 (s, 3H), 2.14-2.10 (m, 1H), 1.88 (t, J=4.8 Hz, 1H), 1.41-1.39 (m, 1H). HRMS calculated for C$_{28}$H$_{25}$Cl$_2$N$_6$O$_3$ (M+H)$^+$: 563.1365. found 563.1359.

(1S,2R,3S,4R,5S)-4-(6-(3-Chlorobenzylamino)-2-((3,4-difluorophenyl)ethynyl)-9H-purin-9-yl)-2,3-dihydroxy-N-methylbicyclo[3.1.0]hexane-1-carboxamide (331)

Compound 331 (63%) was prepared from compound 344 following the same method as used for compound 327. $^1$H NMR (CD$_3$OD, 400 MHz) δ 8.14 (s, 1H), 7.58 (t, J=8.8 Hz, 1H), 7.47-7.44 (m, 2H), 7.39-7.25 (m, 4H), 5.06 (d, J=6.4 Hz, 1H), 4.89 (s, 1H), 4.04 (d, J=6.4 Hz, 1H), 2.84 (s, 3H), 2.13-2.10 (m, 1H), 1.88 (t, J=4.8 Hz, 1H), 1.41-1.38 (m, 1H). HRMS calculated for C$_{28}$H$_{24}$F$_2$ClN$_6$O$_3$ (M+H)$^+$: 565.1566. found 565.1559.

(1S,2R,3S,4R,5S)-4-(2-((4-Aminophenyl)ethynyl)-6-(3-chlorobenzylamino)-9H-purin-9-yl)-2,3-dihydroxy-N-methylbicyclo[3.1.0]hexane-1-carboxamide (332a)

Compound 332a (59%) was prepared from compound 344 following the same method as used for compound 327. $^1$H NMR (CD$_3$OD, 400 MHz) δ 8.02 (s, 1H), 7.84 (d, J=8.8 Hz, 2H), 7.33-7.23 (m, 4H), 6.60 (d, J=8.4 Hz, 2H), 5.17 (d, J=6.4 Hz, 1H), 4.85 (s, 1H), 4.73 (br s, 2H), 4.02 (d, J=6.8 Hz, 1H), 2.83 (s, 3H), 2.08-2.05 (m, 1H), 1.81 (t, J=4.8 Hz, 1H), 1.41-1.37 (m, 1H). HRMS calculated for C$_{28}$H$_{27}$ClN$_7$O$_3$ (M+H)$^+$: 545.1041. found 545.1045.

3-((6-(3-Chlorobenzylamino)-9-((1S,2R,3S,4R,5S)-3,4-dihydroxy-5-(methylcarbamoyl)bicyclo[3.1.0]hexan-2-yl)-9H-purin-2-yl)ethynyl)benzoic acid (333)

PdCl$_2$(PPh$_3$)$_2$ (3.0 mg, 0.004 mmol), CuI (1.0 mg, 0.004 mmol), phenylacetylene (18.7 mg, 0.12 mmol) and triethylamine (20 μL, 0.2 mmol) was added to a solution of compound 344 (12.68 mg, 0.02 mmol) in anhydrous DMF (1 mL), and stirred at room temperature overnight. Solvent was evaporated under vacuum, and the residue was roughly purified on flash silica gel column chromatography. The resulting compound was dissolved in dioxane (2 mL) and 1N HCl (1.5 mL) and heated at 60° C. for 2 h. After completion of starting material, solvent was evaporated under vacuum, and the residue was purified on flash silica gel column chromatography (CH$_2$Cl$_2$:MeOH:TFA=25:1:0.1) to give compound 333 (7 mg, 61%) as a syrup. $^1$H NMR (CD$_3$OD, 400 MHz) δ 8.28 (s, 1H), 8.18-8.16 (m, 1H), 8.11-8.07 (m, 1H), 7.87 (d, J=7.6 Hz, 1H), 7.59-7.54 (m, 2H), 7.47 (s, 1H), 7.41-7.26 (m, 2H), 5.09 (d, J=6.4 Hz, 1H), 4.91 (s, 1H), 4.05 (d, J=6.4 Hz, 1H), 2.85 (s, 3H), 2.14-2.11 (m, 1H), 1.88 (t, J=4.8 Hz, 1H), 1.42-1.38 (m, 1H). HRMS calculated for C$_{29}$H$_{26}$ClN$_6$O$_5$ (M+H)$^+$: 573.1653. found 573.1646.

(1S,2R,3S,4R,5S)-4-(2-(Biphenyl-4-ylethynyl)-6-(3-chlorobenzylamino)-9H-purin-9-yl)-2,3-dihydroxy-N-methylbicyclo[3.1.0]hexane-1-carboxamide (335)

Compound 335 (68%) was prepared from compound 344 following the same method as used for compound 327. $^1$H NMR (CD$_3$OD, 400 MHz) δ 8.13 (s, 1H), 7.74-7.66 (m, 7H), 7.49-7.45 (m, 2H), 7.40-7.26 (m, 4H), 5.07 (d, J=5.6 Hz, 1H), 4.9 (s, 1H), 4.60 (br s, 2H), 4.05 (d, J=6.4 Hz, 1H), 2.85 (s, 3H), 2.14-2.11 (m, 1H), 1.89 (t, J=4.8 Hz, 1H), 1.42-1.40 (m, 1H). HRMS calculated for C$_{34}$H$_{30}$ClN$_6$O$_3$ (M+H)$^+$: 605.2068. found 605.2083.

(1S,2R,3S,4R,5S)-4-(6-(3-Chlorobenzylamino)-2-(pyren-1-ylethynyl)-9H-purin-9-yl)-2,3-dihydroxy-N-methylbicyclo[3.1.0]hexane-1-carboxamide (336)

Compound 336 (91%) was prepared from compound 344 following the same method as used for compound 327. $^1$H NMR (CD$_3$OD, 400 MHz) δ 8.71 (d, J=9.2 Hz, 1H), 8.26-8.23 (m, 4H), 8.16-8.13 (m, 2H), 8.08-8.03 (m, 3H), 7.54 (s, 1H), 7.43 (d, J=7.6 Hz, 1H), 7.34 (t, J=8.0 Hz, 1H), 7.27 (d, J=8.0 Hz, 1H), 5.06 (d, J=6.4 Hz, 1H), 4.83 (s, 1H), 4.04 (d, J=6.4 Hz, 1H), 2.81 (s, 3H), 2.10-2.07 (m, 1H), 1.89 (t, J=4.8 Hz, 1H), 1.41-1.37 (m, 1H). HRMS calculated for C$_{38}$H$_{30}$ClN$_6$O$_3$ (M+H)$^+$: 653.2068. found 653.2078.

(1S,2R,3S,4R,5S)-Ethyl-(2,3-O-isopropylidene)-4-(2-iodo-6-(methylamino)-9H-purin-9-yl)bicyclo[3.1.0]hexane-1-carboxylate (341)

Methylamine hydrochloride (0.353 g, 5.23 mmol) and triethylamine (1.4 mL, 16.6 mmol) was added to a solution of compound 340 (0.528 g, 1.04 mmol) in anhydrous methanol (15 mL) and stirred at room temperature overnight. Solvent was evaporated under vacuum, and the residue was purified on flash silica gel column chromatography (hexane:ethylacetate=1:1) to give compound 341 (0.470 g, 94%) as a foamy solid. $^1$H NMR (CD$_3$OD, 400 MHz) δ 7.94 (s, 1H), 5.83 (d, J=7.2 Hz, 1H), 4.94 (s, 1H), 4.80 (d, J=6.0 Hz, 1H), 4.33-4.27 (m, 2H), 3.05 (br s, 3H), 2.25-2.21 (m, 1H), 1.65-1.61 (m, 1H), 1.53-1.49 (m, 4H), 1.34 (t, J=7.2 Hz, 3H), 1.29 (s, 3H). HRMS calculated for C$_{18}$H$_{23}$IN$_5$O$_4$ (M+H)$^+$: 500.1072. found 500.1075.

(1S,2R,3S,4R,5S)-(2,3-O-Isopropylidene)-4-(2-iodo-6-(methylamino)-9H-purin-9-yl)-N-methylbicyclo[3.1.0]hexane-1-carboxamide (343)

40% Methylamine solution (10 mL) was added to a solution of compound 341 (0.470, 0.94 mmol) in methanol (15 mL) and stirred at room temperature for 48 h. Solvent was evaporated under vacuum, and the residue was purified on flash silica gel column chromatography (CH$_2$Cl$_2$:MeOH=40:1) to give compound 43 (0.360 g, 79%) as a syrup. $^1$H NMR (CD$_3$OD, 400 MHz) δ 7.95 (s, 1H), 5.72 (d, J=7.2 Hz, 1H), 4.93 (s, 1H), 4.84 (d, J=7.2 Hz, 1H), 3.05 (br s, 3H), 2.90 (s, 3H), 2.17-2.11 (m, 1H), 1.54-1.49 (m, 4H), 1.39 (t, J=5.2 Hz, 1H), 1.30 (s, 3H). HRMS calculated for C$_{17}$H$_{22}$IN$_6$O$_3$ (M+H)$^+$: 485.0798. found 485.0803.

(1S,2R,3S,4R,5S)-(2,3-O-Isopropylidene)-N-methyl-4-(6-(methylamino)-2-(phenylethynyl)-9H-purin-9-yl)bicyclo[3.1.0]hexane-1-carboxamide (345a)

PdCl$_2$(PPh$_3$)$_2$ (5.16 mg, 0.01 mmol), CuI (1.3 mg, 0.007 mmol), phenylacetylene (48 μL, 0.44 mmol) and triethylamine (0.1 mL, 0.73 mmol) was added to a solution of compound 343 (35.6 mg, 0.07 mmol) in anhydrous DMF (1 mL), and stirred at room temperature overnight. Solvent was evaporated under vacuum, and the residue was purified on flash silica gel column chromatography (CH$_2$Cl$_2$:MeOH=40:1) to give compound 345a (29 mg, 86%) as a syrup. $^1$H NMR (CD$_3$OD, 400 MHz) δ 8.13 (s, 1H), 7.73-7.70 (m, 2H), 7.47-7.44 (m, 3H), 5.81 (d, J=7.2 Hz, 1H), 5.03 (s, 1H), 4.85 (d, J=6.8 Hz, 1H), 3.15 (br s, 3H), 2.78 (s, 3H), 2.18-2.14 (m, 1H), 1.57-1.53 (m, 4H), 1.42 (t, J=5.2 Hz, 1H), 1.31 (s, 3H). HRMS calculated for C$_{25}$H$_{27}$N$_6$O$_3$ (M+H)$^+$: 459.2145. found 459.2150.

(1S,2R,3S,4R,5S)-4-(2-((2-Fluorophenyl)ethynyl)-6-(methylamino)-9H-purin-9-yl)-2,3-O-isopropylidene-N-methylbicyclo[3.1.0]hexane-1-carboxamide (345b)

Compound 345b (79%) was prepared from compound 43 following the same method as used for compound 345a. $^1$H NMR (CD$_3$OD, 400 MHz) δ 8.15 (s, 1H), 7.66-7.57 (m, 1H), 7.53-7.47 (m, 1H), 7.30-7.23 (m, 2H), 5.79 (d, J=7.2 Hz, 1H), 5.04 (s, 1H), 3.15 (br s, 3H), 2.76 (s, 3H), 2.17-2.14 (m, 1H), 1.57-1.53 (m, 4H), 1.42 (t, J=5.2 Hz, 1H), 1.31 (s, 3H). HRMS calculated for C$_{25}$H$_{26}$FN$_6$O$_3$ (M+H)$^+$: 477.2050. found 477.2040.

(1S,2R,3S,4R,5S)-4-(2-((3-Fluorophenyl)ethynyl)-6-(methylamino)-9H-purin-9-yl)-2,3-O-isopropylidene-N-methylbicyclo[3.1.0]hexane-1-carboxamide (345c)

Compound 345c (75%) was prepared from compound 343 following the same method as used for compound 345a. $^1$H NMR (CD$_3$OD, 400 MHz) δ 8.14 (s, 1H), 7.66-7.53 (m, 2H), 7.50-7.45 (m, 1H), 7.25-7.20 (m, 1H), 5.81 (d, J=7.2 Hz, 1H), 5.03 (s, 1H), 3.15 (br s, 3H), 2.78 (s, 3H), 2.18-2.14 (m, 1H), 1.57-1.53 (m, 4H), 1.43 (t, J=5.2 Hz, 1H), 1.31 (s, 3H). HRMS calculated for C$_{25}$H$_{26}$FN$_6$O$_3$ (M+H)$^+$: 477.2050. found 477.2052.

(1S,2R,3S,4R,5S)-4-(2-((4-Fluorophenyl)ethynyl)-6-(methylamino)-9H-purin-9-yl)-2,3-O-isopropylidene-N-methylbicyclo[3.1.0]hexane-1-carboxamide (345d)

Compound 345d (77%) was prepared from compound 343 following the same method as used for compound 345a. $^1$H NMR (CD$_3$OD, 400 MHz) δ 8.14 (s, 1H), 7.78-7.72 (m, 2H), 7.23-7.19 (m, 2H), 5.80 (d, J=6.8 Hz, 1H), 5.03 (s, 1H), 3.14 (br s, 3H), 2.77 (s, 3H), 2.17-2.14 (m, 1H), 1.56-1.43 (m, 4H), 1.43 (t, J=5.6 Hz, 1H), 1.31 (s, 3H). HRMS calculated for C$_{25}$H$_{26}$FN$_6$O$_3$ (M+H)$^+$: 477.2050. found 477.2033.

(1S,2R,3S,4R,5S)-4-(2-((2-Chlorophenyl)ethynyl)-6-(methylamino)-9H-purin-9-yl)-2,3-O-isopropylidene-N-methylbicyclo[3.1.0]hexane-1-carboxamide (345e)

Compound 345e (81%) was prepared from compound 343 following the same method as used for compound 345a. $^1$H NMR (CD$_3$OD, 400 MHz) δ 8.15 (s, 1H), 7.78 (d, J=5.6 Hz, 1H), 7.57 (d, J=6.8 Hz, 1H), 7.47-7.38 (m, 2H), 5.81 (d, J=6.0 Hz, 1H), 5.04 (s, 1H), 4.91 (d, J=7.2 Hz, 1H) 3.15 (br s, 3H), 2.74 (s, 3H), 2.17-2.13 (m, 1H), 1.56-1.52 (m, 4H), 1.41 (t, J=5.2 Hz, 1H), 1.31 (s, 3H). HRMS calculated for C$_{25}$H$_{26}$ClN$_6$O$_3$ (M+H)$^+$: 493.1755. found 493.1749.

(1S,2R,3S,4R,5S)-4-(2-((3-Chlorophenyl)ethynyl)-6-(methylamino)-9H-purin-9-yl)-2,3-O-isopropylidene-N-methylbicyclo[3.1.0]hexane-1-carboxamide (345f)

Compound 345f (79%) was prepared from compound 343 following the same method as used for compound 345a. $^1$H NMR (CD$_3$OD, 400 MHz) δ 8.15 (s, 1H), 7.75 (s, 1H), 7.67-7.63 (m, 1H), 7.50-7.42 (m, 2H), 5.81 (d, J=6.8 Hz, 1H), 5.03 (s, 1H), 3.14 (br s, 3H), 2.78 (s, 3H), 2.18-2.15 (m, 1H), 1.57-1.53 (m, 4H), 1.43 (t, J=5.2 Hz, 1H), 1.31 (s, 3H). HRMS calculated for C$_{25}$H$_{26}$ClN$_6$O$_3$ (M+H)$^+$: 493.1755. found 493.1762.

(1S,2R,3S,4R,5S)-4-(2-((4-Chlorophenyl)ethynyl)-6-(methylamino)-9H-purin-9-yl)-2,3-O-isopropylidene-N-methylbicyclo[3.1.0]hexane-1-carboxamide (345g)

Compound 345g (82%) was prepared from compound 343 following the same method as used for compound 345a. $^1$H NMR (CD$_3$OD, 400 MHz) δ 8.14 (s, 1H), 7.70 (d, J=8.4 Hz, 2H), 7.47 (d, J=8.4 Hz, 2H), 5.80 (d, J=7.2 Hz, 1H), 5.03 (s, 1H), 3.14 (br s, 3H), 2.77 (s, 3H), 2.20-2.14 (m, 1H), 1.55-1.53 (m, 4H), 1.43 (t, J=5.2 Hz, 1H), 1.31 (s, 3H). HRMS calculated for C$_{25}$H$_{26}$ClN$_6$O$_3$ (M+H)$^+$: 493.1755. found 493.1771.

(1S,2R,3S,4R,5S)-4-(2-((4-Bromophenyl)ethynyl)-6-(methylamino)-9H-purin-9-yl)-2,3-O-isopropylidene-N-methylbicyclo[3.1.0]hexane-1-carboxamide (345h)

Compound 345h (74%) was prepared from compound 343 following the same method as used for compound 345a. $^1$H NMR (CD$_3$OD, 400 MHz) δ 8.13 (s, 1H), 7.67-7.61 (m, 2H), 7.57-7.55 (m, 2H), 5.79 (d, J=7.2 Hz, 1H), 5.03 (s, 1H), 3.14 (br s, 3H), 2.78 (s, 3H), 2.21-2.14 (m, 1H), 1.54-1.53 (m, 4H), 1.43 (t, J=5.2 Hz, 1H), 1.31 (s, 3H). HRMS calculated for C$_{25}$H$_{26}$BrN$_6$O$_3$ (M+H)$^+$: 537.1250. found 537.1234.

(1S,2R,3S,4R,5S)-4-(2-((3-Aminophenyl)ethynyl)-6-(methylamino)-9H-purin-9-yl)-2,3-O-isopropylidene-N-methylbicyclo[3.1.0]hexane-1-carboxamide (345i)

Compound 345i (71%) was prepared from compound 343 following the same method as used for compound 345a. $^1$H NMR (CD$_3$OD, 400 MHz) δ 8.12 (s, 1H), 7.16 (t, J=8.0 Hz, 1H), 7.01 (t, J=7.6 Hz, 2H), 6.80 (d, J=6.4 Hz, 1H), 5.79 (d, J=6.8 Hz, 1H), 5.03 (s, 1H), 3.15 (br s, 3H), 2.79 (s, 3H), 2.16-2.13 (m, 1H), 1.56-1.53 (m, 4H), 1.41 (t, J=5.2 Hz, 1H), 1.31 (s, 3H). HRMS calculated for C$_{27}$H$_{33}$N$_7$O$_3$ (M+H)$^+$: 474.2254. found 474.2262.

(1S,2R,3S,4R,5S)-4-(2-((3,4-Difluorophenyl)ethynyl)-6-(methylamino)-9H-purin-9-yl)-2,3-O-isopropylidene-N-methylbicyclo[3.1.0]hexane-1-carboxamide (345j)

Compound 345j (81%) was prepared from compound 343 following the same method as used for compound 345a. $^1$H NMR (CD$_3$OD, 400 MHz) δ 8.17 (s, 1H), 7.67-7.63 (m, 1H), 7.59-7.54 (m, 1H), 7.41-7.34 (m, 1H), 5.81 (d, J=6.8 Hz, 1H), 5.03 (s, 1H), 3.14 (br s, 3H), 2.77 (s, 3H), 2.18-2.14 (m, 1H), 1.57-1.53 (m, 4H), 1.43 (t, J=5.2 Hz, 1H), 1.31 (s, 3H). HRMS calculated for $C_{25}H_{25}F_2N_6O_3$ (M+H)$^+$ : 495.1956. found 495.1945.

(1S,2R,3S,4R,5S)-4-(2-((3,5-Difluorophenyl)ethynyl)-6-(methylamino)-9H-purin-9-yl)-2,3-O-isopropylidene-N-methylbicyclo[3.1.0]hexane-1-carboxamide (345k)

Compound 345k (82%) was prepared from compound 343 following the same method as used for compound 345a. $^1$H NMR (CD$_3$OD, 400 MHz) δ 8.15 (s, 1H), 7.68-7.55 (m, 1H), 7.38-7.35 (m, 1H), 7.14-7.09 (m, 1H), 5.81 (d, J=7.2 Hz, 1H), 5.03 (s, 1H), 3.14 (br s, 3H), 2.77 (s, 3H), 2.18-2.15 (m, 1H), 1.56-1.53 (m, 4H), 1.44 (t, J=5.2 Hz, 1H), 1.31 (s, 3H). HRMS calculated for $C_{25}H_{25}F_2N_6O_3$ (M+H)$^+$ : 495.1956. found 495.1966.

(1S,2R,3S,4R,5S)-4-(2-((4-Ethylphenyl)ethynyl)-6-(methylamino)-9H-purin-9-yl)-2,3-O-isopropylidene-N-methylbicyclo[3.1.0]hexane-1-carboxamide (345l)

Compound 345l (78%) was prepared from compound 343 following the same method as used for compound 345a. $^1$H NMR (CD$_3$OD, 400 MHz) δ 8.12 (s, 1H), 7.62 (d, J=8.0 Hz, 2H), 7.30 (d, J=8.0 Hz, 2H), 5.80 (d, J=6.4 Hz, 1H), 5.03 (s, 1H), 3.15 (br s, 3H), 2.78 (s, 3H), 2.72 (q, J=7.6 Hz, 2H), 2.17-2.13 (m, 1H), 1.57-1.53 (m, 4H), 1.42 (t, J=5.2 Hz, 1H), 1.31-1.28 (m, 6H). HRMS calculated for $C_{27}H_{31}N_6O_3$ (M+H)$^+$ : 487.2458. found 487.2451.

(1S,2R,3S,4R,5S)-4-(2-((4-tert-Butylphenyl)ethynyl)-6-(methylamino)-9H-purin-9-yl)-2,3-O-isopropylidene-N-methylbicyclo[3.1.0]hexane-1-carboxamide (345m)

Compound 345m (74%) was prepared from compound 343 following the same method as used for compound 345a. $^1$H NMR (CD$_3$OD, 400 MHz) δ 8.15 (s, 1H), 7.64 (d, J=8.0 Hz, 2H), 7.50 (d, J=8.0 Hz, 2H), 5.81 (d, J=6.8 Hz, 1H), 5.04 (s, 1H), 3.15 (br s, 3H), 2.78 (s, 3H), 2.19-2.13 (m, 1H), 1.58-1.53 (m, 4H), 1.42 (t, J=5.2 Hz, 1H), 1.37 (s, 9H), 1.33 (s, 3H). HRMS calculated for $C_{29}H_{35}N_6O_3$ (M+H)$^+$ : 515.2771. found 515.2751.

(1S,2R,3S,4R,5S)-4-(2-((4-Acetylphenyl)ethynyl)-6-(methylamino)-9H-purin-9-yl)-2,3-O-isopropylidene-N-methylbicyclo[3.1.0]hexane-1-carboxamide (345n)

Compound 345n (82%) was prepared from compound 343 following the same method as used for compound 345a. $^1$H NMR (CD$_3$OD, 400 MHz) δ 8.15 (s, 1H), 8.08 (d, J=8.4 Hz, 2H), 7.84 (d, J=8.4 Hz, 2H), 5.81 (d, J=6.8 Hz, 1H), 5.04 (s, 1H), 3.14 (br s, 3H), 2.77 (s, 3H), 2.65 (s, 3H), 2.19-2.15 (m, 1H), 1.56-1.53 (m, 4H), 1.44 (t, J=5.2 Hz, 1H), 1.31 (s, 3H). HRMS calculated for $C_{27}H_{29}N_6O_4$ (M+H)$^+$ : 501.2250. found 501.2245.

(1S,2R,3S,4R,5S)-4-(2-(Biphenyl-4-ylethynyl)-6-(methylamino)-9H-purin-9-yl)-2,3-O-isopropylidene-N-methylbicyclo[3.1.0]hexane-1-carboxamide (435o)

Compound 345o (85%) was prepared from compound 343 following the same method as used for compound 345a. $^1$H NMR (CD$_3$OD, 400 MHz) δ 8.13 (s, 1H), 7.79 (d, J=8.4 Hz, 2H), 7.74-7.68 (m, 4H), 7.48 (t, J=7.2 Hz, 2H), 7.41-7.37 (m, 1H), 5.82 (d, J=6.8 Hz, 1H), 5.04 (s, 1H), 3.16 (br s, 3H), 2.80 (s, 3H), 2.18-2.15 (m, 1H), 1.57-1.54 (m, 4H), 1.43 (t, J=5.2 Hz, 1H), 1.34 (s, 3H). HRMS calculated for $C_{31}H_{31}N_6O_4$ (M+H)$^+$ : 535.2458. found 535.2477.

(1S,2R,3S,4R,5S)-4-(2-((Naphthalene-1-yl)ethynyl)-6-(methylamino)-9H-purin-9-yl)-2,3-O-isopropylidene-N-methylbicyclo[3.1.0]hexane-1-carboxamide (345p)

Compound 345p (76%) was prepared from compound 343 following the same method as used for compound 345a. $^1$H NMR (CD$_3$OD, 400 MHz) δ 8.56 (d, J=8.4 Hz, 1H), 8.15 (s, 1H), 8.01-7.96 (m, 2H), 7.75-7.51 (m, 4H), 5.85 (d, J=7.2 Hz, 1H), 5.08 (s, 1H), 4.93 (d, J=7.2 Hz, 1H) 3.15 (br s, 3H), 2.68 (s, 3H), 2.21-2.18 (m, 1H), 1.57-1.54 (m, 4H), 1.43 (t, J=5.2 Hz, 1H), 1.34 (s, 3H). HRMS calculated for $C_{29}H_{28}N_6O_3Na$ (M+Na)$^+$: 531.2121. found 531.2114.

(1S,2R,3S,4R,5S)-4-(2-((Phenanthren-9-yl)ethynyl)-6-(methylamino)-9H-purin-9-yl)-2,3-O-isopropylidene-N-methylbicyclo[3.1.0]hexane-1-carboxamide (345q)

Compound 345b (71%) was prepared from compound 343 following the same method as used for compound 345a. $^1$H NMR (CD$_3$OD, 400 MHz) δ 8.87-8.78 (m, 2H), 8.67-8.66 (m, 1H), 8.35 (s, 1H), 8.15 (s, 1H), 8.02-7.99 (m, 2H), 7.79-7.63 (m, 3H), 5.88 (d, J=6.8 Hz, 1H), 5.09 (s, 1H), 4.95 (d, J=7.2 Hz, 1H) 3.18 (br s, 3H), 2.69 (s, 3H), 2.25-2.18 (m, 1H), 1.58-1.54 (m, 4H), 1.44 (t, J=5.2 Hz, 1H), 1.35 (s, 3H). HRMS calculated for $C_{33}H_{31}N_6O_3$ (M+H)$^+$ : 559.2458. found 559.2462.

(1S,2R,3S,4R,5S)-(2,3-O-Isopropylidene)-N-methyl-4-(6-(methylamino)-2-(pyridin-2-ylethynyl)-9H-purin-9-yl)bicyclo[3.1.0]hexane-1-carboxamide (346)

Compound 346 (78%) was prepared from compound 343 following the same method as used for compound 345a. $^1$H NMR (CD$_3$OD, 400 MHz) δ 8.65 (d, J=4.4 Hz, 1H), 8.16 (s, 1H), 7.98 (t, J=6.0 Hz, 1H), 7.85 (d, J=8.0 Hz, 1H), 7.57-7.51 (m, 1H), 6.00 (d, J=6.8 Hz, 1H), 5.01 (s, 1H), 4.95 (d, J=7.2 Hz, 1H), 3.13 (br s, 3H), 2.73 (s, 3H), 2.11-2.07 (m, 1H), 1.59-1.56 (m, 4H), 1.41 (t, J=5.2 Hz, 1H), 1.33 (s, 3H). HRMS calculated for $C_{24}H_{26}N_7O_3$ (M+H)$^+$ : 460.2097. found 460.2079.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (V):

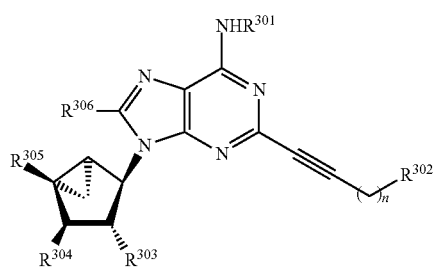

(V)

$R^{301}$ is selected from the group consisting of $C_1$-$C_6$ alkyl, $C_1$-$C_6$ alkoxy, hydroxyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl)amino]-carbonyl]-$C_1$-$C_6$ alkyl]anilino]carbonyl]$C_1$-$C_6$ alkyl]$C_6$-$C_{14}$ aryl, and $C_6$-$C_{14}$ aryl $C_3$-$C_8$ cycloalkyl, wherein the aryl or heterocyclyl portion of $R^{301}$ is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof; and the alkyl or cycloalkyl portion of $R^{301}$ is optionally substituted with one or more substituents selected from the group consisting of halo, amino, alkyl, alkoxy, aryloxy, hydroxyalkyl, hydroxyalkenyl, hydroxyalkynyl, aminocarbonylalkoxy, and arylalkoxy, and any combination thereof;

$R^{302}$ is $C_6$-$C_{16}$ aryl or heteroaryl; wherein the aryl group is optionally substituted with one or more substituents selected from the group consisting of halo, amino, alkyl, aryl, carboxyl, $SO_3H$, carboxyalkyl, sulfonyloxyalkyl, alkylcarbonyl, and arylcarbonyl; and the heteroaryl group is optionally substituted with one or more substituents selected from the group consisting of halo, amino, alkyl, carboxyl, $SO_3H$, carboxyalkyl, sulfonyloxyalkyl, alkylcarbonyl, and arylcarbonyl;

$R^{303}$ and $R^{304}$ are independently selected from the group consisting of hydroxyl, amino, mercapto, ureido, $C_1$-$C_6$ alkyl carbonylamino, hydroxy $C_1$-$C_6$ alkyl, and hydrazinyl; and $R^{305}$ is selected from the group consisting of hydrogen, $C_1$-$C_3$ alkyl aminocarbonyl, di($C_1$-$C_3$ alkyl)aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl;

$R^{306}$ is selected from the group consisting of hydrogen, $C_1$-$C_6$ alkyl, $C_2$-$C_6$ alkenyl, $C_2$-$C_6$ alkynyl, heteroaryl, and $C_1$-$C_6$ aminoalkyl;

n is 0-6;

or a pharmaceutically acceptable salt thereof.

2. The compound or salt of claim 1, wherein $R^{306}$ is hydrogen.

3. The compound or salt of claim 1, wherein $R^{305}$ is selected from the group consisting of $C_1$-$C_3$ alkyl aminocarbonyl or di($C_1$-$C_3$ alkyl)aminocarbonyl.

4. The compound or salt of claim 1, wherein $R^{303}$ and $R^{304}$ are both hydroxyl.

5. The compound or salt of claim 1, wherein $R^{301}$ is selected from the group consisting of $C_1$-$C_6$ alkyl, $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, heterocyclyl $C_1$-$C_6$ alkyl, heterocyclyl, and $C_6$-$C_{14}$ aryl $C_3$-$C_8$ cycloalkyl, wherein the aryl or heterocyclyl portion of $R^{301}$ is optionally substituted with one or more substituents selected from the group consisting of halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, aminocarbonyl $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof and the alkyl or cycloalkyl portion of $R^{301}$ is optionally substituted with one or more substituents selected from the group consisting of halo, amino, alkyl, alkoxy, aryloxy, hydroxyalkyl, hydroxyalkenyl, hydroxyalkynyl, aminocarbonylalkoxy, and arylalkoxy, and any combination thereof.

6. The compound or salt of claim 5, wherein $R^{301}$ is selected from the group consisting of $C_1$-$C_6$ alkyl, $C_3$-$C_8$ cycloalkyl, $C_3$-$C_8$ cycloalkyl $C_1$-$C_6$ alkyl, $C_6$-$C_{14}$ aryl $C_1$-$C_6$ alkyl, and heterocyclyl $C_1$-$C_6$ alkyl, wherein the aryl or heterocyclyl portion of $R^{301}$ is optionally substituted with one or more substituents selected from the group consisting of halo, amino, hydroxyl, carboxy, alkoxycarbonyl, aminocarbonyl, alkylaminocarbonyl, dialkylaminocarbonyl, and $C_1$-$C_6$ alkyl, and any combination thereof and the alkyl or cycloalkyl portion of $R^{301}$ is optionally substituted with one or more substituents selected from the group consisting of halo, amino, alkyl, alkoxy, and aryloxy, and any combination thereof.

7. The compound or salt of claim 5, wherein $R^{301}$ is $C_1$-$C_6$ alkyl.

8. The compound or salt of claim 5, wherein $R^{301}$ is selected from the group consisting of benzyl, 3-chlorobenzyl, and 3-iodobenzyl.

9. The compound or salt of claim 1, wherein $R^{302}$ is $C_6$-$C_{16}$ aryl; and the aryl group is optionally substituted with one or more substituents selected from the group consisting of halo, amino, alkyl, aryl, carboxyl, and $SO_3H$.

10. The compound or salt of claim 1, wherein $R^{302}$ is selected from the group consisting of 2-pyridyl, 3-pyridyl, and 4-pyridyl.

11. The compound or salt of claim 1, wherein $R^{301}$ is $C_1$-$C_6$ alkyl or 3-chlorobenzyl; $R^{302}$ is $C_6$-$C_{16}$ aryl; wherein the aryl group is optionally substituted with one or more substituents selected from the group consisting of halo, amino, alkyl, aryl, carboxyl, and $SO_3H$; $R^{303}$ and $R^{304}$ are both hydroxyl; $R^{305}$ is $C_1$-$C_3$ alkyl aminocarbonyl; $R^{306}$ is hydrogen; and n is 0.

12. The compound or salt of claim 1, wherein the compound is selected from the group consisting of:

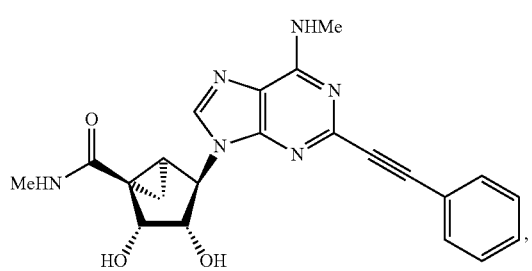

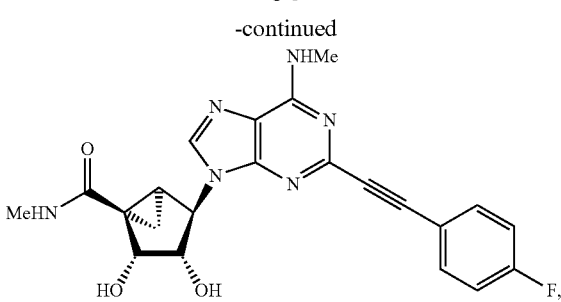

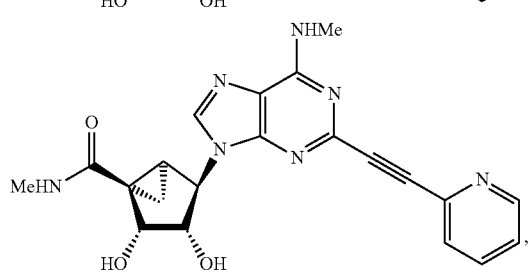

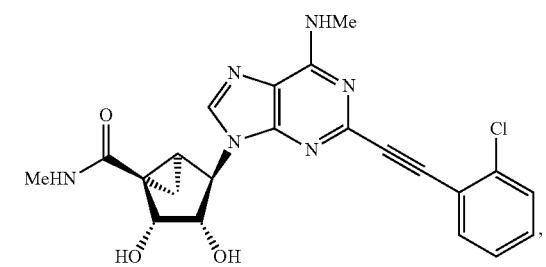

-continued

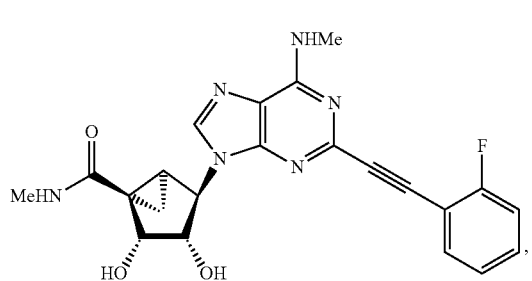

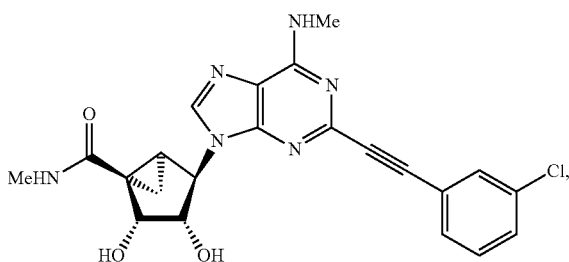

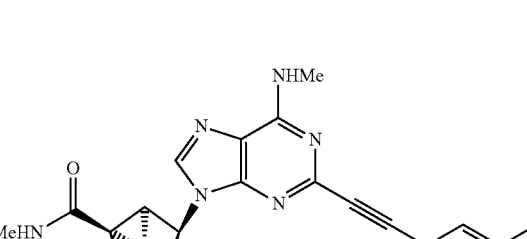

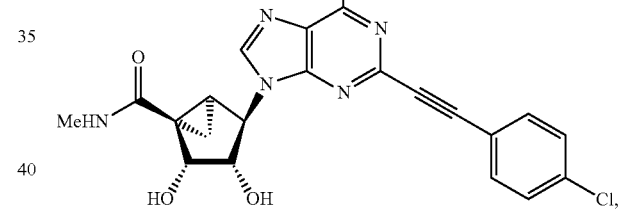

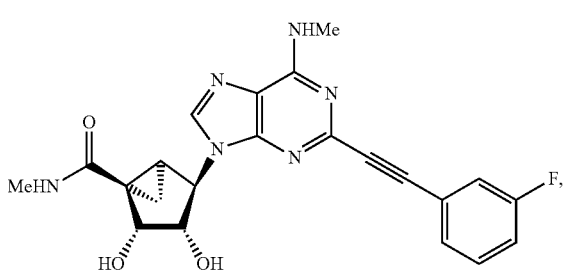

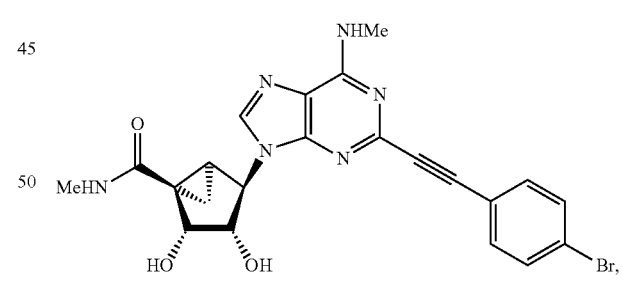

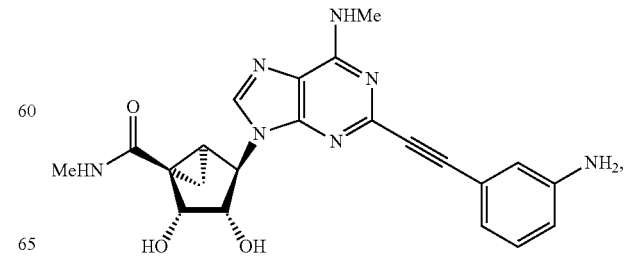

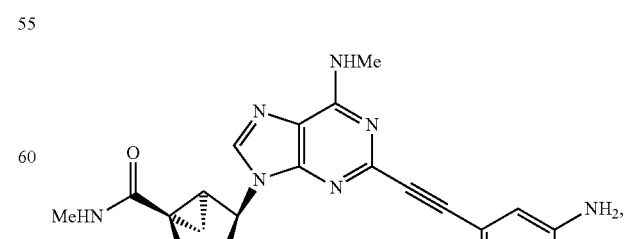

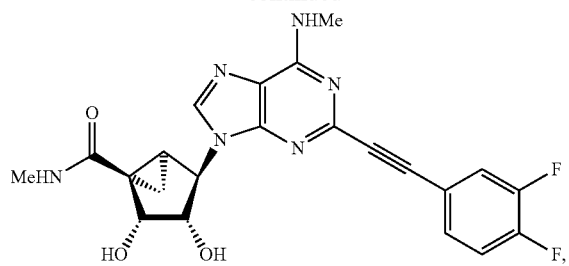
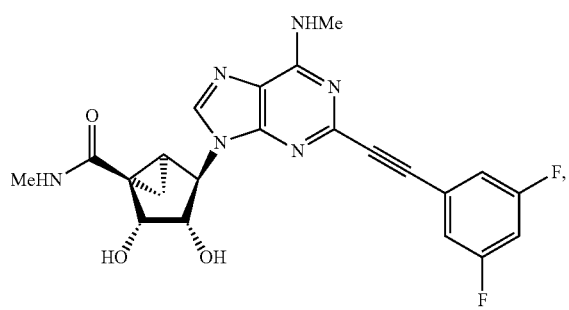
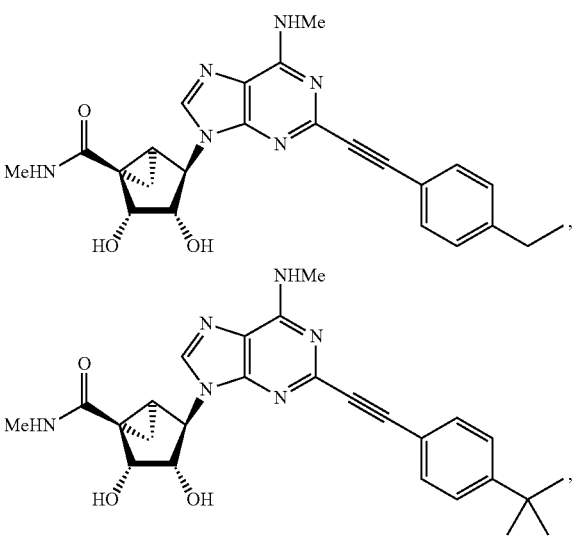
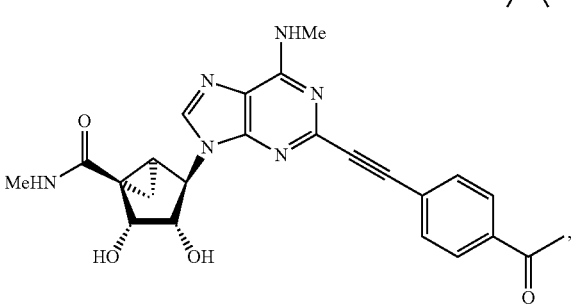
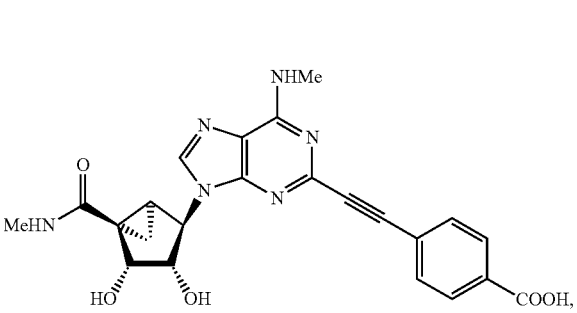
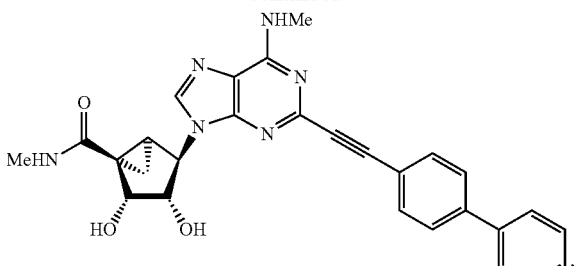
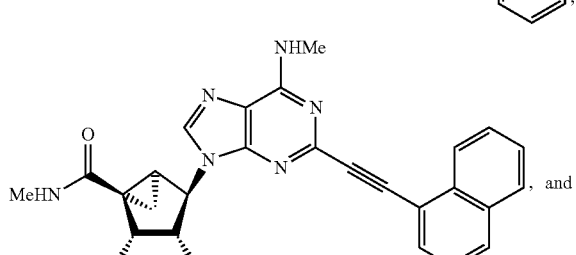
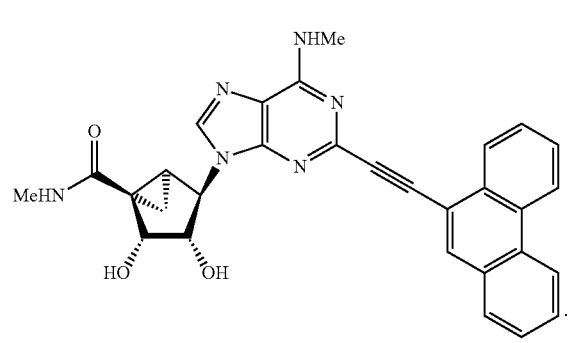
13. The compound of claim 1, wherein the compound is selected from the group consisting of:
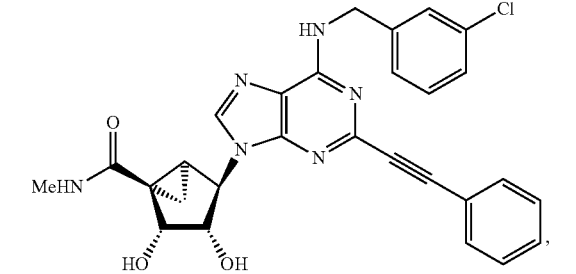
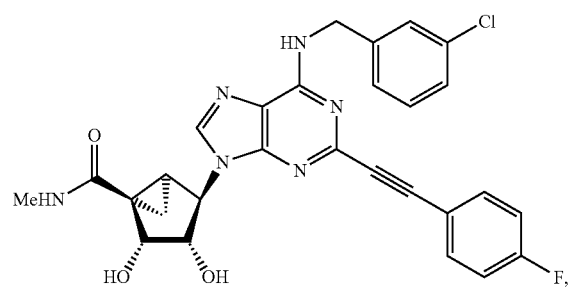

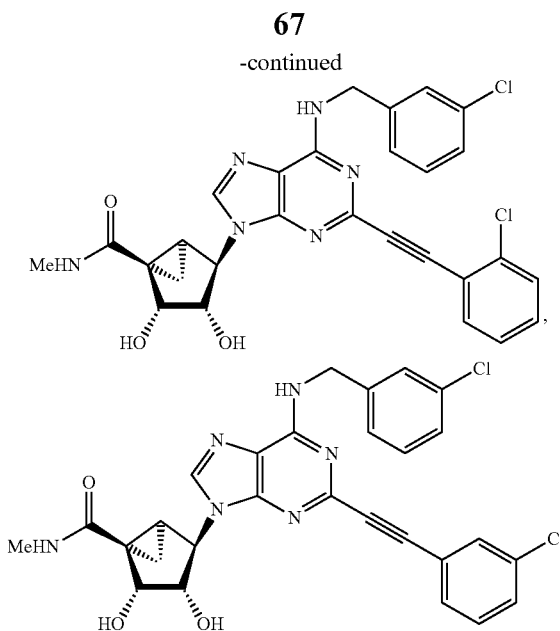

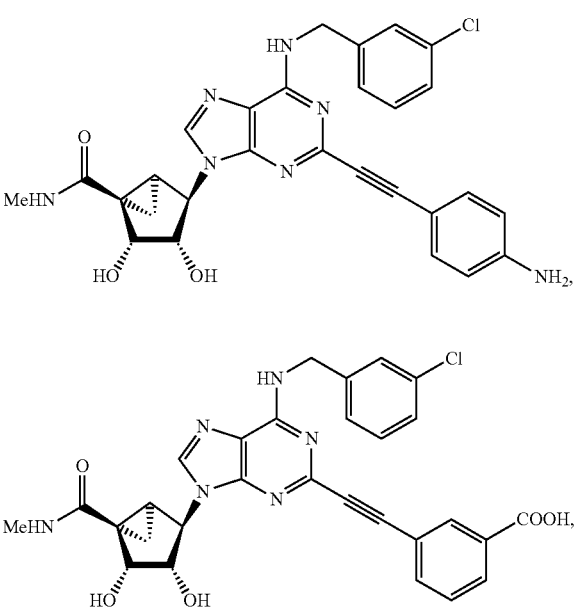

or a pharmaceutically acceptable salt thereof.

14. A pharmaceutical composition comprising a compound of claim 1 or a pharmaceutically acceptable salt thereof and a pharmaceutically acceptable carrier.

15. A method for activating an $A_3$ adenosine receptor in a mammal comprising administering to the mammal an effective amount of a compound of claim 1 or a pharmaceutically acceptable salt thereof.

16. A method for activating an $A_3$ adenosine receptor in a cell comprising contacting said cell with a compound of claim 1 or a pharmaceutically acceptable salt thereof.

17. A method of reducing ischemic damage to the heart of a patient in need thereof comprising administering to the patient an effective amount of a compound of claim 1 or a pharmaceutically acceptable salt thereof.

18. A method of treating a disease, state or condition in a patient in need thereof comprising administering to the patient an effective amount of a compound of claim 1 or a pharmaceutically acceptable salt thereof, wherein the disease, state or condition is selected from the group consisting of ischemia and reperfusion injury in skeletal muscle, neuropathic pain, dry eye syndrome, loss of skin pigmentation, pulmonary inflammation, and uveitis.

* * * * *